United States Patent [19]
Laibovitz et al.

[11] Patent Number: 6,159,188
[45] Date of Patent: Dec. 12, 2000

[54] APPARATUS AND METHOD FOR DELIVERY OF MICRO AND SUBMICRO QUANTITIES OF MATERIALS

[75] Inventors: Robert A. Laibovitz, 7506 Valley Dale Dr.; Robert L. Rogers, 7604 Long Point Dr., both of Austin, Tex. 78731

[73] Assignees: Robert L. Rogers; Robert A. Laibovitz, both of Austin, Tex.

[21] Appl. No.: 09/184,842

[22] Filed: Nov. 2, 1998

Related U.S. Application Data

[63] Continuation-in-part of application No. 09/006,720, Jan. 14, 1998, Pat. No. 5,997,518.

[51] Int. Cl.[7] .................................................. A61M 35/00
[52] U.S. Cl. .......................... 604/294; 604/296; 604/289
[58] Field of Search ................................. 604/19, 23, 24, 604/28, 38, 289, 290, 310, 311; 222/333, 340, 360, 390, 387, 494

[56] References Cited

U.S. PATENT DOCUMENTS

| | | | |
|---|---|---|---|
| 3,934,585 | 1/1976 | Maurice . | |
| 4,623,337 | 11/1986 | Maurice | 604/298 |
| 5,053,000 | 10/1991 | Booth et al. | 604/289 |
| 5,207,659 | 5/1993 | Pennaneac'h et al. | 604/298 |
| 5,630,793 | 5/1997 | Rowe | 604/289 |
| 5,685,869 | 11/1997 | Py | 604/294 |

OTHER PUBLICATIONS

Bartlett, J. and Jaanus, M., In Clinical Ocular Pharmacology, 2nd Edition, Butterworths, London,5:95–148, 1989.

Brown, R.H., Hotchkiss, M.L., Davis E.B., "Creating Smaller Eyedrops by Reducing Eyedropper Tip Dimensions," American Journal of Ophthalmology, 99:460–464, 1985.

Brown, R.H., Lynch, M.G., Wood, S. Osetinsky, M., Schoenwald, R.D., "Reducing Eyedrop Size Decreases Systemic Absorption of 10% Phenylephrine," Invest. Ophthalmol & Vis. Sci. 27(Suppl):102, 1986.

Brown, R.H., Wood, T.S. Lynch, M.G., Schoenwald, R.D., Chien, D., Jennings, L.W., "Improving the Therapeutic Index of Topical Phenylephrine by Reducing Drop Volume," Ophthalmology, 94:847–850, 1987.

Chrai, S.S., Makoid, T.F., Eriksen, S.P., Robinson, J.R., "Drop Size and Initial Dosing FrequencyProblems ofTopically Applied Ophthalmic Drugs," J. Pharm. Sci., 63:333–338, 1974.

(List continued on next page.)

*Primary Examiner*—Mark O. Polutta
*Assistant Examiner*—David J. Cho
*Attorney, Agent, or Firm*—David Allen Roth

[57] ABSTRACT

A process and apparatus (invention) permitting the distribution of micro or submicro liter or gram (exceptionally small) quantities of liquids and powders, (hereafter materials) in patterns and quantities that are especially well-suited for ophthalmologic patient self-application of drugs to his own eye(s) with substantially no overdose. The invention is thus also highly beneficial in those many topical drug applications where overdoses should be avoided. This is particularly applicable for the eye, where overdoses can have many deleterious medical consequences. Use of the invention permits exceptionally small doses of ophthalmologic drugs. Moreover, it also permits the repeatability of the quantity size of the materials chosen for delivery. In the case of drugs, particularly opthomologic drugs, this means that the invention permits the repeated multiple distribution of the same chosen drug/carrier quantity resulting in a uniform repeatable dosage. Variation of dose from one application to another is very unacceptable. The preferred apparatus of the invention employs a venturi configuration inventively modified which uses gas under pressure to pump exceptionally small quantities of material from a reservoir for delivery. In especially preferred embodiments of the invention, said reservoir is pressurized by at least a quantity of gas at somewhat above atmospheric. prior to the removal of any material by pumping.

29 Claims, 30 Drawing Sheets

OTHER PUBLICATIONS

Chrai, S.S., Patton, T.F., Mehta, A., Robinson, J.R., "Lacrimal and Instilled Fluid Dynamics inRabbit Eyes," J. Pharm. Sci., 62:1112–1121, 1973.

Edman, P., Editor, In: Pharmacokinetics of Ocular Drug Delivery, CRCPress, Boca Raton,Florida, 159–191, 1993.

File, R.R., and Patton, T.F., "Topically Applied Pilocarpine," Arch. Ophthalmol.,98:112–115, 1980.

Fox, R.W., and McDonald, A.T.; *Introduction to Fluid Mechanics* Fourth Edition,Wiley and Sons,New York, 4:96–192, 1992.

Gosline, J.E., and O'Brien, P., ïThe Water Jet Pump,î In: *California University Publications in Engineering,* vol. 3, University of California Press, Berkley, California, pp. 167–190, 1937.

Gray, R.H., "The Influence of Drop Size on Pupil Dilatation," Eye, 5:615–619,1991.

Himmelstein, K.J., Guvenir, I., Patton, T.F., "Preliminary Pharmacokinetic Model of Pilocarpine Uptake and Distribution in the Eye," J. Pharm. Sci., 67:603–606, 1978.

Jumpeter, A., "Jet Pumps," In: *Pump Handbook,* Second Edition, McGraw–Hill, 4:1–27, 1986.

Lynch, M.G., Brown, R.H., Goode, S.M., Schoenwald, R.D., Chien, D., "Reduction of Phenylephrine Drop Size in Infants Achieves Equal Dilation With Decreased Systemic Absorption," Arch. Ophthalmol., 105:1364–1365, 1987.

Patton and Francoeur, "Ocular Bioavailability and Systemic Loss of Topically AppliedOphthalmic Drugs," Ama. J. Ophthalmol., 85:225–229, 1978.

Patton, T.F., "Pharmacokinetic Evidence for Improved Ophthalmic DrugDelivery by Reduction of Instilled Volume," J. Pharm. Sci., 66:1058–1059, 1977.

Petursson, G., Cole, R., Hanna, C.H., "Treatment of Glaucoma using Minidrops ofClonidine," Arch.Ophthalmol., 102:1180–1181, 1984.Sears, M.L., Editor,.

"Pharmacology of the Eye," Springer–Verlag, Berlin,1984, Shell, J., 1982, Pharmacokinetics of Topically Applied Ophthalmic Drugs, Survey of Ophthalmology, Jan.–Feb. 26:207–218, 1982.

ïOccular Treatment Device,î Rocca, S.A., Embleton, J., K., Jones, S.P., Applicant: Scherer Limited, International Application Number PCT/GB95/01482, International Publication Number WO 96/00050, International Publication Date: Jan. 4, 1996.

ïOphthalmic Treatment,î Embleton, J., K., Malcomson, R., J., Martini, L.G.A., Applicant: Scherer Limited, International Application Number. PCT/GB96/03195, International Publication Number WO 97/23177, International Publication Date: Jul. 3, 1997.

ïOccular Treatment Device,î Embleton, J., K. Jones, S.P., Malcomson, R., J., Martini, L.G.A., Houzego, P.J., Rocca, A.A., Stevens, H.N.E., Applicant: Scherer Limited, International Application Number. PCT/GB95/02040, International Publication Number. WO 96/06581, International Publication Date: Mar. 7, 1996.

Harkins, W.D., and Brown, F.E., the Determination of Sufrace Tension(Free Surface Energy), and The Weight of Falling Drops: The Surface Tension of Water and Benzene by the Capillary Height Method. *Journal of the American Chemical Society,* vol. 41, 1919, pp. 499–524. [B].

Chattoraj, D.K., and Birdi, K.S., *Adsorption and the Gibbs SurfaceExcess,* Plenum Press, New York, 1984.

Granger, R.A., *Fluid Mechanics,* Dover Publication, New York, 1995.

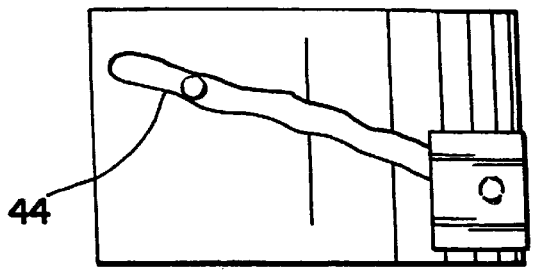
Fig. 4A
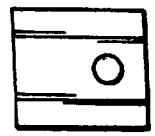
Fig. 4C
Fig. 4B
Fig. 4D
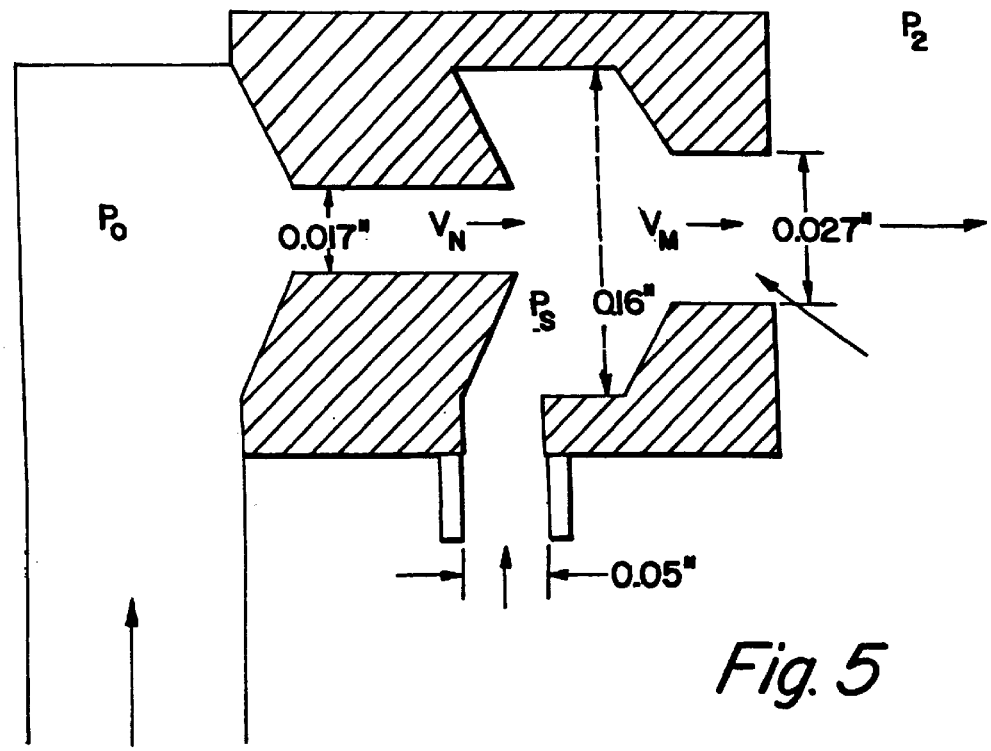
Fig. 5

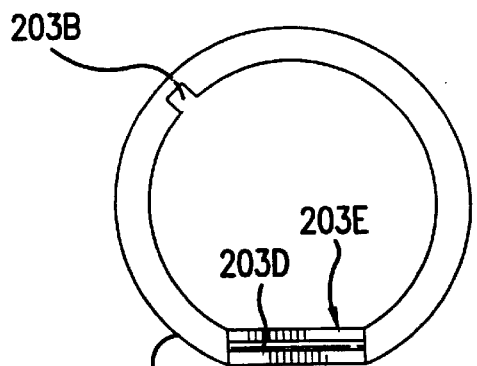
FIG.19A
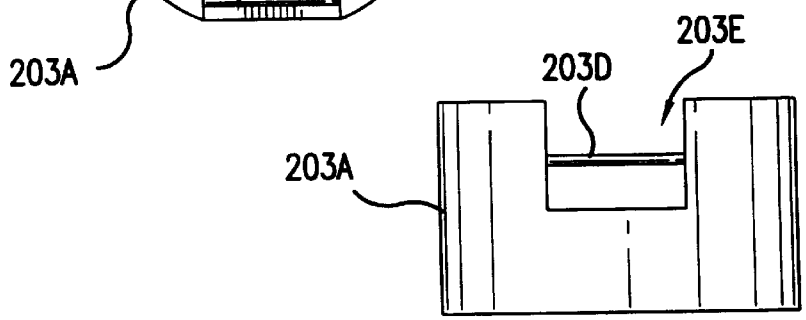
FIG.19B
FIG.19C
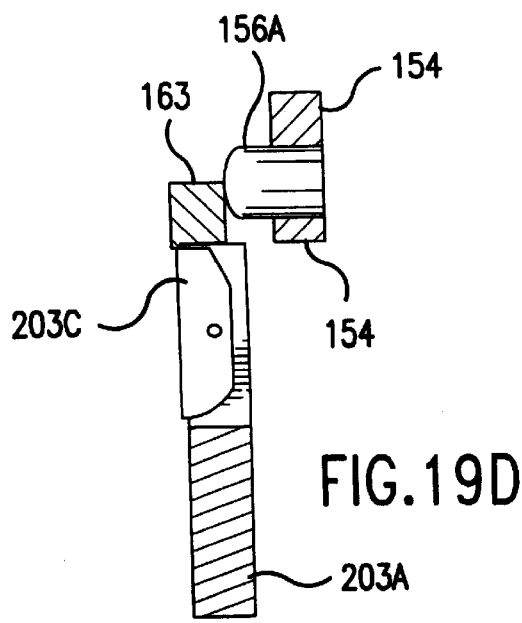
FIG.19D
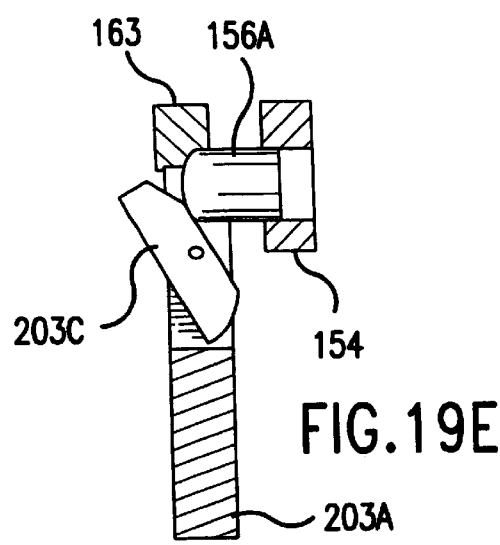
FIG.19E

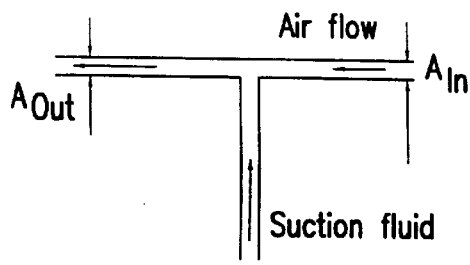

$A_{In} = A_{Out}$

Non-Educting Stream Tube
* Requires Reservoir Pressure
* Does not force suction fluid back

FIG.33A

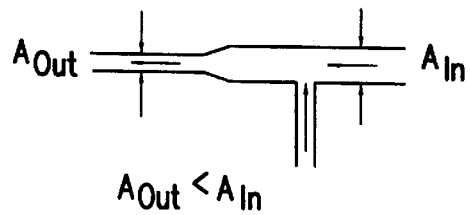

$A_{Out} < A_{In}$

Non-educting stream tube
* Requires reservoir pressure
* Will force fluid back into reservoir when reservoir pressure is removed, but air stream velocity is maintained

FIG.33B

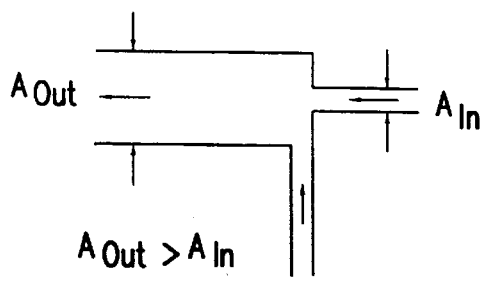

$A_{Out} > A_{In}$

Educting Stream Tube
* Does not require reservoir pressure to pull suction fluid
* Does not force fluid back into reservoir

FIG.33C

APPARATUS AND METHOD FOR DELIVERY OF MICRO AND SUBMICRO QUANTITIES OF MATERIALS

This application is a Continuation-In-Part (CIP) of Ser. No. 09/006,720 filed Jan. 14, 1998, now U.S. Pat. No. 5,997,518.

BACKGROUND OF THE INVENTION

1. Field of the Invention

This invention comprises a process and apparatus (device)f and the use thereof for delivering to a location of choice relatively precise, preselected quantities of a material, most preferably initially in the form of a mixture of a relatively larger quantity of gas and a relatively smaller quantity of liquid in the form of microdrops, submicrodrops or a single micrdrop to a location of choice. The liquid is preferably a drug and most preferably an ophthalmic drug. Alternatively, the mixture can be one of powder in such gas.

There is a need for a practical, patient-friendly system for delivering extremely small e.g. microliter and smaller volumes of medicaments accurately to parts of the mammalian body. This is especially the case in the field of ophthalmology. However, ordinarily a single drop of current ophthalmic preparations gravity-delivered by the patient contains far more volume than the preocular tear film can hold. The excess volume delivered is either drained via the nasolacrimal drainage system, making it available for undesired systemic absorption, or lost as waste over the eyelid margin. However, even though attempts have been made to develop reliable and practical small volume delivery systems for the ocular surface, these have all been unsuccessful.

2. Advantages of the Invention

In a preferred embodiment of the delivery system, the fluid initially prior to delivery exists as microdroplets of liquid in conveying gas, which microdroplets are conveyed as one form of microdroplet or another over a relatively small distance in the atmosphere. It has also been discovered as part of this invention that the viscosity of the liquid to be conveyed affects the physical form of the delivered liquid. Usually, the more viscous the fluid, the fewer the number of microdrops. Moreover the apparatus of this invention can be modified into a host of different embodiments so that any chosen embodiment according to the principles of the inventive concepts described herein will deliver liquid in the form desired to a target of choice.

3. Summary of Choices for Application of the Invention

It has been discovered and forms the core of this invention that the total amount of liquid micro droplets chosen to be delivered to a given location, (be it one relatively large droplet or a combination of relatively small droplets) is dependent on a certain preselected volume and pressure of gas which controls the velocity of working or delivering gas. Thus, first a choice is made as to the amount of fluid in a droplet or droplets is to be delivered to a location. Then an amount of gas and the velocity of delivery is chosen in accordance with the principles of this invention that will permit that amount of fluid in that physical droplet form to be so delivered. This relationship between chosen amount of delivery fluid (the conveying fluid such as gas that is delivered under pressure and entrains the liquid to be delivered) has been defined in mathematical relationships in novel and unobvious mathematical expressions that have been developed by the inventors and form a part of the invention as described herein.

In addition to the inventive process several apparatus embodiments have been developed as part of this overall invention. These embodiments are also sometimes referred to herein as devices and are novel and unobvious in themselves. In general, the devices employ novel and unobvious pump means. These are unobvious inventive modifications of eductor pumps or venturi configurations adapted to perform as a pump. The pump embodiments of this invention comprise physical entrainment means, as means for delivering a preselected quantity of liquid of choice to a preselected quantity of gas in a conduit moving with a preselected velocity to be delivered to a target, as for example as a microdrop or as microdroplets.

5. Preferred Aspects of the Invention

The present invention in its most preferred aspect concerns a system (process and apparatuses) for delivery of exceptionally small predetermined volumes (i.e. microvolumes or submicrovolumes) in the form of microdrops or a microdrop of liquid materials to the eye, nose or other parts of the animal, preferably the mammalian body, particularly the human species thereof under circumstances wherein the total amount received is preferably 1 to 10 microliters of liquid.

6. The Preferred Apparatus Has Particular Utility in Ophthalmic Applications

The preferred apparatus of the invention has particular utility in patient self-treating of his or her eye(s) with predetermined microvolumes if liquids that may incorporate micro quantities of drugs (total volume is preferably from 1 to 10 microliters) in a reproducible and reliable manner without uncomfortable eye impact and irrespective of patient blinking. The inventive apparatus can also be small enough to be easily handled by a patient.

7. The Invention Has Utility in Other than Ophthalmic Applications

The invention also has utility in other environments, where delivery of predetermined micro or submicro quantities, sch as microvolume drops or droplets is desired. Examples would include delivery of various components for microchip manufacture and other nonmedical applications. It can also be used in vetinarinary applications. The invention can be used under very high temperatures. Moreover, it is suitable for delivery of drugs and other materials in powder form. The impact power of the apparatus can be used to power various weapons and to propel liquid directly into an environment such as the skin. It can be successfully utilized where exceptionally small quantities of materials must be delivered on a site specific manner.

8. The Apparatus of the Invention Meets all the Criterial of Generally Accepted as Necessary for Patient-Friendliness By the Ophthalmic Discipline An especially preferred application of the process and apparatus of this invention is the delivery of micro or submicro quantities of drugs in a patient-friendly mode to the eye. In this environment, some very important medical criteria can be met by the invention. These criteria have been known to the art, but have not been achievable by any practical technique of the art. These criteria include:

1. delivery of the drug to the eye in total quantities of less than 30 ul
2. delivery of the drug to the eye in droplets of less than 20 ul and as small as (1) one nanoliter
3. delivery of the drug to the eye without excess force or impact to the eye.
4. delivery of the drug to the eye without any factors that would cause flinching, blinking or reflex tearing
5. delivery of the drug to the eye in a small delivered pattern of from 0.1 to 0.5 cm in diameter.

6. drugs for delivery are in small containers easily handled by patients
7. drugs for delivery are in a container that will deliver drug dosage accurately to the eye
8. There is little variability of the quantity of material that is delivered in subsequent sequences. (The term "drug" includes fluids, such as liquids, powders, gels and combinations thereof)
10. The invention overcomes the problem of delivery of excessive amounts of drug to the eye Thus, as will be discussed herein, excessive drug (more than 10 ul) in the eye is exceptionably undesirable. Mircopiptettes are known to deliver less than 30 ul quantities in single droplet form. Spray atomizers are known to deliver microliter droplets but in greater total liquid quantity than desired. Moreover, it is not known in the art how to design spray atomizers to deliver any of a preselected range of fluid quantities, especially in quantities less than 30 ul. Spray atomizers using either eductor pumps or direct liquid pressure are designed to deliver a gross and variable amount of spray in empirically determined and highly variable amounts, with no knowledge that there is a determinable correlation between the amount of fluid delivered and the amount of gas to entrain and transmit the fluid. They are also inherently flawed because of the high variability in the quantity of material delivered. It is very important that the same amount of drug be delivered on each sequential drug delivery step in the case of ophthalmic and other medical uses.

2. Related Art

The art has long recognized the need for a practical, patient-utilizable (patient-friendly) device for delivering microvolumes (often measured as microliters) of medicaments accurately to parts of the human body and by implication to other mammals. This is especially the case in the field of human ophthalmology.

The eye contains a preocular tear film to which medication may be applied. The current state of the art is such that the smallest single drop (20 to 50 ul) of ophthalmic preparations self-administered by a patient in a device of the present art delivers far more volume than such preocular tear film can hold. (An exception to this might appear to be the laboratory micropipette, but it is totally unsuitable for individual patient self-treatment, especially on a chronic basis.)

When such excess volume is delivered to the eye, it is either drained through the nasolacrimal drainage system or lost as waste over the eyelid margin. In the drainage mode, the excess may be made available to the body via systemic absorption by the body. This is generally undesirable and can produce serious side effects. Nevertheless, a reliable and practical microvolume or submicrovolume delivery system, easily, usable by patients (patient friendly) had not hitherto been developed before the instant invention. Moreover the apparatus of the invention is easily and inexpensively manufactured and relatively simple but elegant in design. It can also deliver repeatably uniform units of liquids or powders.

The lacrimal differences (both dynamic and correlatively pharmacokinetic) between large >30 ul) and small (<30 ul and as low as 5 ul) volumes of drugs instilled in the eye have been well characterized. Studies in rabbits have determined that the rate of drainage from the nasolacrimal; system is directly proportional to the instilled volume of liquid in the preocular tear film of the eye (Chrai et al., 1973).

The normal preocular tear volume is 6.8 to 7.9 or about 7.5 ul. Under highly controlled laboratory conditions permitting normal blinking, the preocular tear volume can be transiently expanded by another 10 ul without overflow (Chrai et al., 1973). Additionally, induced reflex blinking increases the rate of drug loss as the instilled volume increases. Larger volumes of liquid result in a greater rate of preocular drug loss. Increased instilled drug volume results in both increased drainage of drug via responses from reflex tearing, thus further diluting the drug with stimulated tears. This means the rate of drug loss actually increases as the volume of drug instilled increases (Chrai et al., 1974). Fractional ocular absorption also increases with decreasing instilled volume which is an inherent advantage of the instant invention.

Studies in rabbits using micropipettes to deliver ophthalmologically-active drugs suggest the desirability of delivering microvolumes or submicrovolumes to the eye in order to minimize systemic effects and maximize local ocular effects.

The most relevant devices known to the prior art that deliver micro quantities of fluid are International application numbers PCT/GB95/01482 and PCT/GB95/02040 both filed by R. P. Scherer Corporation The instant invention in contrast demonstrates that:
 a) A very small quantity (micro or submicro range) of material such as a liquid can be delivered by mixing it in an inventive manner with a conveying gas
 b) That the use of a select pressurized gas stream with a special means to reduce the pressure in a local area of space is a useful method for delivery of small volumes or quantities.
 c) That contolled gas entrainment is a useful method for the delivery of small quantities of liquids or powders.
 d) That the repeatability in terms of a repeatable quantity of materials of a gas entrainment delivery system is enhanced by increasing the head pressure.

International application number PCT/GB95/01482 filed by R. P. Scherer Corporation, is not a relevant teaching for the instant invention in that:
 e) it is a spray can with an internal bag to hold the liquid and does not use gas flow to control the delivery of the liquid.
 f) the metering is performed by controlling the time duration of the release of the fluid
 g) it does not teach any of the above points (a–d) that we teach.

International application number PCT/GB95/02040 filed by R. P. Scherer Corporation, is not a releant teaching for the instant invention in that
 h) it is a premeasured unit dose device
 i) it does not teach any of the above points that are important to the instant invention.

International application number PCT/GB96/03195 filed by R. P. Scherer Corporation teaches the use of a spray of fluid in gas in micro quantities. It is old in the art to use sprays as exemplified by Mistura™. It is old in the art to use microvolumes of drug in eye delivery. Applicants invention resides in the fact that once it is known that sprays of micro fluids are desirable for drug delivery, particularly in the eye, that they have developed a novel, unobvious and practical process for reliably delivering repeated uniform quantities and several apparatuses for effectuating such process. The inventive apparatus produces expceptionally small patterns of droplets smaller than patterns deposited from any such procedure produced by the process or apparatus of Scherer.

Studies in rabbits using micropipettes to deliver ophthalmologically-active drugs suggest the desirability of delivering micro quantities of liquid volumes to the eye in order to minimize undesirable local and systemic effects and maximize desired local ocular effects. Pilocarpine, a cholinergic parasympathomimetic agent that is used in the treatment of glaucoma, has ocular effects including constriction of the pupil and lowering of the intraocular pressure (IOP). Unwanted systemic effects of this drug may include intestinal spasm, broncho constriction, hypotension, and decreased heart rate.

Decreasing the dose of pilocarpine administered to the eye allows equivalent absorption of pilocarpine in the aqueous humor of the eye, lowering the IOP, but decreased pilocarpine concentration in the plasma of rabbits (Patton and Francoeur, 1978; Himmelstein et al., 1978). Other studies have confirmed the existence of this dose effect regarding medication delivered to the eye. For example, Patton found that decreasing the instilled volume to the eye actually increases the fraction of pilocarpine absorbed into the eye from the preocular tear film (Patton, 1977). This process of increased fractional ocular absorption is an inherent advantage of the microvolume instillation of the instant invention. Numerous studies in humans further support the desirability of decreasing the volume of liquid pharmaceuticals delivered to the eye. However no practical and reliable apparatus has hitherto been available for this purpose.

Smaller ocular volumes allow maintenance of the desired ocular therapeutic effects while decreasing or eliminating undesired systemic and local side effects. These smaller volumes have been administered using calibrated micropipettes as delivery devices. Using clonidine, an antihypertensive agent, Petursson et al., (1984) determined that instilling small volumes of 15 ul to the eye results in separation of the desired ocular hypotensive effects from the undesired systemic hypotensive effects and equivalent decreases in intraocular pressures as compared with larger volumes.

Other authors found that changing the volume of phenylephrine administered to the eye from 32 ul to 10 ul had the same beneficial effect (pupillary dilation), while markedly decreasing systemic absorption and side effects such as increased blood pressure (Brown et. al., 1986). A study in infants using phenylephrine demonstrated that a relatively small volume (8 ul) produced equivalent ocular effects and significantly lowered systemic blood levels of phenylephrine by 50% when compared to a 30 ul dose (Brown et al., 1987). A study with healthy adult volunteers found no enhancement of pupillary constriction with macrodrop (more than 30 ul) versus microdrop (less than 30 ul)volumes of pilocarpine (File and Patton, 1980) while minimizing undesirable side effects. These studies indicate the advantages of using small microliter volumes for ocular applications; however, the problem of reproducible administration of microvolumes of drug has not been addressed by the prior art, but has been solved by the instant invention.

While these several studies have demonstrated the benefits of using small microliter volumes of ophthalmic liquids, the mode of delivery (micropipettes) described is used extensively in laboratory studies, but is not suitable for self-administration by patients, because of their length and consequent difficulty in holding and directing accurately. Thus, no methods or devices have been described in the art or which are known to commerce which can accurately and reliably deliver microvolumes in a patient-friendly mode. Moreover, the apparatuses of the invention satisfy these criteria and others, including being reliable in terms of accurate delivery quantities and are easily manufactured. In addition, they are exceptionally user-friendly, as exemplified by the fact that they can be easily manipulated by non-medical persons and patients.

Current ophthalmic patient single-droplet-gravity driven delivery systems provide liquids as macrovolume quantities, which is defined as 30 ul and larger. These systems cannot reproducibly deliver smaller quantities nor is the delivery adequately controlled so as to comply with the criteria set forth above. Micropipettes are unduly long and cannot be controlled by a patient who is self-administering the drug.

No methods or apparatuses are known in commerce, which can accurately and reliably deliver micro or submicro liter volumes, are reliable and easily manufactured, and are easily manipulated by non-medical personnel and patients. The invention of this Application accomplishes those objectives. Current single-droplet-gravity-driven delivery systems use volumes on the order of 30 ul and larger because they cannot reliably deliver smaller dosage volumes. Volumes of 30 ul or more result in a large overdose to the eye with undesired local or systemic side effects as the excess drug is absorbed into the circulatory system as described in detail above reduce effectiveness and diminsh retention time on the ocular surface. The reflex tearing and blinking that accompanies instillation of macrodrops to the eye may cause significant dilution of drug and increased drainage of the drug. Reflex tearing may be in excess of 25 ul per min. Reduced retention time caused by the activation of reflux tearing and blinking may cause the drug to be washed out and drained from the ocular surface, thus reducing preocular residence time and ocular availability. Blinking that can accompany the instillation of a 30–50 ul drop in the eye enhances liquid entry into the nasolacrimal drainage system, thereby increasing the rate of drug loss from the preocular tear film and its availability for subsequent systemic absorption.

Current ophthalmic drug delivery devices also present a substantial problem in that the tip of the medicine dropper can easily come into contact with the eye or surrounding tissue. This creates a path for contaminants including microbes to travel between the delivery device and the eye. This is due in part to the fact that patients tend to hold their heads in an awkward position, thus making it more difficult for them to judge where the dispenser bottle is being held relative to the eye, often resulting in the tip touching the eye or ocular adnexa. In addition, contact between the dispenser tip and the eye or adnexa may result in clogging of the tip with lipids, proteins, or exogenous material such as components of make-up.

Conventional ophthalmic delivery devices typically deliver a single drop by gravity of about 30 ul or more. It is easy to accidentally squeeze the dropper bottle and deliver multiple drops with this dispenser, thus doubling or tripling the dosage with concomitant systemic absorption with local ocular side effects and waste.

For ophthalmic drugs to be effective, they must be delivered with reasonable reliability to the eye. With current ocular drug delivery systems, it is possible for a patient to miss the eye completely, for example by depositing the drug on the eyelid, and to assume that the drug has been properly delivered. Thus, lack of efficacy may also be related to the shortcomings of the delivery system.

The instillation of too large a volume of liquid, 30 ul or more, to the eye may result in a number of phenomena such as described above that reduce the efficiency of drug pharmacokinetics. For example, reflex tearing results in dilution of the delivered volume, and enhances drainage into the nasolacrimal drainage system. Reflex blinking as a result of macrodrop delivery accentuates the reduction in preocular residence time, and enhances drainage through the nasolacrimal drainage system and increases the opportunity for undesired systemic absorption. Use of macrodrops may further cause discomfort, such as burning and stinging, to the user. Thus, the ability to consistently and reliably deliver volumes of liquid medicaments as small as 1 microliter, preferably 1 to 5 microliters or smaller is a desirable goal, that is achievable by the present invention.

SUMMARY OF THE INVENTION

The present invention overcomes the drawbacks and disadvantages inherent in the described prior art by providing in a preferred embodiment in a patient-friendly manner a predetermined micro or submicro volume quantity of a drug to an eye in a reliable and reproducible manner. This has the extremely beneficial effect of maximizing desired local therapeutic effects and minimizes undesirable local and systemic effects from excessive drug being delivered to the body, such as through the nasolacrimal drainage system of the eye.

In general, the invention utilizes a gas stream under pressure to entrain a predetermined quantity of a liquid or powder and to deliver either or both in micro or submicro volume quantities to a desired site, such as an eye (human or animal).

A particular advantage of the invention is to effectuate delivery of such liquids or powder in extremely small quantities (i.e. droplets of less than 10 ul). These delivered droplets are much smaller than the drops from a conventional eye dropper. The volume or three dimensional size of the droplets of the invention is generally from 0.1 up to but less than 30 ul, but it is preferably 1 to less than 10 ul and most preferably 0.1 to 5 ul.

It is believed that the linear size or diameter of some of the droplets of the invention when spherical is generally from 1 up to less than 100 microns, but is preferably 1 to 20 microns, especially preferably 1–15 microns and most preferably about 8 to 12 microns. It is expected that diameters of some of the droplets of the invention can be calculated using the equation $V=4\pi r^3$ where the diameter=2r.

Conventional bottle dropper systems are used by patients and are designed to deliver a single macrodrops (30–50 ul) to the open eye. As discussed above, it has long been known that micropipettes, (ordinarily usable only for laboratory experiments and not practical for individual patient use) can deliver much smaller gravity-driven single microdrop (1.5–10 ul) quantities or amounts to the open eye by actually contacting the eyes tear film and are not typically gravity driven. Bottle dropper drops (30 to 50 ul), because of the delivery and impact effect of such size, cause soft trauma (reflex stimulation of tearing, blinking and wiping, etc. ) to the eye due to the impact of the single large droplet. It is expected that the action of the very low quantity of drugs capable of being accurately delivered by the present invention may result in more rapid and complete mixing of a drug so delivered with the ocular tear film Previous techniques have been proposed for delivering small volumes or quantities of liquids to the eye (8–11 ul). One such technique involves an eye dropper stated to produce a small volume drop of 11 ul (Brown et al., 1985). Eye dropper application is slow and inherently delivers large quantities of liquid. Another technique involves direct ejection of liquid into the eye via pressurized gas (gas propulsion) (U.S. Pat. No. 3,934,585). However, both of these techniques of the art present serious difficulties.

The direct ejection technique requires the use of gas which is pressurized in order to propel the ejected liquid (but in undesirable large quantities) with sufficient velocity to reach the eye. However, the direct ejection technique causes ejection of at least some of the liquid before the gas which propels this liquid has reached a velocity sufficient to propel this liquid a sufficient distance to reach the ocular surface of the eye. In addition, the direct ejection technique causes an audible pop or snap as the liquid is ejected, resulting in a reflex blinking and the potential for consequent misdirection of the liquid.

The dynamic processes involved in creating and delivering a desired microliter or even submicro quantities of desired liquids, such as a drop with an eye dropper are often overlooked. Problems with surface tension and adhesive forces between the drop and eye dropper tip make the eye dropper technique inconsistent, unreliable, unwieldy and thus uncontrolled.

One method of calculating the mass of a typical drop (not desirably small) delivered from a device such as an eyedropper is to equate the gravitational forces on the drop with the surface tension of the fluid around the perimeter of the nozzle using Tate's law:

$$m = \frac{\tau \pi d}{g} \qquad (1)$$

where m is the mass of the eye drop, d is the diameter of the delivery tube, $\tau$ is the surface tension of the fluid in question, and g is the acceleration due to gravity (Brown et al., 1985). This equation suggests that reducing d, the diameter of the dropper tip, will consistently reduce the mass of the drop delivered.

Using surface tension for atypical aqueous ophthalmic preparation with the density of water and $\tau$=0.04N/m, a 1 mm diameter tip would produce a 13 ug (13 ul if the density of the preparation is that of water) drop size. Using the correction factors determined by Harkins and Brown assuming (see ref. A) we calculate that the actual drop volume delivered would be closer to 9 ul.

For the purpose of ophthalmic delivery, there are significant problems overlooked by this approach. Because the separation of a drop from the tip of an eye dropper is a dynamic process, (See ref B. Chattoraj and Birdi pp. 24–25) factors such as the rate or time of drop formation and the surface adhesion to the dropper tip, drop shape, as well as the immediate formation and separation of another drop following the first drop, and of course gravity, are all important factors that affect the reliable formation and delivery of a small volume drop. Harkins and Brown (ref. A) noted that for benzene which has a surface tension of about 0.028N/m, tip diameters smaller than 1.5 mm in radius caused the fluid to creep up the outside of the tube. Thus the reduction of drop volume size simply by the reduction of tube diameter as suggested in equation (1) is not likely to give satisfactory results for dispensing ophthalmic preparations in a simple user-friendly manner.

Adhesion forces between the drop and dropper tip prevent the drop from falling from the tip by the force of gravity alone. Equation (1) is assumed to define a break-point at which the drop separates from the tip of the dropper under the influence of gravity. The empirical evidence described in the Brown et al. (1985) publication regarding the tendency of a microdrop (8 microliters to 11 microliters) to stick to the end of a dropper suggests that equation (1) may not be an adequate explanation of the actual occurrence A better way to understand the process of separation of a drop from the tip of a dropper is to consider the relative forces governing the drop dynamics. This approach helps to provide the simplest possible picture, while avoiding the introduction of variables such as dropper tip diameter and tip material of construction. It also provides an accurate estimate of the smallest drop size that can be reliably delivered from the tip of a dropper under the influence of gravity. The conventional dropper bottles are designed so that the internal pressure in the bottle has little effect on the drop delivery other than to slowly force the fluid out to the tip of the dropper. The relative importance of the surface tension forces compared with the gravitational force may be considered by comparing the drop diameter with the capillary constant for water. According to Landau et al. (1987), the capillary constant for a fluid (a) may be calculated using the formula:

$$a = \sqrt{\frac{2\tau}{\rho g}} \quad (2)$$

wherein p is the mass density of the fluid, $\tau$ is the surface tension of the fluid, and g is the acceleration due to gravity. The units of a are length, and, if the characteristic length dimension (such as the diameter of a spherical drop) of the unit of fluid in question is small compared with a, then the surface tension forces dominate the gravitational forces in the determination of the shape of the unit of fluid.

For water, $\tau$ is about 0.072N/m at 20 degrees C. in contact with air. The corresponding capillary constant for water in air is 0.39 cm. The capillary constant for the typical ophthalmic preparation is about 0.29 cm. The diameter of a 30 ul spherical drop is 0.39 cm, i.e., the same as the capillary constant for water. A 12 ul spherical drop of water is about 0.29 cm in diameter and a 1 ul drop is about 0.12 cm in diameter. These computations strongly suggest that surface tension forces will dominate in the delivery of a drop of under 10 ul of liquid that have densities and surface tension forces approaching those of a typical ophthalmic preparation.

Precise calculations involving the dynamics of a drop on the tip of a dropper are exceptionally complex. However, since current eyedroppers operate ideally with gravity, surface tension, and surface adhesion as the only major forces for shaping and separating the drop from the tip of the dropper, surface tension for 10 ul or smaller volumes is the dominating force, making gravity delivery of small volume drops impractical.

The separation process of the drop from the tip of a conventional dropper is actually a fluid-fluid separation and not the fluid separating from the tip material of the dropper. What is observed is that the large drop forms a narrow "waist" in the fluid just distal to the tip of the dropper, and the waist becomes progressively narrower until the fluid below the waist separates. This creates an instability which can only be reliably induced when the characteristic dimension of the fluid volume to be delivered becomes greater than the capillary constant of the fluid, and at this point, the fluid separates from the rest of the fluid and becomes a separated drop. The remaining fluid on the tip spreads out as a thin layer over the tip of the dropper.

These empirical observations suggests that the drop separation occurs when the mass of the drop is sufficiently large that the drop shape changes significantly under the influence of gravity, and provides relatively reproducible drop sizes somewhat larger than the capillary constant in diameter. Drops that are too small to form this waist under the influence of gravity, i.e. drops that are smaller in diameter than the capillary constant, will not separate as easily from the tip of the dropper with gravity as the only separating force, and in the presence of contaminants such as oils are more likely to wick up the outside surface of the dropper. These factors, along with the difficulty of control for delivering a single drop make gravity delivery of volumes, such as drops, smaller than 10 $\mu$l of ophthalmic preparation difficult and not user-friendly.

This invention preferably for medical uses employs a gas such as air, $N_2$, $CO_2$, or any other gas, which is inert and medically safe for medical applications, to induce the delivery of a measured amount of fluid, often aqueous, to the eye. Other gases such as hydrocarbons can be used in nonmedical applications. There are several inventive embodiments for this technique, but two method embodiments are described to demonstrate the concept.

The first method is a single step induction or entrainment method specifically modified in an unobvious way. The single step method uses a motive gas for metering and delivering a small predetermined quantity of fluid to the eye or other target of choice. The volume of liquid delivered to the eye and any other target for that matter is controlled by the volume and pressure and thus velocity of the motive gas.

The second method is a two step induction method. In this method the desired volume of fluid is pre-metered into a passage or compartment by either capillary action or by a mechanical action that pushes the fluid into the compartment. The motive or propulsive gas is forced through the compartment to mix and eject the fluid through a nozzle to the eye. A capillary tube can be used to effectuate the capillary embodiment.

Several apparatus embodiments are described which are primarily multiple dose delivery devices, although they are also capable of operating as unit dose devices. These embodiments implement the overall process of the use of the inventive modified gas entrainment of materials such as liquids taught by the present invention—i.e., the movement of a measured volume of gas to separate, entrain and deliver small preselected volumes of fluid to the eye or other sites.

The especially preferred embodiments shown use a piston and spring for the creation of a transient high pressure air pulse of a predetermined quantity of a material such as a liquid or powder. In this manner repeated pulses with concomitant repeated volumes of fluid of relative consistency will be delivered It will be appreciated, however, that the air pulse may be generated in a variety of ways, and that other gas sources such as pre-pressurized cartridges or canisters of $CO_2$, $N_2$ or other non-toxic, preferably non-flammable gases in medical applications may be used in conjunction with appropriate valving schemes.

An inventive single step induction (entrainment)system is illustrated in FIG. 1. This system employs a measured amount of gas delivered at a given pressure to induce a measured volume of fluid to be pulled into the mixing stream of the inventive pump that becomes mixed with a propulsive gas, preferably an air stream, and then is ejected from an exit nozzle.

FIG. 1, FIG. 2, FIG. 3, and FIG. 4 show the principal components of one inventive gas induction delivery system using either a eductor pump or a pump resulting from the modification of a venturi configuration as well as a r paddle wheel include examples of those embodiments included within the scope of the invention.

The principal components of a preferred inventive apparatus are: a main body or housing which houses a spring, piston, release mechanism and cocking mechanism for compressing a plunger-driving-spring, and air and material reservoirs, and a suitable pump means including an inventive eductor and a venturi modified to be a pump. The body 10 in one preferred embodiment is typically about ¾" to 1" in diameter and about 1" to 3" long.

The present invention will deliver exceptionally small dosage drug volumes i.e. submicrovolumes or preferably microvolumes totaling from 1 to 10 ul total dosage to the open eye with no soft trauma effects and without the necessity for consideration of the influence of spontaneous or reflex blinking of the eye. When at the viscosity of an aqueous solution, the drug microvolume total dosage is often comprised of a multitude of much smaller ultramicro drops in the form of a spray wherein said ultramicro drops are in the range of 1 to 100 microns in diameter.

When liquids of considerably higher viscosity than pure aqueous are employed in some of the preferred apparatuses of the invention, the micro or submicro quantity delivered will often be a substantially unitary droplet comprised of no more than about five fragments. Such liquids delivered in this form are novel and unobvious in and of themselves.

In a preferred embodiment, the present invention seeks to address and overcome the many drawbacks inherent in the prior art by providing an ideal small quantity of drug delivery to the eye in order to maximize desired local therapeutic effects and minimize local systemic undesirable side effects. In particular, the system employs a gas stream to entrain (induce) a controlled volume of a liquid into the gas stream and to deliver the liquid preferably in the form of a small drop of from 1 nanoliter to 5 ul) or alternatively in the form of even a greater quantity exceptionally small droplets to a desired site such as an eye. Of particular interest is the ability of the system to deliver small quantities (i.e., less than about 10 ul) of a relatively viscous liquid as essentially single droplets. These droplets are much smaller in size than a conventional gravity driven drop of the liquid.

In one embodiment, the size of a given drop may be generally the size such as is found in an aerosol or mist which may be in the micron range, e.g., 1–5 microns, 10 microns or larger, up to 100 microns, preferably in the range of 10 microns. The diameter of the drops can be calculated using the equation $V=4\pi r^3/3$ where the diameter=2r.

Current gravity driven drop dispensers are inadequate for small quantity delivery, and cannot be made to reliably deliver small micro or submicroliter volumes of which the instant invention is capable. Although small microliter volumes of ophthalmic liquids can be delivered by micropipette, this technique is suitable only for laboratory studies, and is not suitable for self-administration by patients for many reasons, some of which are discussed elsewhere herein.

In one general aspect the present invention provides a system/apparatus, which is patient-freindly, for delivering commonly-used ophthalmic fluids in quantities smaller than amounts delivered through conventional means excluding micropipettes). The smaller quantities are especially designed to remain within the capacity of the eye to hold such quantities. Exemplary uses that would benefit from administration by the disclosed system include cholinergic agonists, alpha-adrenergic agonists, beta-adrenergic receptor antagonists, mydriatic, cycloplegics, corticosteroids, and prostaglandins. Cholinergic agonists, such as pilocarpine, affect the autonomic effector cells innervated by parasympathetic nerves. Pilocarpine's clinical use is restricted in ophthalmic application to induce miosis (pupillary constriction) and decrease the intraocular pressure (IOP). Systemic side effects of pilocarpine may include increased tone and motility of the smooth muscle of the intestine, stimulation of the bronchial smooth muscle resulting in asthmatic attacks, and a marked fall in blood pressure and heart rate. Beta-blockers, such as timolol, block the beta adrenergic receptors in the sympathetic effector system. Timolol is used ophthalmologically to decrease IOP in patients with glaucoma. It may be extensively absorbed systemically after topical administration and result in adverse systemic effects such as decreased blood pressure, decreased heart rate, and broncho constriction, and may mask hypoglycemia in patients with diabetes. Clonidine is an alpha-adrenergic agonist that is used as a topical ophthalmic hypotensive agent. Potential side effects of this class of drugs include hypotension, sedation, fatigue bardycardia, and dry nose and/or mouth.

The present invention employs gas entrainment (induction) in an unobvious inventive manner to deliver small and accurate volumes of liquid in a reproducible and reliable manner. The system does not rely on gravity to separate or propel the liquid for delivery. It relies instead on a preselected volume and pressure of gas to both separate and deliver a preselected quantity of a material such as a liquid. The ratio of motive gas used to liquid delivered is preset as is the pressure of the gas. The invention eliminates the problems encountered in droppers which involve adhesion forces including surface tension at the tip diameter, difficulties in use, lack of control of quantities (very small), and contamination.

In its preferred embodiment, the present invention employs a specially adapted embodiment of the gas eduction principle to deliver predetermined quantities of liquids as micro or submicro size drops to a selected target. An advantage of the invention is that such liquids can be delivered repeatedly to such target, preferably an eye in a reproducible and reliable manner.

Unlike a conventional gravity-driven eye-dropper delivery system the invention does not rely on gravity for delivery of a material to a target, such as an eye. Moreover, the invention delivers very much smaller quantities of liquid to such a target than is possible with a conventional eye dropper. The technique of the invention relies on utilizing a preselected volume of gas to entrain a preselected micro or submicro volume or quantity of a liquid and deliver such liquid to a target, such as an eye.

Accordingly, this invention presents the advantage of eliminating the problems encountered in conventional gravity driven eye droppers, which must overcome the effects of large unwanted adhesion forces from such factors as surface tension attractions at the tip, too large a tip diameter, difficulties in use, lack of control of quantities, clogging and contamination.

In its preferred embodiment the mixture initially exists as micro or submicro droplets of liquid in gas, which micro or submicro droplets are conveyed over a relatively small distance say up to three inches in the atmosphere.

The volume and velocity of the delivering gas is dependent on the pressure head on the gas at the moment it, in a preferred embodiment, is compressed and then commences its transposition through the apparatus of the invention. In such conveyance the pressure gradually diminishes. The invention requires that at the exit orifice of the apparatus sufficient pressure remains to provide velocity for extraction of the liquid from the reservoir, which has been removed therefrom and will be expelled from the apparatus of the invention.

The pressure needed in preferred embodiments is approximately 7 to 1000 pounds per square inch for the eductor embodiment of this invention. The modified venturi embodiment of this invention can use lower pressures say from 1 to 100 pounds per square inch. Virtually none of this pressure is transmitted to the eye nor perceived by it. This accounts for the high utility of this invention in the environment ocular administration.

Thus, first a choice is made as to the amount of material such as fluid in the form of one or more micro or submicro droplets to be delivered to a location. And an amount of gas and the velocity of delivery provided by a certain pressure head is chosen in accordance with the principles of this invention that will permit that amount of fluid and the form of the droplets containing said fluid to be so delivered. This relationship between chosen amount of delivery fluid has been defined in mathematical relationships in novel and unobvious mathematical expressions that have been developed by the inventors and form a part of the invention as described herein. These formulas provide a quantitative control aspect to this invention not previously available.

In addition to the inventive process several apparatus embodiments have been developed as part of this overall invention. These embodiments are also sometimes referred to herein as devices and are novel and unobvious in themselves. In general, the devices employ pump means developed by the inventors for achieving the purposes of this invention. These pumps are subelements and are referred to herein as stream tube pump means. These provide for release of just the desired amount of fluid from the reservoir, overcoming the attractive forces thereof and achieving physical entrainment of such extracted liquid as means for delivering a preselected quantity of fluid of choice to a preselected quantity of gas in a conduit moving with a preselected velocity.

Once the liquid is entrained in the delivery gas, it mixes to a greater or lesser extent (depending on whether the inventive eductor modification or inventive venturi modification is employed) with such gas depending on viscosities and velocities and the like of the working gas.

An especially preferred application of the process and apparatus of this invention is the delivery of materials such as drugs to the eye. In this environment some very important medical criteria can be met by the invention. These criteria have been known to the art, but have not been achievable by any practical technique of the art and have been desired for a long time.

Thus, as has been discussed above, excessive drug volume (more than 30 ul) to the eye is exceptionally undesirable. Micropipettes are known to deliver less than 30 ul as low as 1.5 ul quantities in single droplet form but they are not useable for self-administration of drugs. Spray atomizers are known to deliver droplets to the eye, but in far greater quantities or amounts than desired. Moreover it is not known in the art how to design spray atomizers to deliver any of a desired preselected range of exceptionally small fluid quantities, especially in quantities less than 30 ul in a predictable reliable manner with low variability.

Perfume spray atomizers of the art are designed to deliver a gross and highly variable and thus unreliable amounts of spray in empirically determined gross amounts far exceeding microliter quantities with no knowledge by the manufacturer that there is a determinable correlation between the amount of fluid delivered, the amount of gas to entrain and transmit the fluid and the pressure of the gas. Indeed, empirical measurements were made by the inventors of commercially available perfume atomizers utilizing conduits of size comparable to the especially preferred conduits utilized by Applicants invention. The pressures of the gas generated by the bulbs of such atomizers range from about 1 to about 5 pounds maximum of pressure per square foot of air above atmospheric pressure. This amount of pressure is greatly variable and depends on the way the bulb is squeezed with the fingers. Five pounds per square foot pressure is rarely achieved and generally requires a prodigious squeeze.

Thus, the capriciousness in the delivery amounts alone makes the spray atomizers unusable for a drug delivery system.

In contrast the preferred eductor embodiment of this invention utilizes a pressure range of seven (7) to one thousand (1000) pounds per square inch. Thus the pressure differences in the devices of the art and that of the current invention are quite profound. Generally the preferred pressures will be more than 5 and preferably 7 or more pounds per square inch.

Moreover, the bulb, which must be squeezed to deliver droplets of perfume or the like with atomizers contains a considerably greater volume of gas than used in the preferred apparatus of the invention. Such large quantities of gas result in sprays with relatively huge quantities of sprayed liquid in very large spray patterns. This is diametrically opposed contrast to the controlled ultra small, indeed micro or submicro quantities of liquid provided by the apparatus of the invention with small defined patterns of delivery. Moreover the spray pattern of a perfume atomizer is generally greater than about two (2) inches in diameter and is therefore unsuitable for the preferred prime uses of the apparatuses of the invention which are for controlled application of extremely small quantities of drugs to the eye in less than two inch diameter patterns.

The present invention employs various pump means embodiments and features, which can be utilized as subcombination elements, all of which operate in response to the flow of a gas. Static forces generally hold the liquid in place and no liquid is ejected until a threshold velocity of the gas is reached. Once the threshold velocity is reached, liquid is entrained into the gas stream and ejected as a drop or droplets at sufficient velocity to reach the eye or other body part. The velocity is kept below that which might be harmful or cause discomfort or reflex tearing or blinking.

Liquid entrainment by gas to deliver micro or submicro liter quantities, as demonstrated by the present invention is superior to direct propulsion or direct ejection of a liquid in two very important ways. First, the apparatus of the present invention using gas induction or gas entrainment is often less complicated than many direct propulsion devices. The gas entrainment subelement involves no small moving parts and the delivery and metering of gas may be performed with a piston and requires no complicated valving. A cylinder of gas under pressure may also be used as a gas propulsion source.

Second, and perhaps more importantly, with the gas entrainment device of the invention ( induction by means of eductor pump or modified venturi pump device), the liquid is not ejected until the gas flow reaches a certain predetermined velocity as set by various criteria determined by processes which constitute one aspect of the invention. This means that the inventive device can bring the gas ejected up to appropriate velocity before liquid will be ejected with no abrupt audible pop, snap or other noise. This is extremely important in ophthalmic applications, since experience shows that a sharp audible noise such as a pop or snap will cause the user to blink and impede the delivery of the liquid to the eye.

In one broad aspect the invention resides in a delivery apparatus, which produces a gas stream of a consistent predetermined volume and a consistent predetermined velocity under a preselected pressure; a liquid container as a reservoir, a gas container as a reservoir; a discharge conduit to deliver a gas stream from the apparatus, which includes a section to manage the gas stream and reduce its static pressure; and a liquid entrainment means that is pump means, such as a modified induction pump or other suitable liquid entraiment means, to draw a predetermined amount of liquid from the liquid container into the reduced pressure section for mixing with and delivery by the gas stream containing liquid through the discharge orifice or conduit to an eye or other chosen target.

The gas container is an important feature in that it provides a repeatable pressure and therefore a repeatable volume of gas under such repeatable pressure. The gas container also includes a releasable gas pressurization device and a mechanism for activating release of the pressurizing device.

In one embodiment, the gas container comprises a cylinder closed at the top and fitted with a piston capable of compressing gas upon moving toward such top. Optionally, the piston may have a one-way valve, so that gas is not drawn through the pump as the piston is drawn into the cocked position where the spring is compressed the desired amount. (It has been found for the preferred embodiment that the spring is preferably not compressed to its maximum nor is it released to its maximum.) The piston is connected at its lower end to a cocking member, which allows the piston to be fixed at its lower travel movement location and then released.

Thus, ideally, the spring is partially compressed when the piston is at the top of its travel, and when the piston is drawn into the cocked position, it does not compress the spring to its full extent. This is because the force of the spring changes as the spring is compressed. Therefore, the fractional change in the force of the spring is less if the spring is moved from one partially compressed displacement to another partially compressed displacement, than it would if the spring were uncompressed when the piston was at the top of the cylinder, and fully compressed when it was at the bottom of the cylinder.

In one embodiment, the cocking member takes the form of at least one spring-loaded lug or other catches which are attached at their inner ends indirectly to the piston and spring outwardly at their other ends to engage suitable recesses in the cylinder wall or other suitable hold members. The piston is capable of being moved by means of a spring interposed between the piston and a fixed position in the bottom of the apparatus. A stop pin inserted in the piston and engaged by a twist ring is used to hold the piston in the cocked position. Thus, the piston may be moved downwardly within the cylinder, thereby compressing the spring until the piston reaches its cocked position. A mechanism is actuated to release the pin, when desired, thereby allowing the spring to drive the piston upward and compress gas above the piston.

Several preferred apparatus embodiments are disclosed. There are many possibilities for inducing (entraining) liquid into the ejection pathway by means of a gas at a pressure and velocity, which will cause liquid to emerge from its reservoir through tapping or other conduit means based on mechanical interaction with the reservoir liquid. These liquid reservoir inducing means include inventive eductor pumps, modified venturi nozzles (both of which act as pumping means), and metering or paddle wheels. For the purposes of this invention, each of the above is considered a type of pump, and within the scope of pump means to help induce a liquid into an entraining gas stream for delivery as a drop or droplets to the eye or other selected targets. Thus any or all of the above described pump devices are generically referred to herein as pump means.

In one embodiment, a pump is positioned above the cylinder, and receives compressed gas from the cylinder through a suitable gas passageway. The pump is also connected by a suitable conduit to a reservoir of a liquid drug or other medicament, such that gas passing through the pump draws the liquid from the reservoir by creating a reduced pressure zone, mixes with it, and discharges the liquid as micro or submicro droplets. Optionally a selected pressure through a suitable first conduit means can be applied to the liquid reservoir to facilitate the removal of liquid therefrom by means of a second conduit means. This greatly enhances the flexibility of operations. Thus, effective entrainment and conveyance of relatively high viscosity liquids, mixing ratios, self cleaning, consistent liquid delivery quantities and the like are variables that can be controlled through such pressurization and other modifications as are described herein. The pressurization feature is especially preferred.

The apparatus of the invention delivers low micro or submicro volumes of both liquid and gas with the very desirable characteristic of low variability. The apparatus is capable of delivering small volumes of liquid on the order of 1 nanoliter to 25 ul consistently. Previous devices, such as eye droppers have failed to deliver such small volumes accurately and consistently; they have delivered volumes on the order of 30 ul or more The present device, in contrast, is able to deliver quantities (consistent with selected gas velocities) of far less than 30 ul, say 1 nanoliter to 10 ul.

Instead of extracting many units from a reservoir of liquid, a preselected quantity of liquid to be entrained or inducted may be pre-metered into a chamber. The chamber containing the preselected quantity of such liquid may be connected by a conduit to the gas stream in a pump means. The preselected volume may be inducted and delivered by the gas stream when it has reached the preselected velocity. For instance a capillary tube holding a fixed amount of liquid for each delivery cycle can be employed as a form of chamber.

It is also envisioned that the device of this invention may be modified to deliver one or more unit doses. For the purposes of this invention a unit dose is defined as a volume of a liquid contained in a disposable container. Said container is typically sealed and contains liquid without preservatives added.

The apparatus of the invention may be modified in many respects. Thus, the pump may take the form of a eductor a modified venturi, or a paddle wheel. The gas compression source may also take the form of a small cylinder of compressed gas available commercially such as a $CO_2$ cartridge connected through a suitable quick discharge valve to the pump.

A preferred embodiment of the invention is one that is small enough to be held in one hand and carried on one's person. The overall shape may be cylindrical, rectangular, square or molded to fit the hand and may be about 1 to about 6, preferably 3 inches long and about 0.5 to about 2, preferably 1.5 inches in diameter. It may weigh about 1 to about 16 preferably about 12 ounces.

The specially preferred apparatus feature of this invention, which embodies the process of the invention is a remarkable device for the ophthalmic field. The inventors have provided for the first time a device that can simultaneously provide in a cost effective and practical manner all of the features deemed desirable for a patient-friendly delivery device for conveying drugs to an eye. (Concomitantly the principles of the invention are clearly adaptable for utilization in a multitude of other fields both medical and nonmedical)

The core of the inventive process is the development of a device which permits extremely small quantities of materials to be delivered (as low as 1 nanoliter to less than 10 microliters of liquid and more if desired). The invention permits ophthalomogical drugs to be delivered to the human eye in a patient-friendly manner. The inventive process requires making a series of selections from a variety of physical parameters. These factors selected are all interrelated with and interact with each other as follows:

The first selection is the quantity of material such as a liquid (drug) desired to be delivered to a target such as the human eye.

The second selection is the quantity i.e. volume of gas necessary to entrain and convey such material, i.e. liquid to a selected target, (ordinary air and other gases even more inert can be used).

The third selection is the pressure under which such gas needs to be placed in order to achieve the desired velocity necessary for both conveying such gas past a reservoir containing liquid to be delivered and also having sufficient velocity after entraining (inducing) the desired quantity of liquid to convey such liquid to the selected target, The fourth selection is the gas/liquid entrainment (induction) mode by which the proper quantity of liquid is placed in the gas stream. The two modes that have been found to be most effective are the eductor pump mode and an inventinve modification of a venturi called a modified venturi to result in a pump. Both modifications have been invented by the inventors hereof and form important features of this invention.

The fifth selection is the dimensions of the device within which the patient-friendly process of the invention can be achieved. The device must be relatively small, say occupying from 0.20 to 20, most preferably 3 to 10 cubic inches. It can be any shape but it is preferred that it be cylindrical.

The sixth selection is the means for gas propulsion. It can be a spring powered piston for compressing the gas and forcing it through a conduit. It can be an exterior source of gas under pressure such as from a $CO_2$ cartridge The seventh selection is the cross-sectional size of the conduits that are used to convey the propelling gas through a pump system, where it entrains a desired preselected amount of liquid and then to the outside of the device.

The eighth selection is the cross-sectional diameter and length of the conduits that are needed to convey a preselected amount of liquid to the conveying gas.

The ninth selection is the location and design of a reservoir for material (liquid or powder) within or without the device for the material source.

The tenth selection is the location and design of a reservoir for the gas propulsion source either within or without the main body of the device.

The eleventh selection is the location and configuration of the conduits referred to above within the main body of the container The twelfth selection is the release mode that initiates the sequence of events commencing with the pressurized gas flowing through a conduit on the way to one of the pumping means mentioned above.

The thirteenth selection is optional. It involves providing in the modified venturi mode valving means for reducing pressure on the liquid reservoir at an appropriate point in the inventive sequence thereby permitting both means for achieving the predetermined liquid to be entrained as well as allowing gas free of liquid to exit from the container to purge the exit orifice of any residual liquid so as to avoid residual material such as liquid for the next delivery cycle.

The fourteenth selection is that which involves the type of mixing of material in the pump means with respect to the formation of a about a single drop to formation of many even smaller droplets.

The fifteenth selection is the ratio of gas to liquid the mixing ratio which must be predetermined in accordance with the amount of material desired to be delivered. It is in the range of the ratio of 3000 to 1000 to 1 by volume. The relative size of the conduits relates to the determination to the amount of gas to be used to achieve delivery of a given quantity of liquid.

The sixteenth selection is the pitch of the helix of the twist ring. The pitch must be sufficient that the spring can be compressed the desired amount without an unreasonable amount of turning. Furthermore, the pitch must not be so great that the twist ring is hard to turn. In the most preferred embodiment the use of ½ to 1 full turn to fully compress the spring provides a typical range for the twist ring. The vertical displacement of the piston from this twist is typically 0.1" to 0.3".

The seventeenth selection is that the material reservoir size must be selected relative to the total amount of conveyed air used. The reservoir size must not be so large that the reservoir cannot be sufficiently pressurized by the action of the piston to provide reasonably accurate delivery. In some cases, some empty space above the reservoir material is desirable to prevent the change in volume from the evacuation of the material from the reservoir from changing the delivery of the material. For 1 ml of total air displacement, the reservoir volume should be in the range of 1 to 5 ml.

The eighteenth selection is to choose the length of the feeder tube for the pump. If a fixed amount of fluid is desired, with a very low variability, then a longer feeder tube is desired.

If it is important that the average mixing ratio remain constant over a wide range of selected volumes to be delivered, then the feeder tube should be short. Typically, a long feeder tube can be 2 or more inches long, while a short feeder tube may be ¾" or less in length.

The nineteenth selection is the overall size of the device. The device must typically fit in the palm of one hand. It must also be light enough that it can be easily manipulated so that the device can be aimed accurately and the material can be delivered to the desired area.

The gas container or reservoir is an important feature in that it pressurizes a repeatable volume of gas to a repeatable pressure and volume. The gas container also includes a releasable gas pressurization device and a mechanism for activating release of the pressurizing device.

BRIEF DESCRIPTION OF THE DRAWINGS

FIG. 4A is a schematic, expanded view of one-side of the inner wall surface of the twist ring or sleeve with a latch pin shown in FIG. 1.

FIG. 4B is a schematic, bottom view of the twist ring or sleeve shown in FIG. 1.

FIG. 4C are schematic, top and side views of a device to release the piston shown in FIG. 1.

FIG. 4D is a schematic, enlarged view of an elongated button or rod shown in FIG. 1.

FIG. 5 is a schematic, side section view of an eductor pump shown in FIG. 1.

FIG. 19 Button Ring

FIG. 33 Types of Stream Tubes

DESCRIPTION OF ILLUSTRATIVE EMBODIMENTS

Two techniques of the art have been proposed for delivering small volumes of liquids to the eye. One such technique involves an eye dropper stated to produce a small volume drop of 8 to 11 ul (Brown et al., 1985). Another technique involves direct ejection of liquid into the eye via pressurized gas (gas propulsion) (U.S. Pat. No. 3,934,585). However, both of these techniques present difficulties.

The direct ejection technique requires the use of gas which is pressurized in order to propel the ejected liquid with sufficient velocity to reach the eye. However, the direct ejection technique causes ejection of at least some of the liquid before the gas has reached a velocity sufficient to propel the liquid to the surface of the eye. In addition, the direct ejection technique causes an audible pop or snap as the liquid is ejected, resulting in blinking and the potential for consequent misplacement of the liquid.

This invention employs a gas such as air, $N_2$, $CO_2$, or any other gas which is inert and safe for medical applications, to induce the delivery of a measured amount of fluid, often aqueous, to the eye. There are several embodiments for this technique, but two method embodiments are described here to demonstrate the concept. The first method is a single step induction method. The single step method uses the motive gas for metering and delivering a material to the eye. The volume of material delivered to the eye is controlled by the volume and pressure of the motive gas. The second method is a two step induction method. In this method the desired volume of material is pre-metered into a passage or compartment. The motive gas is forced through the compartment to mix with and eject the preselected amount of material through a nozzle to the eye.

Several apparatus embodiments are described which are multiple dose devices, although they are also capable of operating as unit dose devices. These embodiments implement the overall process of the use of gas induction—i.e., the movement of a measured volume of gas to separate and deliver small preselected volumes of fluid to the eye or other sites. The embodiments shown use a piston and spring for the creation of a momentary predetermined high pressure air pulse of a predetermined volume. It will be appreciated, however, that the air pulse may be generated in a variety of ways, and that other gas sources such as pre-pressured cartridges or canisters of $CO_2$, $N_2$ or other non-toxic, non-flammable gases (such as Noble gases) may be used in conjunction with appropriate valving schemes.

Figure 1:
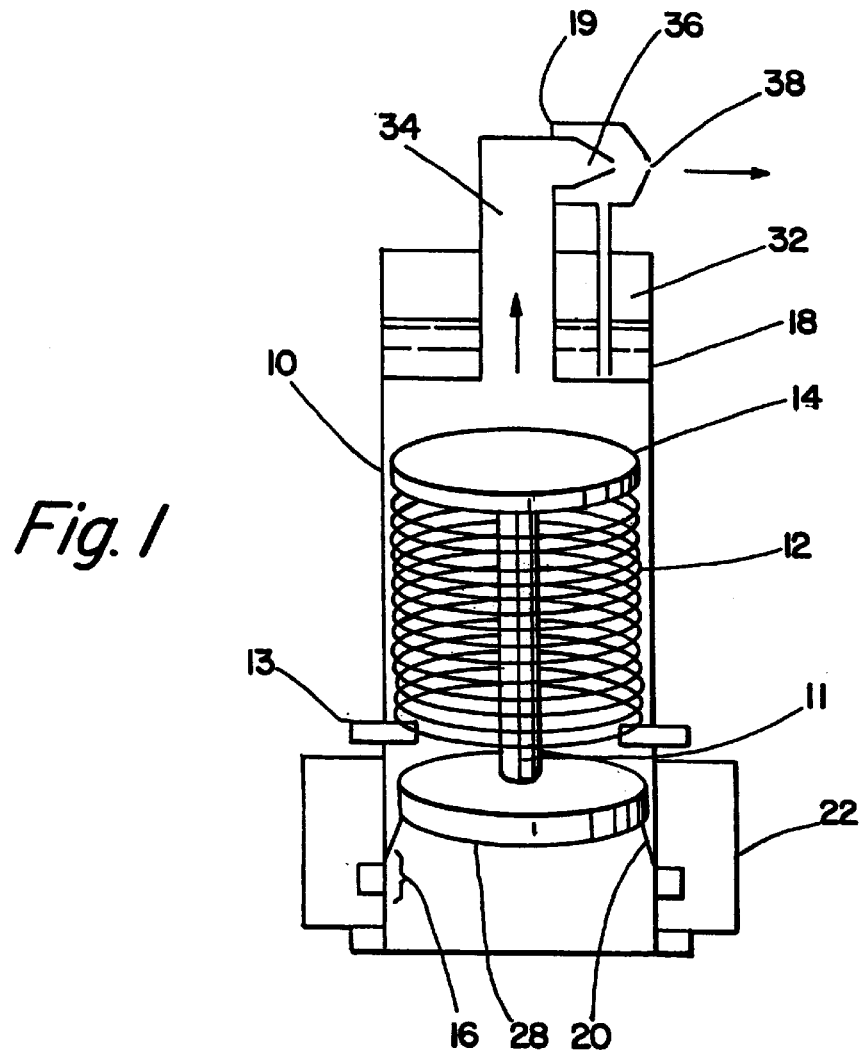
FIG. 1 is a schematic, longitudinal, cutaway view of one embodiment of the invention revealing internal components of the embodiment.

A single step induction system is illustrated in FIG. 1. This system employs a measured amount of gas delivered at a given pressure to induce a measured volume of fluid to be pulled into the mixing stream of the pump, become mixed with the air stream, and then ejected from a nozzle.

FIG. 1, FIG. 2, FIG. 3, and FIG. 4 show the principal components of a gas entrainment delivery system using an eductor pump (sometimes referred to as a jet pump). A venturi or paddle wheel may be substituted for the eductor pump without departing from the spirit of the invention. The principal components are:

A main body or housing 10 which houses a spring 12, piston 14, release mechanism and cocking mechanism 16, and material reservoir 18, and serves as the base for a eductor pump 19 (or a venturi). The body 10 in one preferred embodiment is typically about ¾" to 1" in diameter and about 1" to 3" long.

The cocking mechanism 16 enables the piston 14 to be pulled back a predetermined distance, and the spring 12 to be compressed. In this case, the cocking mechanism employs a rotating sleeve 22 which enables the piston to be cocked by twisting the sleeve. The sleeve has a slanted groove shown in FIG. 4A which engages a catch mechanism 20 on the bottom of the piston. The sleeve is typically about ⅛" to ¼" larger in diameter than the main body and about ½" high. The catch mechanism shown in FIG. 3 comprises two catches 24 spring loaded by metallic spurs 26 attached to a centralizing disk 28. It will be apparent that the stroke of the piston may be varied by varying the position of the catches.

The reservoir 18 is preferably close to the eductor pump 19, and contains a liquid. The reservoir 18 has a feeder tube 32 extending through the top of the reservoir down to the bottom to enable the liquid to be pulled up into the eductor pump for delivery. In this case the reservoir 18 is doughnut shaped to permit a passage 34 to allow air to flow through the middle from above piston 14 to drive the eductor pump 19 affixed to the top of housing 10. The outer diameter of the reservoir 18 is the diameter of the main housing 10, and there is an inner diameter to allow the air tube 34 to pass through the middle.

The eductor pump 19 converts pressurized gas from passageway 34 into suction, and pulls liquid from the reservoir 18 up the feeder tube 32 into the pump, and then ejects it onto the eye. The eductor pump here comprises an inner nozzle 36 and an outer nozzle 38. The inner nozzle 36 is called the jet, and the outer nozzle 38 is called the diffuser. The diameter of the diffuser is preferably larger than the diameter of the jet. The operation of the eductor pump for this system is explained in more detail below. The eductor pump may be cylindrical in shape.

The piston 14 is a free-sliding piston which is sealed against the housing 10, and connected to a shaft 11 and disk 28 for guiding the piston. The guiding mechanism is connected to the cocking mechanism 16.

The spring 12 is positioned between the piston 14 and one or more spring stops 13. The spring is also centered around the shaft 11. The spring is compressed by action of the cocking mechanism as it is drawn with piston 14 by the cocking mechanism. The cocking mechanism includes a sleeve 22 which has two opposed, inclined grooves or tracks 44. The sleeve typically may be larger than the housing. It also includes a pair of spring loaded latches or catches 24 which snap into the grooves when the piston 14 moves downward against the spring 12. The catches 24 are biased outward by spring members attached to the disk 28. Rotation of the sleeve causes the catches 24 to ride down along the grooves, until the catches enter deeper recesses or holes in the sleeve 22. They remain cocked in this position until their release by release mechanism 46. The release mechanism 46 may comprise elongated buttons or rods 48 which are positioned on the sleeve 22 opposite the catches 24 when in their cocked position. Simply pushing or pressing the buttons or rods 48 inward displaces the catches 24 inward and out of the grooves 44, thereby freeing the spring to thrust the piston upward. Upward movement of the piston compresses and drives a selected volume of gas through the passageway 34 and thence the eductor pump. This, in turn, draws a selected volume of liquid from the reservoir 18 through the feeder tube 32 and into the gas stream. The liquid mixes with the gas and jets through the outer nozzle 38.

Figure 3A:
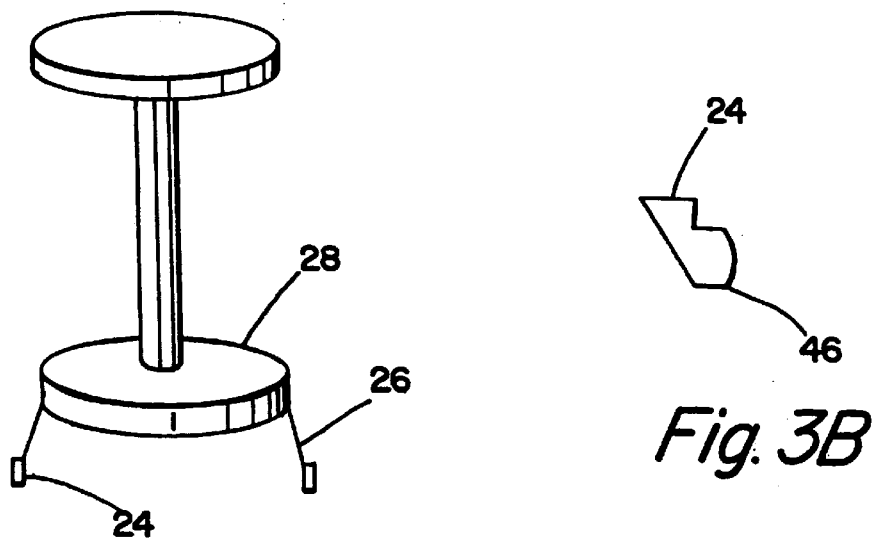
FIG. 3A is a schematic view of the piston and latch assembly of FIG. 1.
Figure 3B:
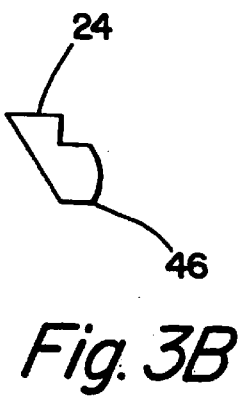
FIG. 3B is a schematic, enlarged side view of a latch shown in FIG. 3A.
Figure 2A:
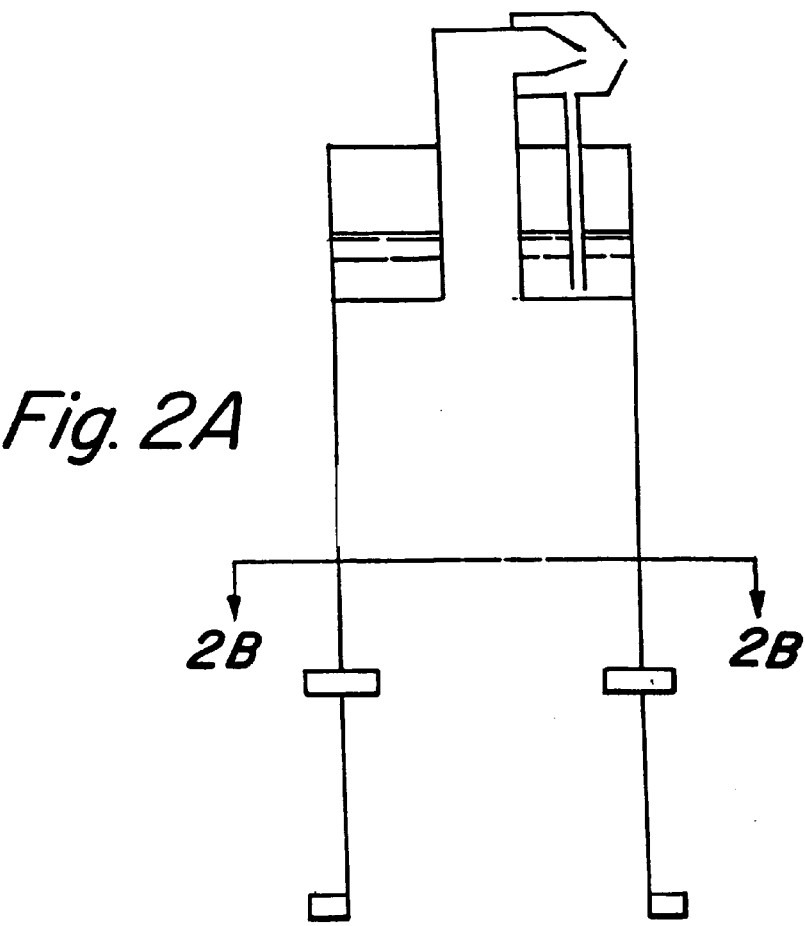
FIG. 2A is a schematic cutaway front view of the housing shown in FIG. 1.
Figure 2B:
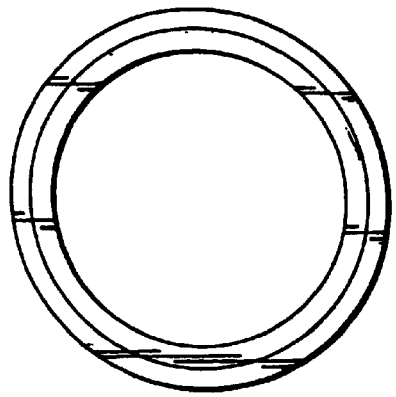
FIG. 2B is a bottom view of the housing.
Figure 2C:
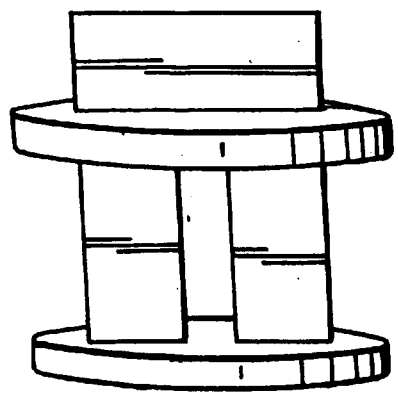
FIG. 2C is a side view of the portion of the housing extending downward from the lines C—C in FIG. 2A.

A drawing of the housing with the piston and twist ring removed is shown for clarity in FIG. 2A. The piston and the locking and release mechanisms are shown in FIG. 3A and FIG. 3B. The twist ring is shown in FIG. 4 with a slanted slot cut on the inner surface of the ring. There are two slots on the twist ring, one on each side of the twist ring.

DESCRIPTION OF INVENTIVE PROCESSES

Consideration of the eductor pumps of the art using steady incompressible flow and treating the fluid mixing empirically yields a straightforward analysis (Jumpeter, 1986; Gosline et al., 1937). However, these analyses are incomplete for this application because they do not provide expressions that give explicit transfer volumes for motive and suction fluids with dissimilar densities. Furthermore, the steady flow approximation must be modified to allow the transient effects that are significant for the delivered material. Therefore, the inventors present an analysis here that gives the transfer of a specific volume of suction fluid for a give volume of motive fluid where the densities of the two fluids are not equal. A detailed drawing of an example of an eductor pump is shown in FIG. 5 with representative dimensions. For the sake of simplicity, the flow of the motive gas and the suction fluid may be approximated by steady incompressible flow, hence, that Bernoulli's equation may be used for the conservation of momentum flow:

$$\frac{P}{\rho} + \frac{V^2}{2} = H \tag{3}$$

where H is normalized head pressure and is a constant (meters$^2$/sec$^2$), P is pressure in pascals (Pa), $\rho$ is mass density of the fluid, and V is the fluid velocity in meters/second (Fox and McDonald, 1992). The constant, H, on the right hand side of the equation will be referred to as the head or stagnation pressure normalized to the density of the gas or fluid. The stagnation pressure is a normalized quantity composed of the static pressure P and the dynamic pressure $\rho V^2/2$. These quantities are normalized to the fluid density for simplicity. This equation is consistent for a consistent set of units, such as MKS units.

For the eductor pump shown in FIG. 5, it is important to describe the operation of the device so that it is clear that a pre-metered volume of gas induces a preselected amount of fluid to be delivered. The equation for the head pressure, $h_1$, of the motive gas is:

$$h_1 = \frac{P_1}{\rho_1} + \frac{V_1^2}{2} \tag{4}$$

where $V_1$ can be considered to be zero before the fluid enters the nozzle. The following equation relates the nozzle velocity to the normalized head pressure, $h_1$.

$$h_1 = \frac{P_s}{\rho_1} + \frac{V_N^2}{2} \tag{5}$$

where Ps is the suction pressure, and $V_N$ is the nozzle velocity. The equation for the velocity and pressure in the diffuser section of the pump, exiting into pressure $P_2$, usually atmospheric pressure, is:

$$\frac{P_2}{\rho_2} = \frac{P_s}{\rho_2} + \frac{V_M^2}{2} \tag{5A}$$

Where $V_M$ is the velocity of the mixture of motive gas and entrained suction fluid in the diffuser before exiting the pump. Equations 5 and 5A establish the relationship between the velocities at the nozzle and in the diffuser, and the motive, suction, and exit pressures, $P_1$, $P_s$, and $P_2$, respectively. These equations may be combined and provide an expression for the relative ability of the eductor pump to eject the suction fluid. This relative pumping ability is expressed as the head ratio, $R_H$, expressed in terms of the pressures at the ports of the pump:

$$R_H = \frac{(P_1 - P_s)\rho_2}{(P_2 - P_s)\rho_1} \quad (6)$$

where $P_1$ is the piston pressure, $P_2$ is the discharge pressure at the output of the pump, $P_S$ is the suction pressure, $\rho_2$ is the mass density of the mixture of the motive gas and suction fluid, and $R_H$ is the head ratio for the eductor pump corrected for the mass densities of the motive gas and the effective density of the motive gas mixed with the suction fluid. The density of the fluid/gas mixture is difficult to determine a priori. This mixture, or average density, depends strongly on the properties of the material to be delivered, and the details of the pump. One factor, for example that changes the relative fraction of liquid or material from the reservoir induced into the eductor pump is the length of the feeder tube. The mixing ratio, r, may be defined as the average volume of ejected suction fluid, $v_{suction}$, to the average volume of motive gas initially displaced by the piston, $v_{gas}$:

$$r = \frac{v_{suction}}{v_{gas}} \quad (7)$$

The average mass density of the ejected mixture may be computed by finding the total mass of the ejected mixture and dividing by the total volume of the ejected mixture (at the exit or atmospheric pressure). This may be expressed in terms of the motive gas density, the suction fluid (material to be delivered) density, and the mixing ratio as:

$$\rho_2 = \frac{\rho_1 + r\rho_{suction}}{1 + r} \quad (8)$$

where $\rho_{suction}$ is the density of the suction fluid.

Empirical measurements show that for moderate displacements of air (i.e., 2–5 ml), a suction fluid of water, and a short feeder tube, the relative volume of material ejected to the volume of motive gas displaced is approximately 1.4 to 1.8 ul/ml. If the average value of these ratios as determined in the example herin is used, the inventors have 1.6 ul/ml, and an average density for $\rho_2$ of 2.8 kg/m³.

Thus, a predetermined amount of suction fluid may be delivered by setting the pressure and the amount of motive gas to be displaced. This may be calculated by knowing the relative velocities of the motive fluid to the mixed fluid stream and may be calculated from $R_H$ as follows:

$$V_M = \frac{V_N}{\sqrt{R_H}} \quad (9)$$

where $V_M$ is the velocity of the mixed fluids that are ejected, and by using conservation of momentum the inventors can write the total mass of suction fluid transferred in terms of the total mass of the motive gas:

$$\rho_{suction} v_{suction} = \rho_1 v_{gas}\left(\frac{V_N}{V_M} - 1\right) \quad (10)$$

This equation shows that the ejection velocity must be reduced compared with the nozzle velocity since the combined mass of the suction fluid and motive gas are greater than the mass of motive gas alone. Equation 10 can be divided by $v_{gas}$ and $\rho_{suction}$ to give an expression in terms of the mixing ratio, r. Furthermore, $$\frac{V_N}{V_M} = \sqrt{R_H}$$

can be substituted into equation 10 to obtain:

$$r = \frac{\rho_1}{\rho_{suction}}\left(\varepsilon\sqrt{R_H} - 1\right) \quad (11)$$

Equation (11) shows that the volume of the suction fluid, $v_{suction}$ transferred is controlled through the mixing ratio, r, by the total volume and density of the motive fluid, and the head ratio, $R_H$ at which it is delivered. Thus it is clear from equation 11 that the total volume of fluid, $v_{suction}$, ejected can be controlled by controlling the amount of gas, $v_{gas}$, at a known density and pressure that is forced through the nozzle. Mixing and turbulence losses have been included by adding an empirically determined efficiency, (19). Although equation 11 appears to be an expression for r in terms of other variables, $R_H$ depends on r through the term $\rho_2$. If $\rho_2$ is replaced in the expression for $R_H$ by equation 8, and r is solved for in terms of all the other variables, a 3rd order polynomial in r is obtained, the first real root of which is the physically meaningful value for r. The expression is:

$$r^3 + Ar^2 + Br + C = 0 \quad (12)$$

$$A = \frac{2}{M_r} + 1 \quad (12a)$$

$$B = -\varepsilon^2 \frac{P_H}{M_r} + \frac{2}{M_r} + \frac{1}{M_r^2} \quad (12b)$$

$$C = \frac{1 - \varepsilon^2 P_H}{M_r^2} \quad (12c)$$

$$P_H = \frac{P_1 - P_s}{P_2 - P_s} \quad (12d)$$

$$M_r = \frac{\rho_s}{\rho_1} \quad (12e)$$

The first positive real root of equation (12) will give the mixing ratio if the motive, suction, and discharge pressures, the density of the motive and suction fluids, and the empirical efficiency coefficient are known. The mixing ratio can then be determined. This equation is limited in its predictive ability because it cannot be used until $\varepsilon$ is determined. However, it is useful because it gives the mixing ratio, r, as a function of all of the other parameters of the eductor pump. This equation is essential for determining how the mixing ratio changes when other variables such as motive gas pressure or density are changed.

Although velocity does not appear explicitly in equation 12, it is clear that the pump action is caused by the flow of gas through the inner and outer nozzles of the eductor pump.

No suction fluid will be ejected until the velocity is high enough to create sufficient suction to overcome the forces holding the suction fluid in the feeder tube.

It is important to note that equation 12 cannot be used a prioi to determine the exact delivery volumes. There are a number of empirical factors that cannot be determined except by measurement. First, the overall efficiency factor, $\epsilon$, is not known and must be determined empirically. In addition, the suction pressure, $P_s$, is greatly affected by surface adhesion forces and surface tension forces that are difficult to calculate in advance. Therefore, these equations alone cannot be used to predict the exact volume delivery of an inventive eductor pump for the purpose of small volume delivery. However these equations are useful for determining the scaling behavior of the pump assembly once these factors have been determined. The process embodied in this collection of equations and the empirical data constitute an inventive process of this application. Changes in the delivered volume of fluid, $v_{suction}$ may be determined from changes in the volume of the piston, the pressure of the spring, or the density of the motive gas used.

EXAMPLE 1

Figure 36:
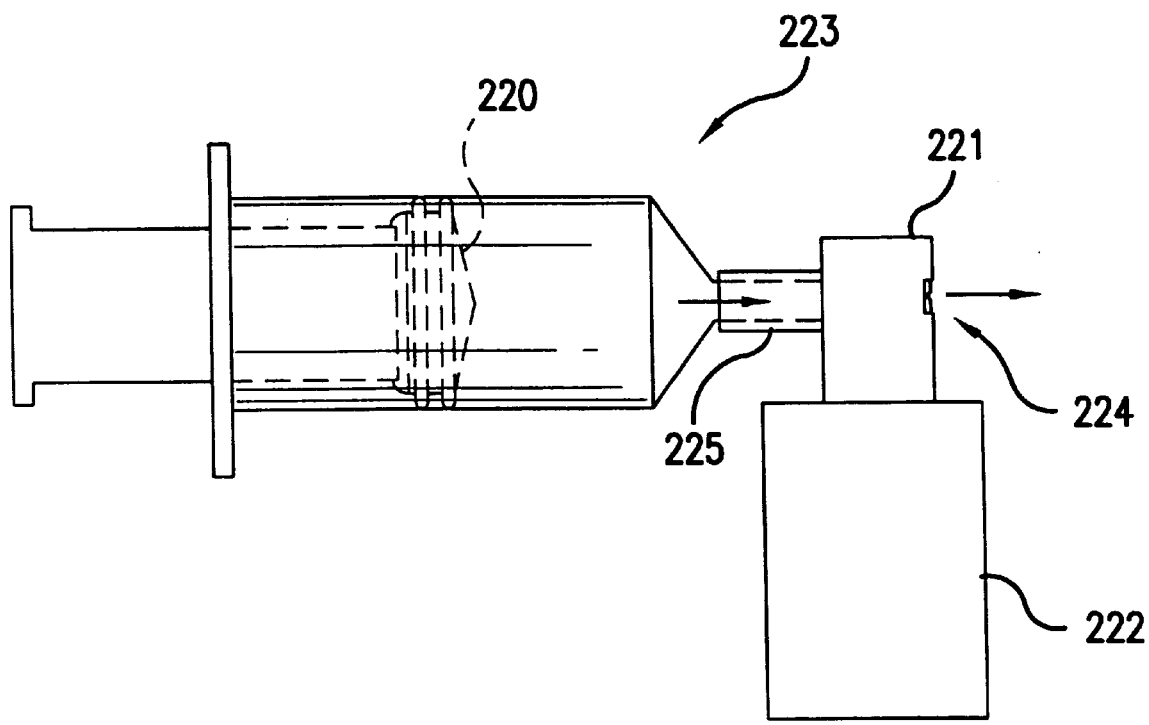
FIG. 36 Embodiment Using Syringe Piston

Test data indicate that an early prototypic embodiment similar to that in FIG. 36 can deliver reliably a 5 ul volume to a pre-determined target, such as the eye, with a 20% standard deviation from the average. The data are shown in following Table 1. In this test the feeder tube was about 2" long and the fluid level in the reservoir was about ¾" below the eductor pump. Thus, the total hydrostatic head against which the pump had to work was about ¾". The volume of fluid delivered was determined using a petri dish containing a small wad of dry cotton on a precision scale. The nozzle was placed in close proximity to the cotton and then discharged into the cotton. The difference in the weight of the petri dish was measured before and after the discharge. The suction fluid in this case was tap water which has a known density of 103 kg/m3. The temperature of the water was approximately room temperature, estimated to be about 23° C. The scale was a Mettler-Toledo Model AG245 with a 10 ug accuracy. A change in weight of 1000 ug (1 mg) corresponded to a 1 ul delivery to the cotton. The piston used was that in a standard 10 cc polyethylene syringe, and the pressure was applied by the thumb. Different volumes of air (2.5, 5.0 and 7.0 ml) were displaced from the syringe by its piston. The delivery was accomplished by a quick, sharp push to the syringe piston. The same operator was used for all of the test data shown here. Since the motive piston was pushed by hand, variability was probably introduced into these results; a spring or other mechanical means as described in the preferred and especially preferred embodiments of the invention provides more repeatable motive pressure.

Table 1 shows the volumes of suction fluid that were delivered by the above device by ejecting different quantities of air from the syringe. The data in the first or left hand column show the quantities of suction fluid (tap water) that were delivered by 2.5 ml of air displaced by the syringe in 21 different trials. The second and third columns show similar results, when the syringe delivered 5.0 ml and 7.5 ml volumes of air, respectively. The data in Table 1 below show that as little as 2 ul average volume of suction fluid may be delivered, with a standard deviation of about 22% of the mean. The maximum volume was 2.9 ul, while the minimum as 1.3 ul. The ratio of maximum to minimum volume delivered was about 2, and it was fairly consistent for all of the test data taken so far. A further important feature of this data is that the mixing ratio of total suction fluid volume to motive gas volume changes noticeably from the 2.5 ml of motive gas, to the 7.5 ml of motive gas used. The mixing ratio changes from 0.8 ul/ml for 2.5 ml of motive gas to 1.45 ul/ml for 7.5 ml of motive gas, respectively. This is about a 45% change in the mixing ratio from the minimum volume of gas used to the maximum volume used, which corresponds to about a 3-to-1 change in the motive gas.

TABLE 1

Volumes (Microliters) of Fluid Delivered by Different Volumes of Motive Air

| Trial # | 2.5 ml air | Trial # | 5 ml air | Trial # | 7.5 ml air |
|---|---|---|---|---|---|
| 1 | 2.0 | 1 | 5.0 | 1 | 9.5 |
| 2 | 1.5 | 2 | 5.5 | 2 | 9.5 |
| 3 | 1.7 | 3 | 5.7 | 3 | 9.0 |
| 4 | 1.7 | 4 | 5.9 | 4 | 9.5 |
| 5 | 1.8 | 5 | 6.4 | 5 | 9.3 |
| 6 | 1.5 | 6 | 5.8 | 6 | 8.6 |
| 7 | 2.7 | 7 | 6.2 | 7 | 9.5 |
| 8 | 1.9 | 8 | 7.0 | 8 | 11.7 |
| 9 | 1.3 | 9 | 7.1 | 9 | 12.4 |
| 10 | 2.7 | 10 | 5.2 | 10 | 11.4 |
| 11 | 2.8 | 11 | 6.7 | 11 | 10.8 |
| 12 | 2.9 | 12 | 6.6 | 12 | 12.3 |
| 13 | 2.3 | 13 | 5.0 | 13 | 11.3 |
| 14 | 2.2 | 14 | 6.0 | 14 | 10.0 |
| 15 | 2.2 | 15 | 5.0 | 15 | 11.6 |
| 16 | 2.0 | 16 | 5.7 | 16 | 10.9 |
| 17 | 2.4 | 17 | 5.6 | 17 | 13.8 |
| 18 | 2.2 | 18 | 4.7 | 18 | 10.9 |
| 19 | 1.8 | 19 | 5.5 | 19 | 9.5 |
| 20 | 1.5 | 20 | 5.0 | 20 | 11.6 |
| 21 | 1.8 | 21 | 7.0 | 21 | 11.6 |
| 22 | 1.4 | 22 | 5.9 | 22 | 10.5 |
| Average | 2.0 | 23 | 6.4 | 23 | 10.4 |
| Std Dev | 0.5 | 24 | 5.8 | 24 | 13.0 |
| Max | 2.9 | 25 | 5.9 | 25 | 12.7 |
| Min | 1.3 | 26 | 6.0 | 26 | 12.5 |
| | | 27 | 6.0 | 27 | 11.1 |
| | | 28 | 6.2 | 28 | 10.2 |
| | | 29 | 7.1 | 29 | 12.2 |
| | | 30 | 6.5 | 30 | 10.9 |
| | | 31 | 6.6 | 31 | 10.9 |
| | | 32 | 6.3 | 32 | 11.8 |
| | | 33 | 6.0 | 33 | 10.5 |
| | | 34 | 5.6 | 34 | 10.4 |
| | | 35 | 6.0 | 35 | 8.9 |
| | | 36 | 6.6 | 36 | 11.6 |
| | | 37 | 6.1 | 37 | 9.1 |
| | | 38 | 5.9 | 38 | 13.4 |
| | | 39 | 5.8 | 39 | 11.3 |
| | | 40 | 6.0 | 40 | 11.9 |
| | | Average | 6.0 | 41 | 9.8 |
| | | Std Dev | 0.6 | 42 | 10.4 |
| | | Max | 7.1 | 43 | 10.4 |
| | | Min | 4.7 | 44 | 12.5 |
| | | | | Average | 10.9 |
| | | | | Std Dev | 1.3 |
| | | | | Max | 13.8 |
| | | | | Min | 8.6 |

Because the amounts of liquid measured were very small (in some cases less than 2 ul), evaporation of the liquid from the target on the scale was potentially a significant factor in the measurements. The evaporation rate was proportional to the amount of liquid delivered to the cotton; smaller delivery volumes had a smaller rate of evaporation. In order to minimize the effect of evaporation, the readings were taken as quickly as possible after the delivery to the cotton, 10 to 20 sec, and efforts were made to keep the time between delivery and the measurement of the weight change constant. The determining factor on the measurement time was the time for the scale to stabilize. The cotton target was changed after 5 to 10 deliveries. The evaporation of the liquid from the target ranged from less than about 0.5 mg per min for a fresh target to about 3 mg/min for the larger volume deliveries after about 10 deliveries. The large evaporation rates were only observed with multiple deliveries of water to the cotton at relatively high volume (i.e., 10 ul). Overall, the evaporation rates were not considered to be significant for the measurements made.

EXAMPLE 2

Table 2 below shows data taken with a similar early prototypic eductor pump and motive piston. The important differences were that the feeder tube was shortened to about ¾", and the liquid was about ¼" below the eductor pump. The experimental design was otherwise the same as that for the data in Table 1. In these trials different volumes of motive air (1.0, 2.0, 2.5 and 4.0 ml) were used to deliver tap water as the delivery liquid. It may be seen that the standard deviations for this data are all very close to about 20% of the average volume delivered, except for the 4 ml of air delivery which had a standard deviation of about 15% of the average value. More importantly, the mixing ratio computed using the average ranged from a minimum of 1.4 ul/ml to 1.8 ul/ml. This is a change of only 14% over the entire range of volumes delivered.

The ratio of the change of motive gas volumes is 4 $\mu$l/1 ml or a range of 4-to-1.

TABLE 2

Different Volumes of Liquid Delivered by Different Volumes of Motive Air

| Trial # | 1.0 ml air | Trial # | 2.0 ml air | Trial # | 2.5 ml air | Trial # | 4.0 ml air |
|---|---|---|---|---|---|---|---|
| 1 | 1.40 | 1 | 2.60 | 1 | 4.62 | 1 | 7.40 |
| 2 | 1.36 | 2 | 2.74 | 2 | 3.52 | 2 | 10.00 |
| 3 | 1.16 | 3 | 2.45 | 3 | 3.06 | 3 | 7.06 |
| 4 | 1.40 | 4 | 2.90 | 4 | 4.14 | 4 | 6.50 |
| 5 | 1.08 | 5 | 3.36 | 5 | 4.50 | 5 | 6.60 |
| 6 | 1.40 | 6 | 3.60 | 6 | 4.30 | 6 | 6.70 |
| 7 | 1.08 | 7 | 3.30 | 7 | 3.81 | 7 | 6.30 |
| 8 | 1.35 | 8 | 2.36 | 8 | 5.54 | 8 | 8.11 |
| 9 | 1.40 | 9 | 2.10 | 9 | 4.05 | 9 | 9.30 |
| 10 | 1.65 | 10 | 2.00 | 10 | 3.85 | 10 | 6.84 |
| 11 | 0.95 | 11 | 3.96 | 11 | 3.58 | 11 | 7.50 |
| 12 | 1.05 | 12 | 2.00 | 12 | 4.55 | 12 | 7.00 |
| 13 | 1.35 | 13 | 2.80 | 13 | 4.21 | 13 | 5.20 |
| 14 | 1.82 | 14 | 3.10 | 14 | 3.68 | 14 | 6.88 |
| 15 | 1.55 | 15 | 2.60 | 15 | 5.33 | 15 | 6.50 |
| 16 | 1.18 | 16 | 4.00 | 16 | 6.56 | 16 | 6.67 |
| 17 | 1.37 | 17 | 3.20 | 17 | 3.80 | 17 | 8.44 |
| 18 | 1.04 | 18 | 2.40 | 18 | 4.20 | 18 | 7.44 |
| 19 | 1.28 | 19 | 2.30 | 19 | 4.80 | 19 | 7.67 |
| 20 | 1.36 | 20 | 3.00 | 20 | 3.01 | 20 | 6.19 |
| 21 | 1.50 | 21 | 4.20 | 21 | 4.26 | 21 | 8.00 |
| 22 | 1.69 | 22 | 4.20 | 22 | 4.21 | Average | 7.25 |
| 23 | 1.10 | 23 | 3.60 | 23 | 4.09 | Std Dev | 1.06 |
| 24 | 1.84 | 24 | 3.40 | 24 | 4.20 | Max | 10.00 |
| 25 | 1.36 | 25 | 3.15 | Average | 4.24 | Min | 5.20 |
| 26 | 1.50 | 26 | 3.20 | Std Dev | 0.75 | | |
| 27 | 2.10 | 27 | 3.30 | Max | 6.56 | | |
| 28 | 1.60 | 28 | 2.80 | Min | 3.01 | | |
| 29 | 1.40 | 29 | 2.40 | | | | |
| 30 | 1.24 | 30 | 3.60 | | | | |
| 31 | 1.72 | 31 | 3.70 | | | | |
| Average | 1.40 | 32 | 4.30 | | | | |
| | | Average | 3.08 | | | | |
| Std Dev | 0.26 | Std Dev | 0.65 | | | | |
| | | Max | 4.30 | | | | |
| Max | 2.10 | Min | 2.00 | | | | |
| Min | 0.95 | | | | | | |

The fact that the range of mixing ratios was much smaller for the data in Table 2 as opposed to that in Table 1, over an even larger range of motive gas volumes, is evidence that control of the amount of fluid delivered by this method was achieved. By determining the parameters needed to produce a stable mixing ratio, as was accomplished here, the amount of motive gas needed to deliver a preselected volume of fluid may be determined. A longer feeder tube requires more gas displacement to achieve the same relative mixture of the fluid to the motive gas. For a longer feeder tube (i.e., one of about 2" in length), the mixture depends strongly on the amount of gas displaced. A shorter feeder tube (about ½" in length) shows only a very slight dependence of the mixing ratio to the total gas displaced for the range of 1 to 4 ml of air.

Another feature of the mixing ratio of the long feeder tube is that for large gas displacements, it asymptotes to a value that approaches the mixing ratio for the short tube. This is due to the need to overcome the inertia of the liquid in the feeder tube. The shorter the feeder tube, the less the inertia that needs to be overcome. When a larger volume of motive gas is used, the liquid approaches a more constant steady flow, resulting in a more consistent mixing ratio.

In order to estimate efficiency of the eductor pump, and to predict the influence of changes in the configuration of the feeder tube, there is a need to be able to calculate the total effective head ($H_S$) against which the eductor pump must pull in order to produce a positive flow into the pump. The forces have the following components: gravity, static pressure, and viscosity. The resulting equation for the suction pressure, $P_S$, is:

$$P_s = \rho_{suction} gz + V_s K + P_{stat} + F\left(\frac{dV_s}{dt}, V_s\right) \quad (13)$$

where g is the pull of gravity, z is the height of the pump above the fluid level, $P_{stat}$ is the pressure corresponding to static force such as surface tension, $V_S$ is the velocity of the fluid in the tube leading from the reservoir to the eductor pump, K is a constant computed from the absolute viscosity of the fluid at the typical temperatures that are expected and the dimensions of the feeder tube, and the function F of the time derivative of the suction fluid velocity in the feeder tube. Because the volume flow rates are so low (10–9 m$^3$/s) for the suction fluid, the viscosity term for aqueous fluids with properties similar to water is negligibly small (0.5 Pa) even for small diameter feeder tubes, in this case 0.05" diameter. The flow for aqueous solutions is laminar, again because of the low volume flow of the suction fluid. The gravity pressure is 120 Pa for ½" of total lift (½" feeder tube). The static pressure term was estimated from the amount of fluid that remained in the feed tube when the tube was held free in the air vertically and was about ⅜" which corresponds to a value of about 90 Pa. Thus, the value of 210 Pa was used as an estimate for the overall suction head.

Using equation 12, the measured mixing ratio, and estimating the relative head ratio $R_H$ corrected for the mass densities of the mixture and motive gas, one can estimate the relative efficiency, $\epsilon$, of the eductor pump. The over pressure in this particular example, $P_1$, which is the pressure in excess of atmospheric pressure, in the piston is estimated at between 60 kPa to 80 kPa (i.e., 60–80% of one atmosphere). The suction pressure, Ps, is estimated to be about 210 Pa. Corresponding $R_H$ is between 285 and 380, which gives an efficiency, $\epsilon$, in the range of 0.07 to 0.09 using equation 12. Higher head pressures will tend to have lower values of e, but the reproducibility is better. Higher head pressures result in lower standard deviations of delivery.

Certain approximations have been made but are not believed to significantly affect accuracy. Thus, an assumed steady flow discounted the inertia of the motive gas as well as the suction fluid. This is a better approximation for the short tube than for the longer tube. Since the suction fluid is nearly incompressible, the entire suction tube must be set in motion to feed the pump, hence the inertia of interest is the inertia of the entire fluid in the feeder tube. The longer the feeder tube, the greater the inertia. The constancy of the mixing ratio of the short tube for the various displacements of air suggests that the inertia is not a large factor, and hence the steady flow approximation is accurate for that case. However, it is also apparent both from the data and from equation (13) that longer feeder tubes may have a very significant effect on the mixing ratio. It will be observed from the data that the standard deviations of the data with the longer feeder tube is less than the data for the short feeder tube. Hence, a selection may be made that longer feeder tubes may allow deliveries with smaller standard deviations in the individual deliveries, but the average mixing ratio will change more as the total volume of motive gas is changed.

Figure 6A:
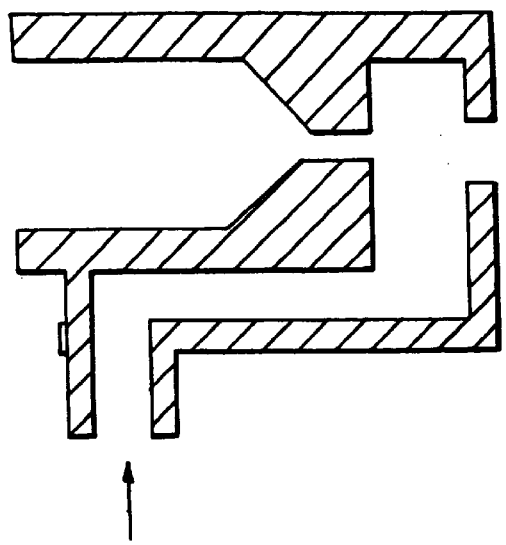
FIGS. 6A, 6B, and 6C show schematically a variation of the eductor pump of FIG. 1.
Figure 6C:
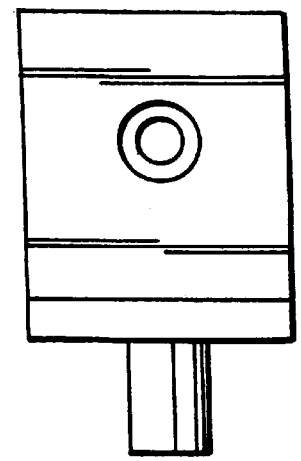
Figure 6B:
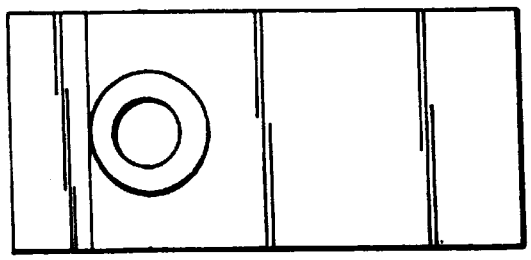

The pump is an operational element of this invention, and may comprise an eductor pump, a venturi or a paddle wheel. FIG. 6 shows a simple design of an eductor pump. This pump only has three parts to assemble, including the feeder tube for the suction fluid. One aspect of this pump design is that the housing for the motive jet, the pressure inlet, and the exit nozzle are all molded from the same piece. The small holes may either be molded or drilled quite easily. This pump may be made from plastic, such as polyolefin, polystyrene, polyvinyl chloride, metal, or any rigid, castable, or moldable (epoxy, silicone rubber, polyurethane) material that is impervious to fluids such as water. Although the outer shape is shown as rectangular here, the outer shape does not have any effect on the performance of the pump, therefore the most convenient outer shape may be made. There are no complicated moldings or assemblies required for this unit, and is therefore low cost. The dimensions shown in FIG. 6 are representative of typical dimensions for a hand-held unit for self administration and may be varied to suit the application. The assembly described also is of very low cost in both materials and construction.

Description of Modified Venturi Delivery Processes

Another one step method that may be used for gas induction employs a modified venturi as a pump. It is envisioned that the stagnation pressure of the motive gas provides a means to drive the fluid from the reservoir to the passage.

It is important to note that a significant optional feature of the invention is that the reservoir containing the material to be delivered must be momentarily pressurized by the action of the piston, otherwise, the stored material will not be as easily entrained into the stream of the gas flow.

Figure 7:
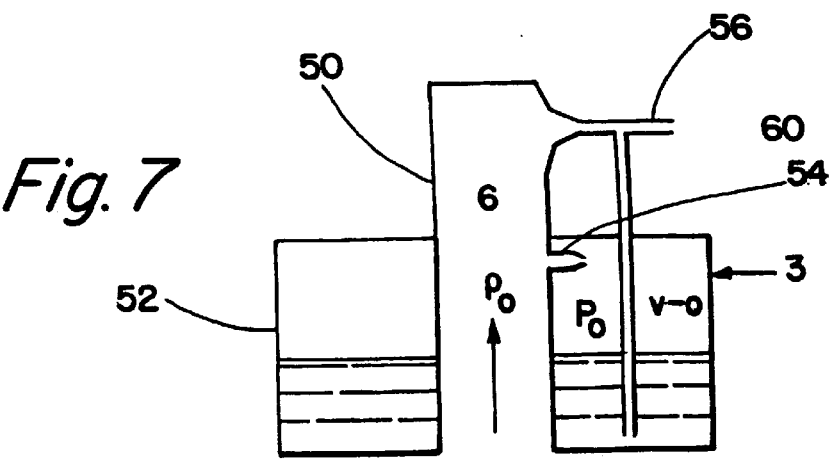
FIG. 7. is a schematic diagram of a venturi inventively modified to be a pump and feeder tube portion of an embodiment of the invention otherwise similar to that in FIG. 1.

FIG. 7 shows an example of how this may be implemented. The passageway 50 that provides the head for the motive air is also connected to the reservoir 52 containing the material to be delivered. The piston and the locking mechanisms are essentially the same as in the previous embodiment. However, the housing shown in FIG. 7 now has an additional passage (component 54 in FIG. 7) from the pressurized gas tube 50 into the reservoir 52 to provide the static pressure which pushes against the moving stream in the venturi 56. A very small feeder tube 60 connects from the reservoir to the venturi 56, and the reduced static pressure in the venturi 56 causes a pressure differential which forces the suction fluid to flow from the reservoir to the gas passage at a rate set by the driving pressure of the piston, the known fluid properties of the material to be delivered, and the diameter of the feeder tube 60 and the gas tube.

The material to be delivered is moved by the difference in pressure created when the flow velocity is increased above zero. Since the reservoir that contains the material to be delivered is at the pressure induced by the piston, that is the stagnation pressure, and the velocity is zero in this chamber, there will be a pressure difference that drives the material to be delivered up and through the tube 60 into the air flow. $P_S$ at the venturi 56 will be smaller than $P_o$ in the reservoir. If the gas velocity in 6 (FIG. 7) is not negligibly small, the reservoir will be pressurized to a pressure $<P_O$ but $>P_S$. The result will be that higher gas velocity will be required before the fluid is entrained.

Continuity of mass flow for steady state demands that the flow of mass into the tube equals the flow of mass out of the tube. It can be demonstrated that behavior of the venturi, and the use of stagnation pressure, induces the separation, metering, and delivery of the material similarly to the eductor pump.

Figure 8:
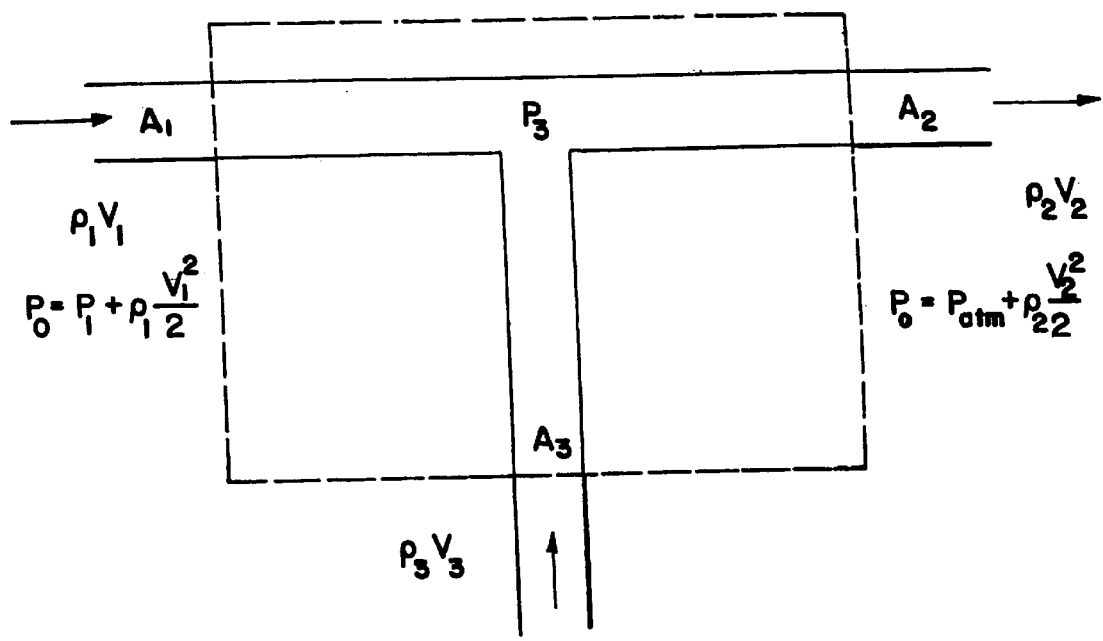
FIG. 8 is a schematic, side view of a form of pump which is an inventively modified venturi.

FIG. 8 shows how to analyze the modified venturi and feeder tube portion of this system using a control volume. The analysis proceeds by enforcing conservation of mass and momentum flow in and out of a well defined volume in space, specifically the venturi and feeder tubes. The continuity of mass flow is:

$$\rho_1 V_1 A_1 + \rho_s A_3 V_3 = \rho_2 V_2 A_2 \tag{14}$$

where $A_1$, $A_2$, and $A_3$ are the cross sectional areas of the three passages, and $\rho_1$, $\rho_2$, and $\rho_s$ are the average densities of the motive gas, the composite mixture of gas and material, and the suction material respectively.

If only a very small amount of material is metered into the passage, then the difference in pressure on the fluid in the feeder tube may be expressed as:

$$P_o - P_3 = \frac{V_1^2}{2}\rho_1 \tag{15}$$

where $V_1$ is the velocity of the gas in the venturi and $P_3$ the static pressure at port 3 in FIG. 8. To calculate the velocity, the mass of the suction fluid after it has mixed with the motive gas must be included. Thus, Bernoulli's equation, which represents conservation of momentum flow for this system is:

$$P_o = P_{atm} + \frac{V_1^2}{2}\rho_2 \tag{16}$$

where $\rho_2$ is the same as equation (8), $P_o$ is the head pressure from the piston, and is the average mass density of the mixture. $P_{atm}$ is the atmospheric pressure into which the mixture is ejected. Thus, the determining factor is again the mixing ratio, r, which will give the ratio of the volumes of the ejected fluid to the motive gas. Note that the suction into the venturi is calculated from the mass density of the motive gas alone, while the velocity of the mixture is calculated from equation (16).

Equations 15 and 16 may be combined and solved for the mixing ratio, r, in a manner similar to that used to derive equation 12. The expression for the mixing ratio, r, is:

$$r^2 M_r + r(1+M_r) + (1-R_p) = 0 \tag{17}$$

$$R_p = \varepsilon \frac{P_o - P_{atm}}{P_s} \quad (17a)$$

$$M_r = \frac{\rho_s}{\rho_l} \quad (17b)$$

This equation gives the mixing ratio in terms of the motive pressure, the ambient pressure, and the suction pressure, $P_o$, $P_{atm}$, and $P_s$, respectively. The positive root of this equation corresponds to the physically meaningful solution. This expression is valid for $R_H$ greater than 1. That is, where the difference between the pressure $P_o$ and $P_{atm}$ is greater than the suction pressure required to move the material from the reservoir by the pump.

If, as is shown in FIG. 7, the venturi tube is the same diameter before and after the suction fluid tap, then motive gas must compress slightly to allow for the presence of the suction fluid. However, the suction fluid is typically of high density and small volume compared to the motive gas. Therefore, entrainment of small amounts of suction fluid, or material, will not change the volume of the motive gas significantly. This means that neglecting the compression will not result in significant error.

The motive pressure difference is equal to the square of the velocity multiplied by one half of the density of the motive gas. This pressure difference only exists if the motive gas is in motion. The discharge of the fluid into the air passage way has the effect of reducing the flow velocity, and hence the difference in pressure. The process is self-regulating, and the flow may be determined. If a piston is supplying 5 kPa of pressure and the motive gas is air, and the suction pressure is 200 Pa, a mixing ratio of about 39 ul/ml is calculated for this method. Losses due to turbulence and mixing reduce this number similarly to the eductor pump.

Figure 13A:
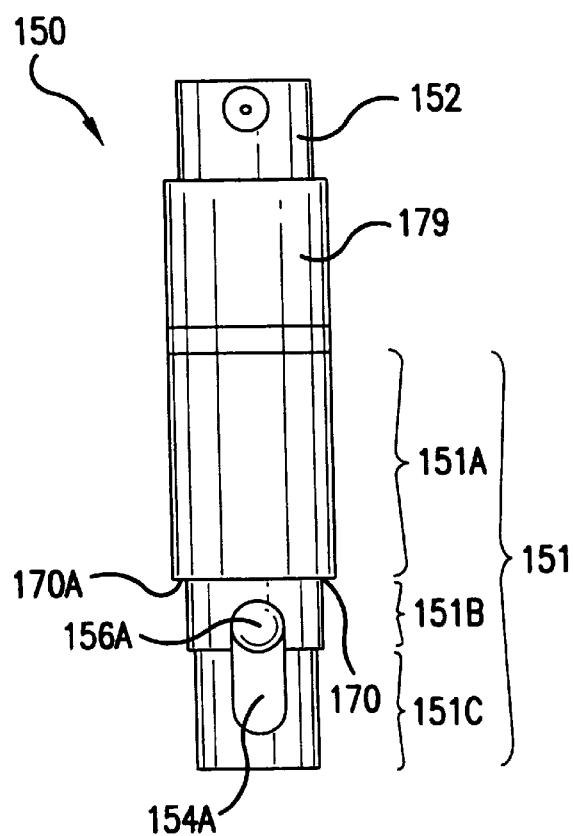
FIG. 13 is the device body (ID150) without rings and caps
Figure 13B:
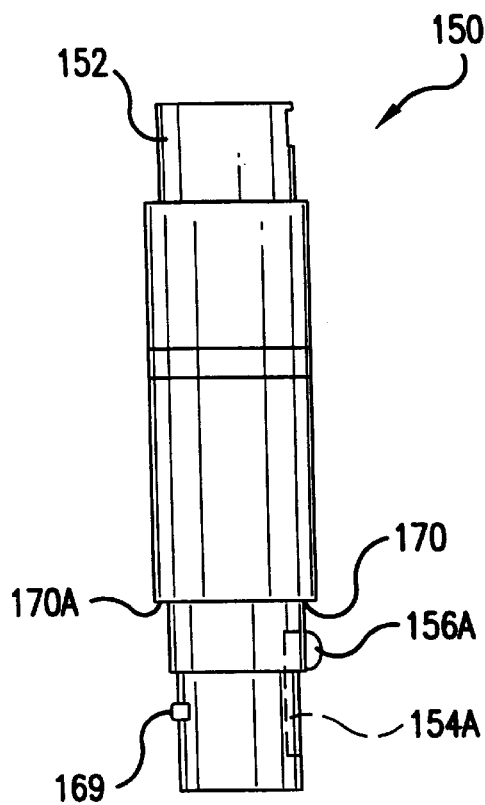
Figure 13C:
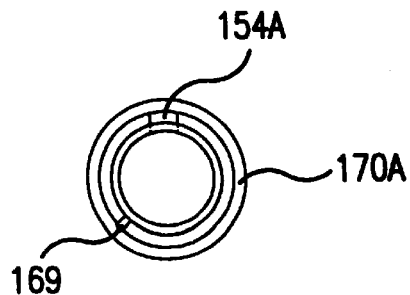

The mixture of gas and reservoir material is ejected as a series of one or more small droplets from the end of the nozzle, and hence onto the eye. The controlled volume of gas from the driving piston, and the known pressure applied to the piston determine the amount of fluid to be delivered. Other factors such as the viscosity and surface tension of the liquid control the droplet size. The limiting forces determining the delivery are the pressure in the container, the viscosity, gravity, and surface tension forces in the feeder tube, and reduced static pressure in the venturi due to the increase in the flow velocity. It may also be desirable for very high viscosity solutions to restrict the flow of gas into the material reservoir; this will reduce the rate of pressure rise in the reservoir, and reduce the relative flow of fluid into the chamber.

The most preferred embodiment uses a two diameter stream tube shown in FIGS. 21, 23, and 34. The purpose of the two diameter tube is to provide a control of the reservoir pressure so that the relationship between the pressure in the stream tube where the mixing occurs and the reservoir pressure can be changed to obtain the desired mixing ratio. In many cases, a the head pressure needs to be high enough to assure that the ophthalmic fluid is delivered to the eye. The head pressure to achieve this may cause the mixing ratio to be larger than is convenient. The use of the two diameter stream tube allows the exit velocity and the mixing ratio to be controlled independently. The two diameter stream tube allows the modulation of the reservoir pressure so that the equation for the mixing ratios for the two-diameter stream tube is:

$$\left(\frac{1}{\gamma}\right)(r^2 M_r + r(1 + M_r) + 1) - R_p = 0 \tag{18}$$

where:

$$\gamma = \left(1 - \left(\frac{A_2}{A_1}\right)^2\right) \tag{18a}$$

This equation becomes the same as equation 17 if $A_1$ is much larger than $A_2$. By selecting the head pressure and the area ratio, the exit velocity and the mixing ratio of delivery system can be independently controlled.

The non-educting stream tube shown in FIGS. 25 and 33 allows further control of the mixing ratio with the use of only one tap. The neckdown ratio $A_1/A_2$ corresponding to $A_{in}/A_{out}$ in FIG. 33 governs the mixing ratio here if the reservoir is brought up to head pressure. The mixing ratio for this configuration can be written as:

$$(r^2 M_r + r(1 + M_r) + 1)\left(\frac{A_1}{A_2}\right)^2 - R_p = 0 \tag{19}$$

We can see that this reverts back to the same mixing ratio formula for the uniform diameter stream tube if $A_1$ equals $A_2$. For both of these equations, the positive root is the physically meaningful value r.

If a piston is used as an especially preferred embodiment, it is important that the piston diameter be large enough so that the rate of rise of pressure is rapid enough to generate the stream tube velocities needed to meter and eject the liquid or powder. The gas is allowed to escape continuously throughout the travel of the piston. If the piston diameter is too small, then the travel velocity must be very rapid in order to generate the pressure rapidly. For an exit orifice of 18 mils diameter (diameter of final diameter where mixing with the ophthalmic fluid takes place) in the most preferred embodiment, it was found that 0.15" diameter piston would not satisfactorily generate the rapid pressure rise needed, while a piston sizes larger than 0.5" in diameter and up to 0.75" in diameter were generally satisfactory. In order to generate the pressure rise sufficiently rapidly to provide sufficient gas velocity for repeated reliable delivery of uniform quantities of ophthalmic fluid, the travel velocity of the 0.15" diameter piston needed to be too large to be practical for inexpensive components such as syringe pistons. The piston diameter must not be too large, since, for a given force on the piston, the maximum pressure that can be generated is inversely proportional to the area of the piston.

These methods disclosed here are capable of delivering small quantities of material in a preselected amount of from about 1 nanogram to 1000 micrograms for powder or from 1 nanoliter to 100 microliters of liquid, or a combination of liquid and powder. Furthermore, the mixing ratios range for liquid from about 0.003 to 300 parts of gas per every part of liquid by weight, and 0.1 to 20,000 parts of gas per every part of powder by weight.

DETAILED DESCRIPTION OF MOST PREFERRED EMBODIMENT

The most preferred Inventive Device ID 150 of this Application comprises a hollow, cylindrical, Main Body 151 shown in FIGS. 13, 14, and 21 consisting of: (1) Piston Housing 151A (with a Hollow Cylindrical Interior 151E shown in FIG. 20), hollow cylindrical First Spring Housing 151B (piston guide) and hollow cylindrical Second Spring Housing 151C .(That is each Housing has a slightly decreasing cross-sectional area from the preceding one, (although Hollow Cylindrical Interior 151E is the same cross-sectional diameter for all said Housings, except for Housing 151A also shown in FIG. 20, which has an upward, outward internal taper.) Thus, each of the B and C Housings are step-downs from the preceding Housing and all have the same interior cross-sectional diameter (the reasons for this configuration are fully set forth below) and (2) Ejector Head 152 (all as shown in FIG. 13), which is 1.07" in length.

All of the foregoing components were fabricated out of PVC round stock, as well as other components to be described later herein. Acrylic round stock, as well as small quantities of thermoplastics, such as polyethylene were also used, as will be described in detail as follows. All the materials described herein were purchased at regular retail outlets.

The description of this most preferred embodiment and variations thereof is in connection with FIGS. 13 to 35 of the drawings. There may appear to be specific commonality with elements shown in preceding drawings of this Application. Actually there is no such specific commonality and even if such elements have a common name, such as spring, they will be expressly referenced in the description which follows with different numbers or letters, but there is generic commonality.

The major individual components of ID 150 were fabricated by using standard lathing, drilling and machine techniques on the PVC, Acrylic and Polyethylene pieces. (For instance the step-downs described for the said Housings above were accomplished by lathing the bottom portion of Housing 151A into smaller concentric step-downs.) PVC was chosen as the construction material for Housing 151A, First Spring Housing 151B, Second Spring Housing 151C, and Ejector Head 152 (0.76" in diameter and 1.07" in length) comprising all major elements of ID 150 (3.34" in length and 0.9" in diameter at its widest cross-sectional location at Housing 151A) of this preferred apparatus. This is because PVC was readily available, relatively inexpensive, easily machined and was easily bonded with adhesives to itself and to other components to result in the necessary water-tight and air-tight constructions.

Notwithstanding the use of machining techniques on PVC to fabricate this described most-preferred-embodiment, as well as embodiments previously described, it is to be understood that inventive apparatuses within the scope of the invention can also be fabricated from other widely available plastics, such as thermoplastic materials such as polyethylene, polypropylene and polystyrene by injection molding in a suitably designed mold. And machining can be done on other plastics such as polycarbonates.

The following discussion of ID 150 refers to the Material Reservoir 171 as Liquid reservoir 171. It should be understood that although liquid is specifically referred to, powder could also be used. Thus, Reservoir 171 could also contain a powder for delivery. This also applies to reservoir 171A, 179A, 179B, 1613, and 1614, and any other similar material reservoirs discussed herein.

Special elements that were selected and integrated into a whole to result in ID 150 as highlighted in FIGS. 13,14,15, 16,17,18,19,20,21,22,23, and 27 comprised the following:

1. The Spring 153 for ID 150 is a stainless spring steel about 0.44 inches in diameter and 0.75 inches long. It was a shortened version of a spring originally about one inch long. The untrimmed one inch version is equally satisfactory for use in the invention if the Spring Housing 151C is extended.

Several springs were purchased at a local hardware store and the appropriate length was only decided upon after trying at least six different springs, before it was established that this particular size and configuration would satisfy the many other requirements of the ID 150 so it would satisfy performance goals for this described preferred apparatus.

Figure 16A:
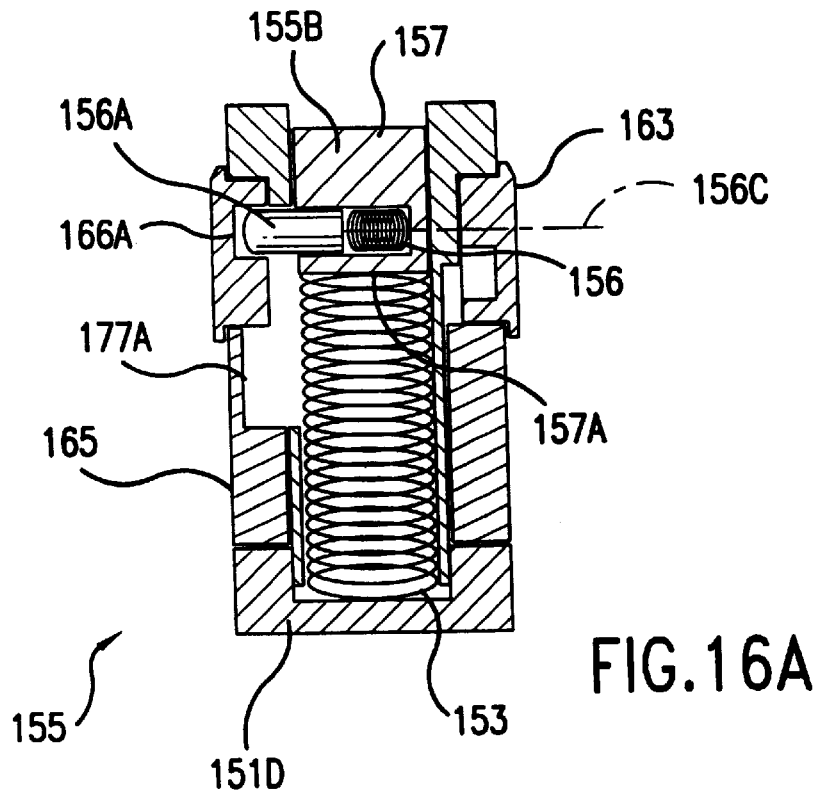
FIG. 16 Latching Means Assembly
Figure 16B:
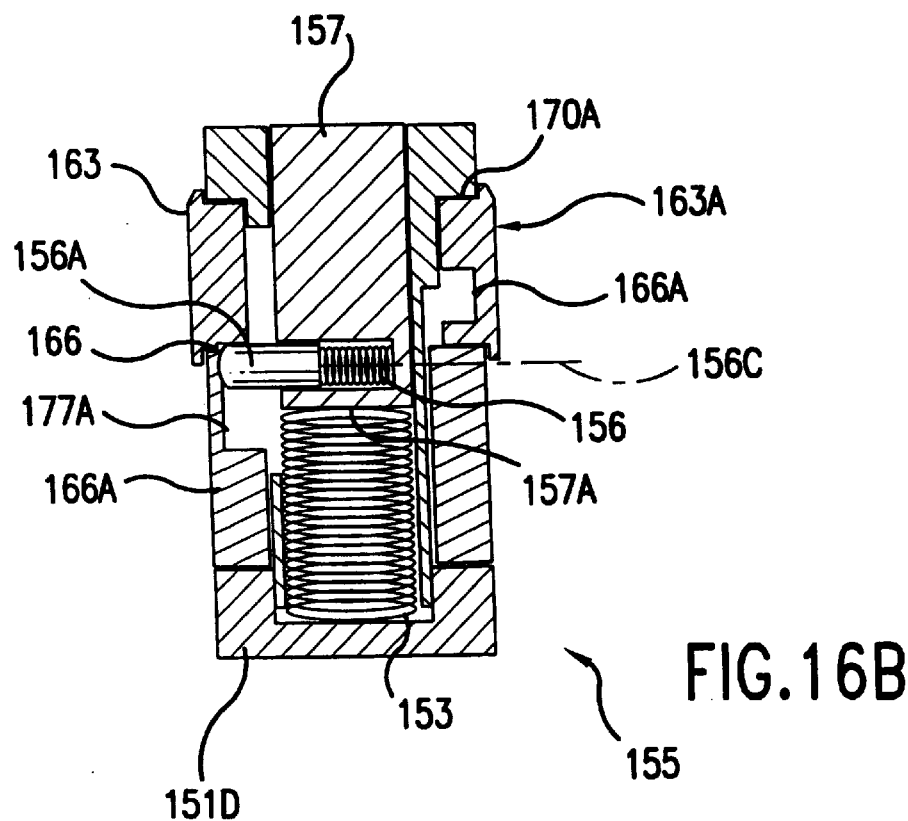
Figure 17A:
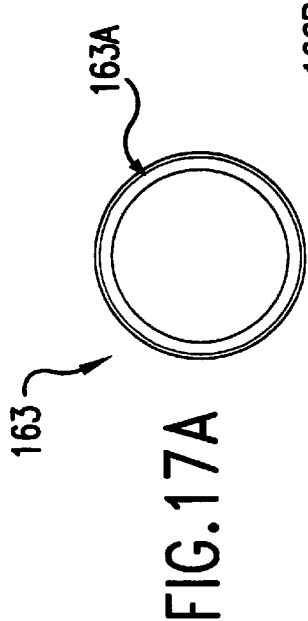
FIG. 17 Twist Ring
Figure 17B:
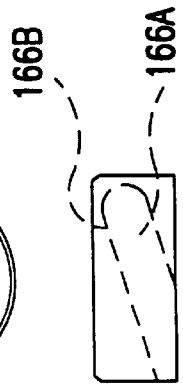
Figure 18:
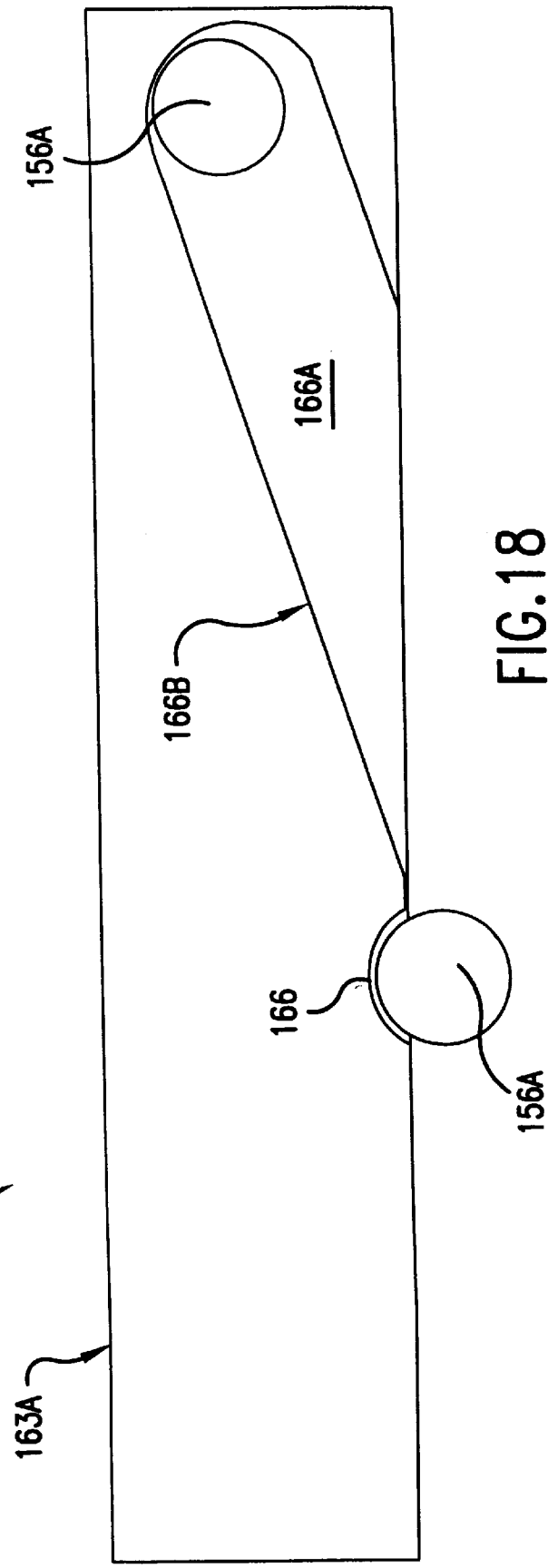
FIG. 18 Interior Portion of Twist Ring

2. Piston 154 consisted of a PVC shaft 0.5" in diameter and about 1.5" in length and was machined from an ordinary, purchased PVC rod. Piston 154 is movingly installed in Housing 151A, Hollow Cylindrical First Spring Housing 151B and Hollow Cylindrical Second Spring Housing 151C. The lower portion of Piston 154 consists of Shaft 157 and the Bottom Surface 157A of Shaft 157 is on top of Spring 153, with Latching Means Assembly 155 associated therewith as shown in FIG. 16 including Slot 154A, Small Latch Spring 156 and Latching Pin 156A all within Spring Housings 151B and 151C.

3. The outside of Spring Housing 151B extends concentrically from the bottom end of Housing 151A after being lathed to reduce its outer diameter from the starting rod of PVC thereby forming 151A to have about a ¼" less outer diameter than the outer diameter of Housing 151B.

This starting rod was about 3.5" long and was hollowed out (151E) so the same inner cylinder dimensions prevail throughout said Housings except for Housing 151A and being sufficiently sized to contain the Spring 153 and Piston 154. Spring Housing 151C was made in a similar manner to Spring Housing 151B. Spring Housing 151C also extends concentrically from Spring Housing 151B and has the same inner hollow cylindrical dimension.

Figure 14A:
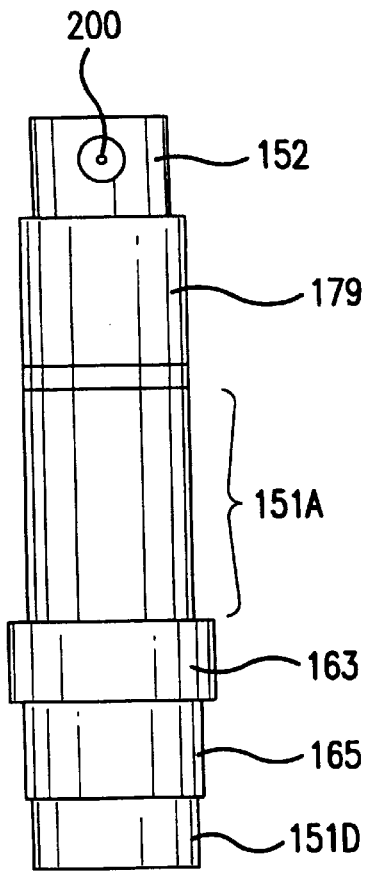
FIG. 14 is the device body (ID150) with rings and caps
Figure 14B:
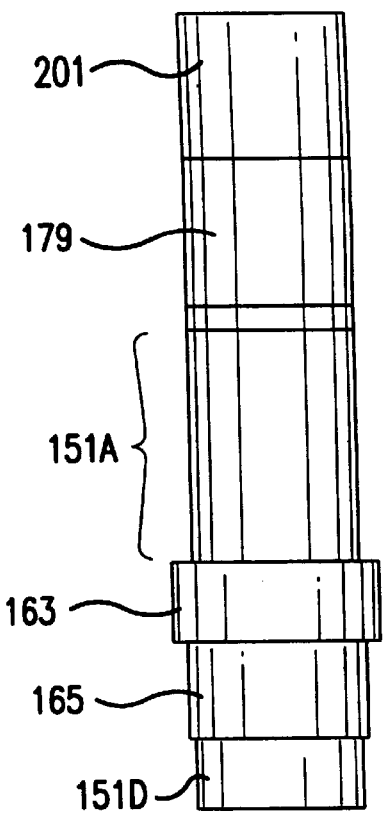
Figure 14C:
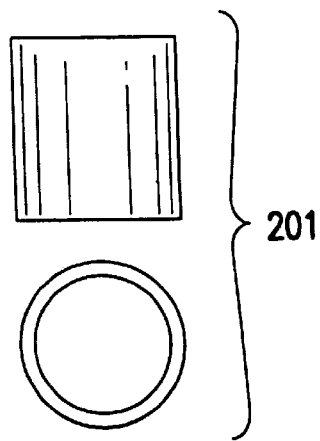

Spring Housing 151C is closed off at its bottom end by sealing with Housing Cap 151D (FIG. 14). Cap 151D also serves the additional functions of supporting Spring 153 as well as certain Ring configurations for actuating release of Spring 153, as will be detailed below. The Cap 151D can be made so that the spring Housings are effectively longer by making such Cap 151D deeper. This imparts great flexibility to spring selection The net effect of this assemblage is a continuous Hollow Cylindrical Interior 151E, except for 151A within the assemblage of stepped Housings A, B and C. Piston 154, which is located above Spring 153 is snugly and operatively engaged within said Housings.

4. A vertical open slot 154A about ½" in length and ¼" wide was cut in the longitudinal direction extending upwardly from the bottom of Spring Housing 151B and downwardly from the top of Spring Housing 151C . This Slot accommodates both the up and down movement of Latching Pin 156A and the in and out horizontal movement of Latch Pin 156A.

5. The bottom of Piston 154 is designated as Shaft 157 in which Horizontal Notch 155B is drilled with a less than about 0.25" cross-section. This Notch 155B contains Latching Pin 156A, which compresses Small Spring 156, which Spring 156 rests against the interior end of said Notch 155B.

The total Latching Assembly Means 155 comprises Horizontal Latching Pin 156A (approximately 0.2" in diameter and 0.35" long), Small Spring 156 (less than about 0.2" in and 0.15" in diameter) adapted and constructed to be inserted into Notch 155B and to be compressed by the inward movement of Latching Pin 156A as it is cammed downwardly, all as part of Latching Means Assembly 155.

Latch Pin 156A in Notch 155B is perpendicular to Piston 154 and Shaft 157 as shown in FIG. 16. When Piston 154 is in its up or down travel mode, Latch Pin 156A will move upwardly or downwardly in Slot 154A. The axis 156C of Latch Spring 156 or the center of Notch 155B was located about 0.15" from the Bottom 157A of the Shaft 157 of Piston 154. Such Bottom 157A is in direct contact with the top of Spring 153 and is the part of Piston 154, which receives the momentum to be forcibly moved by Spring 153.

Figure 20A:
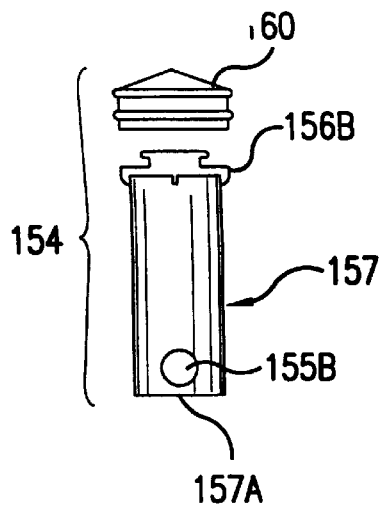
FIG. 20 Piston, Main Body, Latch Pin, Latch Pin Spring
Figure 20B:
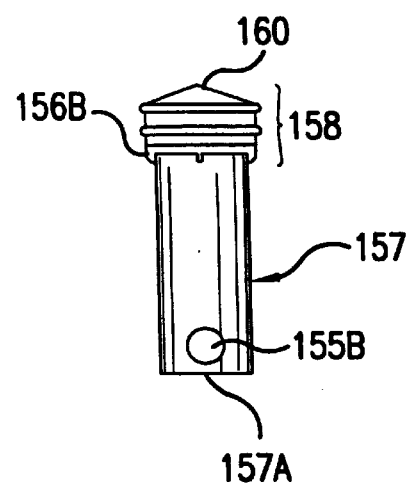
Figure 20D:
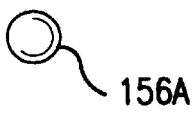
Figure 20E:
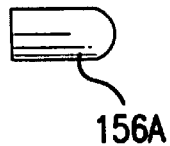
Figure 20F:
Figure 20G:
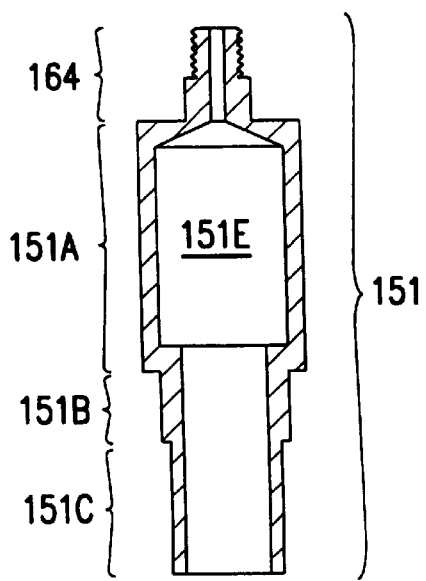
Figure 20H:
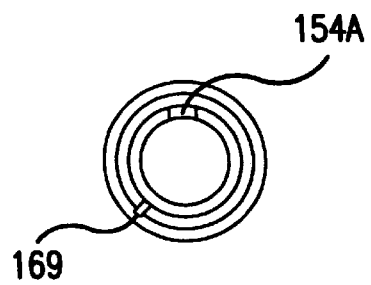
Figure 21A:
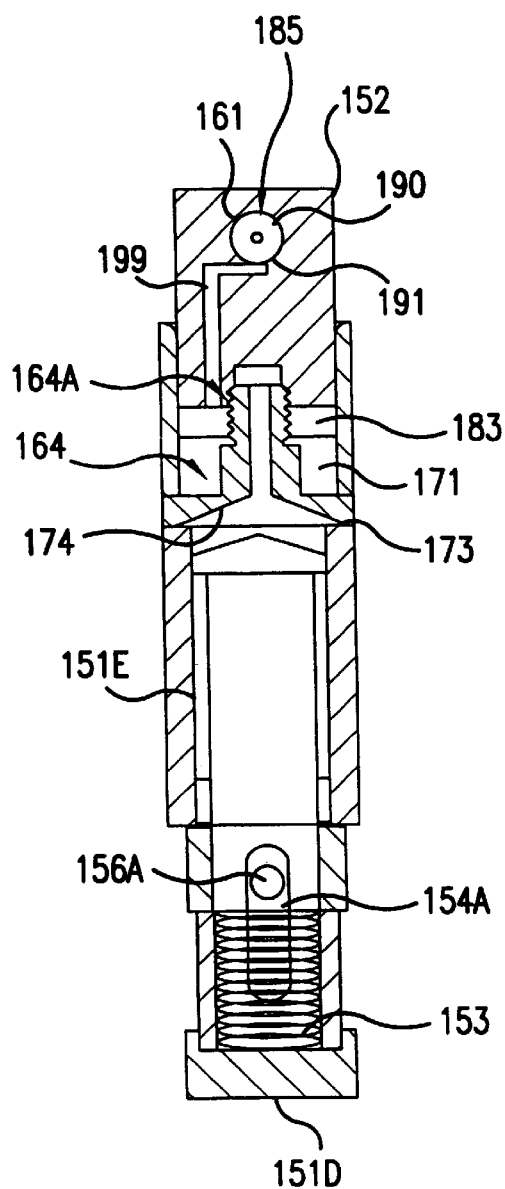
FIG. 21 Cutaway Views of ID 150
Figure 21B:
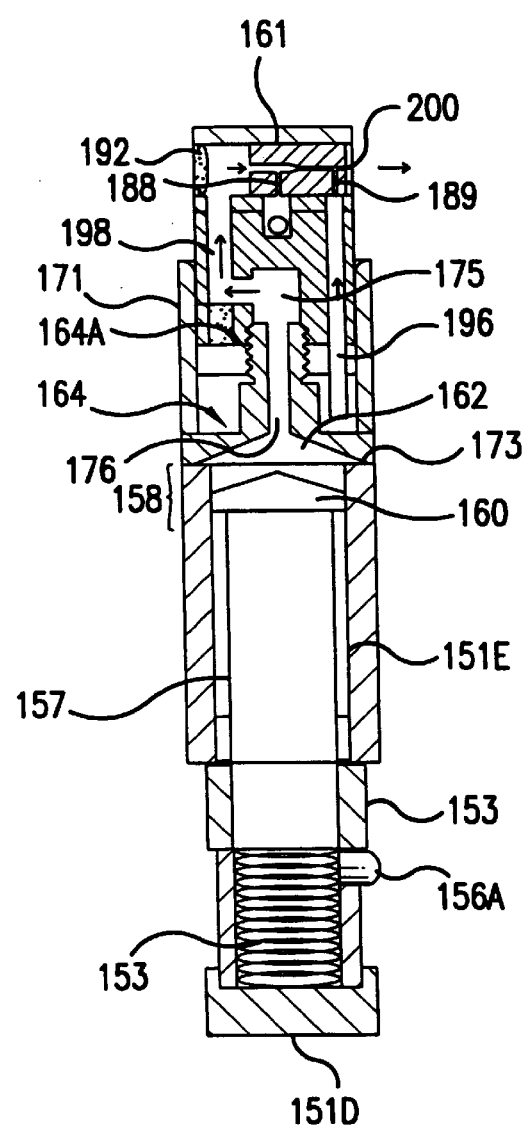
Figure 22A:
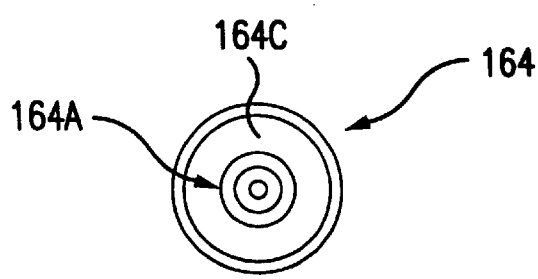
FIG. 22 Four Way Lug with Reservoir
Figure 22B:
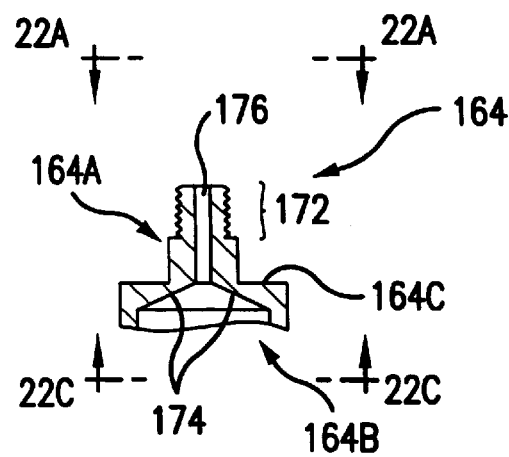
Figure 22C:
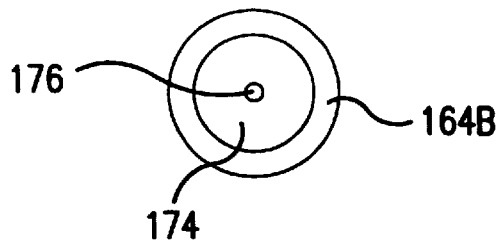
Figure 22D:
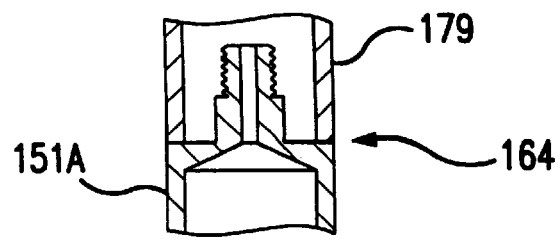
Figure 23A:
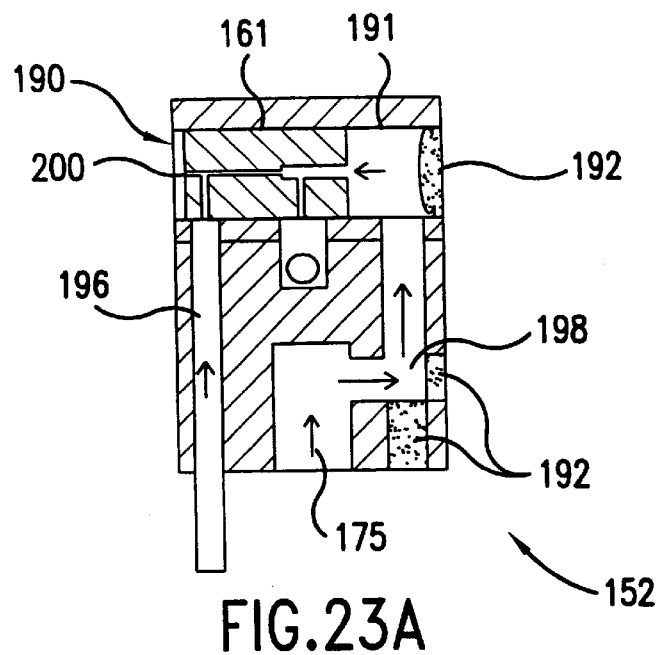
FIG. 23 Ejector Head and Cutaway Views
Figure 23B:
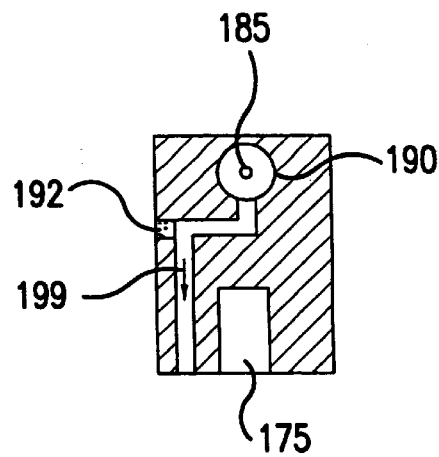
Figure 23C:
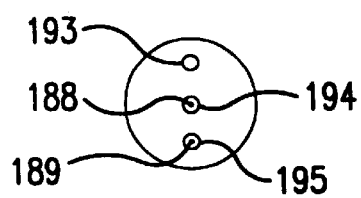
Figure 23D:
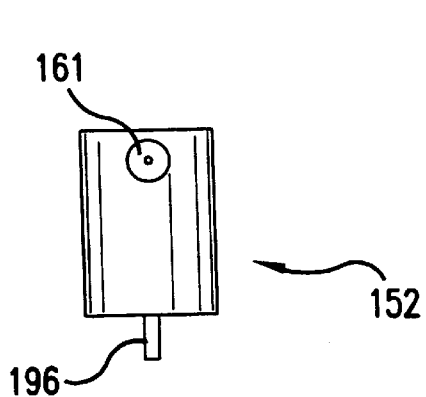
Figure 23E:
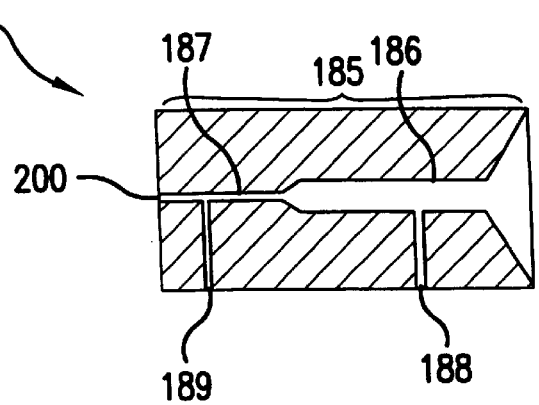

6. In FIGS. 20A, and 21 Piston 154 has a Top Portion 158 provided with Air Sealing means 159 made from a Latex Cap 160 attached to a Polyethylene Tip 156B. Both Tip 156B and Latex Cap 160 were obtained by removing them from a commercially available glue syringe obtained from a hobby store. Tip 156B was fixedly glued to the top of Shaft 157. Latex Cap 160 was snug fitted in an airtight fashion within the Continuous Hollow 151E. Tip 156B and Latex Cap 160 form Top 158 of the piston.

The selection of the correct Piston 154 diameter required experimentation and selection judgment before a choice was made from several possible options. The size of Latex Cap 160 was chosen to be about 0.635" in diameter. This choice was a result of a trade-off between being small enough to fit within a 0.9" inner diameter cylinder to move Latex Cap 160, and being large enough to provide a desired 1 to 2 milliliters (ml) of air with minimal travel of Piston 154.

The volume or amount of gas, preferably air chosen for processing in the apparatus ID 150 is central to the delivery of the preselected amount of fluid. It has been determined and is a feature of this invention that the pressure head and quantity of propulsion gas for each action of Piston 154 should be matched to the diameter of the Stream Tube 161 shown in FIGS. 21, 23 and 27 in order to flow through the ID 150 apparatus in about 0.5 to 1 second (short times are essential) in response to the movement of the Piston 154 when the pressure on Spring 153 is released.

A piston substantially larger than the one chosen will provide insufficient maximum high pressure head required for the need required by the ID 150 apparatus. If the piston is substantially smaller than the one chosen, the rate of gas pressure rise is too slow for proper operation of the apparatus.

7. The size of Gas Reservoir 162 is chosen so that it is not small compared with the Fluid Reservoir 171.

8. TWIST RING AND RELEASE RING—Latch Pin 156A is under Twist Ring 163 and Release Ring 165 which in the cocked or loaded position(Shown in FIGS. 14,15,16, 17,18, and 20). Piston 154 is pulled downward by Twist Ring 163 as Twist Ring Camming Surface 166B pushes Latching Pin 156A downward into Holding Notch 177A of Release Ring 165. When ID 150 is cocked by action of Twist Ring 163, Latching Pin 156A is held both in Notch 166 of the Twist Ring, and simultaneously in Holding Notch 177A.

This in effect locks Latch Pin 156A into the compressed or loaded position (cocked) in Latch Pin Holding Notch 177A of Release Ring 165 and keeps Spring 153 and Piston 154 in Spring 153 biased (loaded) position.

Notch 177A is part of Camming Surface 168 on the inner surface of Release Ring 165 and covers Latching Pin 156A when Piston 154 is held in its restraining position by Notch 166 of Twist Ring 163. The force on Twist Ring 163 is communicated to the Main Body 151 through the upper surface 163A of Twist Ring 163. Surface 163A contacts shoulder 170A of the main body and holds Twist Ring 163 in place.

When Latching Pin 156A is released from its holding position in Notch 166, by a turn of Release Ring 165, which moves Camming Surface 168 so that it displaces Latching Pin 156A out of Notch 166 in Twist Ring 163 in an inwardly direction, the holding force on Spring 153 is released.

Spring 153 thereby suddenly displaces Piston 154 forcibly upwards within Hollow Cylindrical Interior 151E. Latching Pin 156A after being forced inwardly by Release Ring 165 travels upwardly through Slot 154A. Gas (air) under the suitable preselected pressure head generated by the interaction of the Piston 154 and Spring 153 travels through the ID 150 apparatus and entrains or induces a suitable amount of liquid from a liquid reservoir (described below), which in combination with the entraining gas exits from the ID 150 and strikes a selected target. All of which will be described below in additional detail.

When Piston 154 is moving in this upward direction the outside of Latching Pin 156A moves up on the inside wall of Twist Ring 163. Rings 163 and 165 are slightly larger in diameter than the diameter of Spring Housings 151B and 151C, on which they are rotatably mounted, (that is about 0.125" greater diameter than for each of said Housings 151B and 151C.)

Twist Ring 163 is engaged in place by Release Ring 165, which is held in place by Cap 151D. Horizontal Lug 169 is a small horizontally projecting lug configuration which is fitted on Housing 151C and engages Ring Limiting Cut 167 in Release Ring 165. Horizontal lug 169 prevents Release Ring 165 from excessive horizontal rotational movement. The outer diameters of Twist Ring 163 is about 1.03", that of Release Ring 165 is about 0.965" and that of Housing 151A is 0.9".

The top of Twist Ring 163 must not only withstand the force of Spring 153 transmitted through Latch Pin 156A, Twist Ring Camming Surface 166B, and Twist Ring Notch 166 as it is compressed and cocked to drive Piston 154, but it still must be able to rotate on Housing 151B with little resistance. Accordingly, some friction reducing means is optionally but preferably employed. In this preferred embodiment (FIG. 13, and 14) a strip of Teflon Tape 170 is inserted appropriately in the Shoulder 170A between Housing 151A and Housing 151B so that the top of Twist Ring 163 (FIGS. 13 and 21) in contact therewith under pressure is still able to accomplish the purpose of easy horizontal movement when in contact with such Shoulder 170A.

Figure 15A:
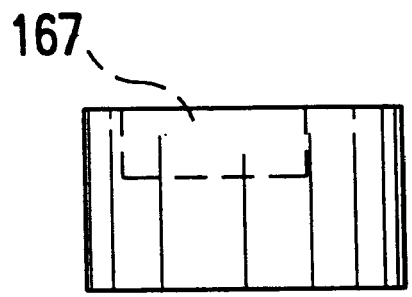
FIG. 15 shows the Release Ring
Figure 15B:
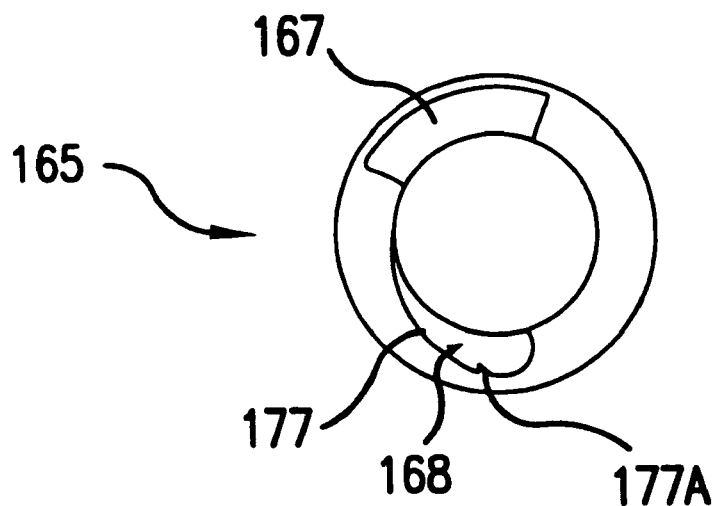
Figure 15C:
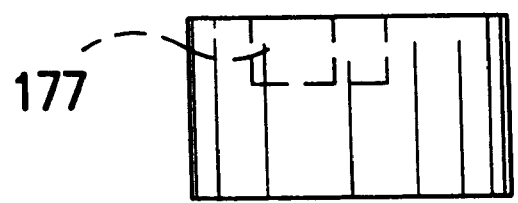

Release Ring 165 is 0.56" in height. It is rotatably mounted on Housing 151C just below Twist Ring 163. FIG. 15 shows a cross-sectional horizontal cut of Release Ring 165 in which Radial Camming Surface 168 and Rotation Limiting Groove 167 are illustrated. Rotation Limiting Groove 167 is provided on the inner surface of Release Ring 165 to engage Horizontal Lug 169 (FIG. 13, 20) located from 130 to 180 degrees of rotation from Slot 154A so that only about 90 degrees of rotation are allowed, which thereby restricts the vertical movement of Release Ring 165.

When Release Ring 165 is twisted, Pin 156A is released from Notch 166. When Pin 156A is released there is no restraint to hold Piston 154 in place and Spring 153 expands rapidly driving Piston 154 which compresses a predetermined amount of gas for delivery under pressure to Stream Tube 161. When released, Pin 156A rides up in Slot 154A against the inside of Twist Ring 163.

It is to be noted that as one inventive feature, an oversize Spring 153 was selected. This was done deliberately as a result of an inventive selection, so that the entire expansion capacity of the spring is not utilized in the apparatus. Only a portion thereof is used. Thus, after the total volume of gas has been delivered Spring 153 still has unused compression capacity. By the same token Spring 153 is not compressed to the ultimate degree possible prior to its release to drive Piston 154.

9. RESERVOIR ASSEMBLY AND FEEDER TUBE TO CONVEY AIR(GAS) TO ID 150'S EJECTOR HEAD 152.

FIGS. 21,22, and 23 are applicable to the description that follows. Liquid Reservoir 171 was formed from specially constructed 4-Way Lug 164 made from a solid PVC cylinder by creating a Nipple 164A with upper threaded Hollowed outer Portion 172 therein, having an outer diameter of about 0.25" at its narrowest and 0.9" at the widest part of Lug 164 and an inner diameter of approximately 0.09" after being hollowed out to form inner passage 176. The diameter of the Upper Threaded Portion 172 of the small upper dimension was about 0.3". The 4-way Lug 164 was rigidly glued to the Top 173 of housing 151A and also served as Piston Closure Cap 174, as well as providing the threaded portion 172 for attaching into Threaded Portion 180A of Air Feed Conduit 175 in Ejector Head 152.

Air Feed Conduit 175 consists of Threaded Portion 180A, and Upper Portion 175A which connects to L-shaped Conduit 198. Threaded Portion 180A shown in FIG. 27 has mating threads for Threaded Upper Portion 172 of Nipple 164A.

And the upper concentric outer lap portion 164C of 4-way lug 164 also serves as the base of Liquid Reservoir 171. The bottom portion of 4-way lug 164 is hollowed and shaped to house the upper portion of Latex Cap 160, which has been fitted to the top of Piston 154 by means of polyethylene tip 156B.

Air Feed Conduit 175 was drilled into Ejector Head 152 to connect with Gas Reservoir 162 so that an air or gas passage was created through the length of Ejector Head 152, so that gas or air could pass through Ejector Head 152, which is attached onto the Upper Threaded Portion 172 of Nipple 164A by Threaded Portion 180A of Conduit 175.

Figure 27:
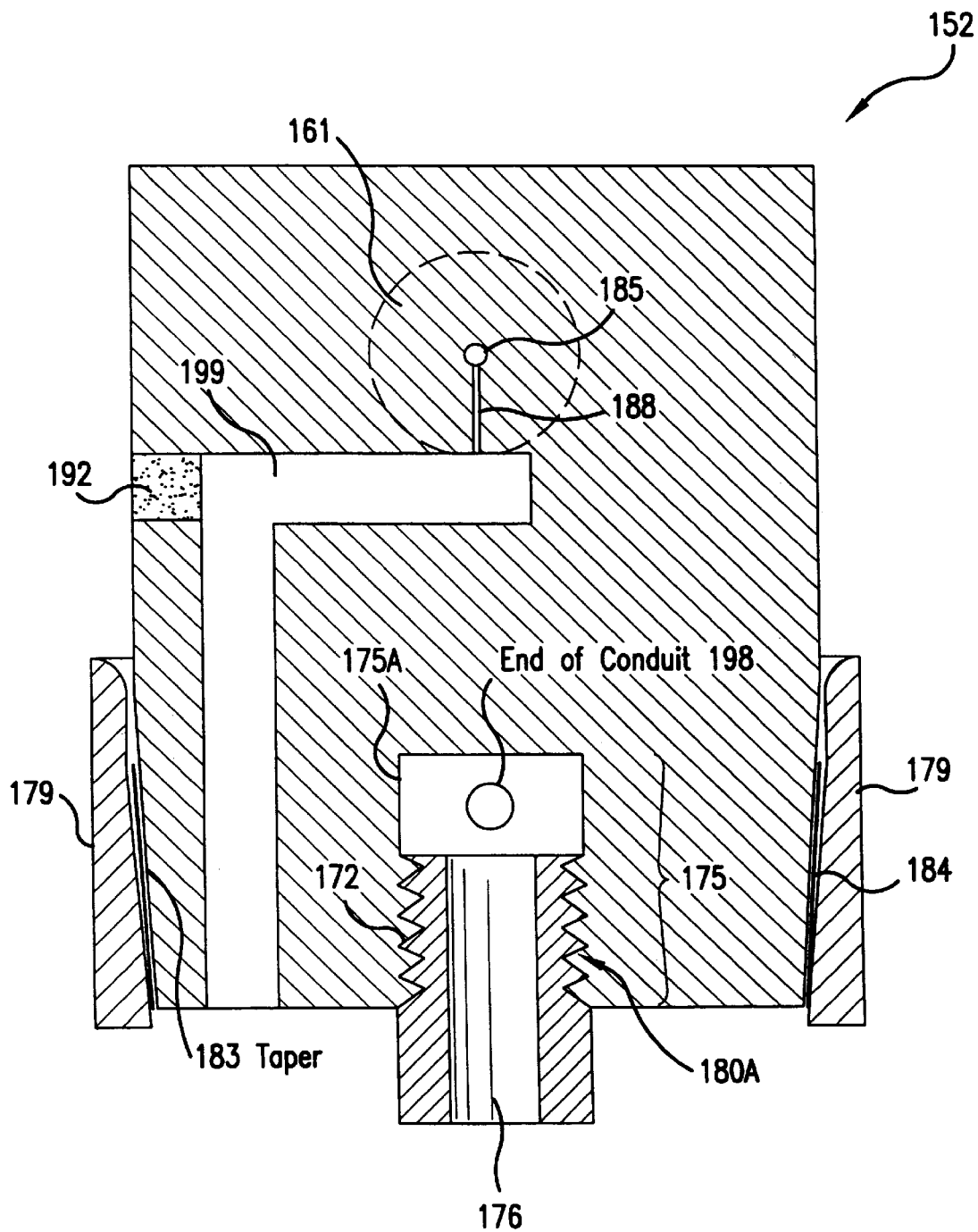
FIG. 27 Magnified Cutaway View of Ejector Head
Figure 28:
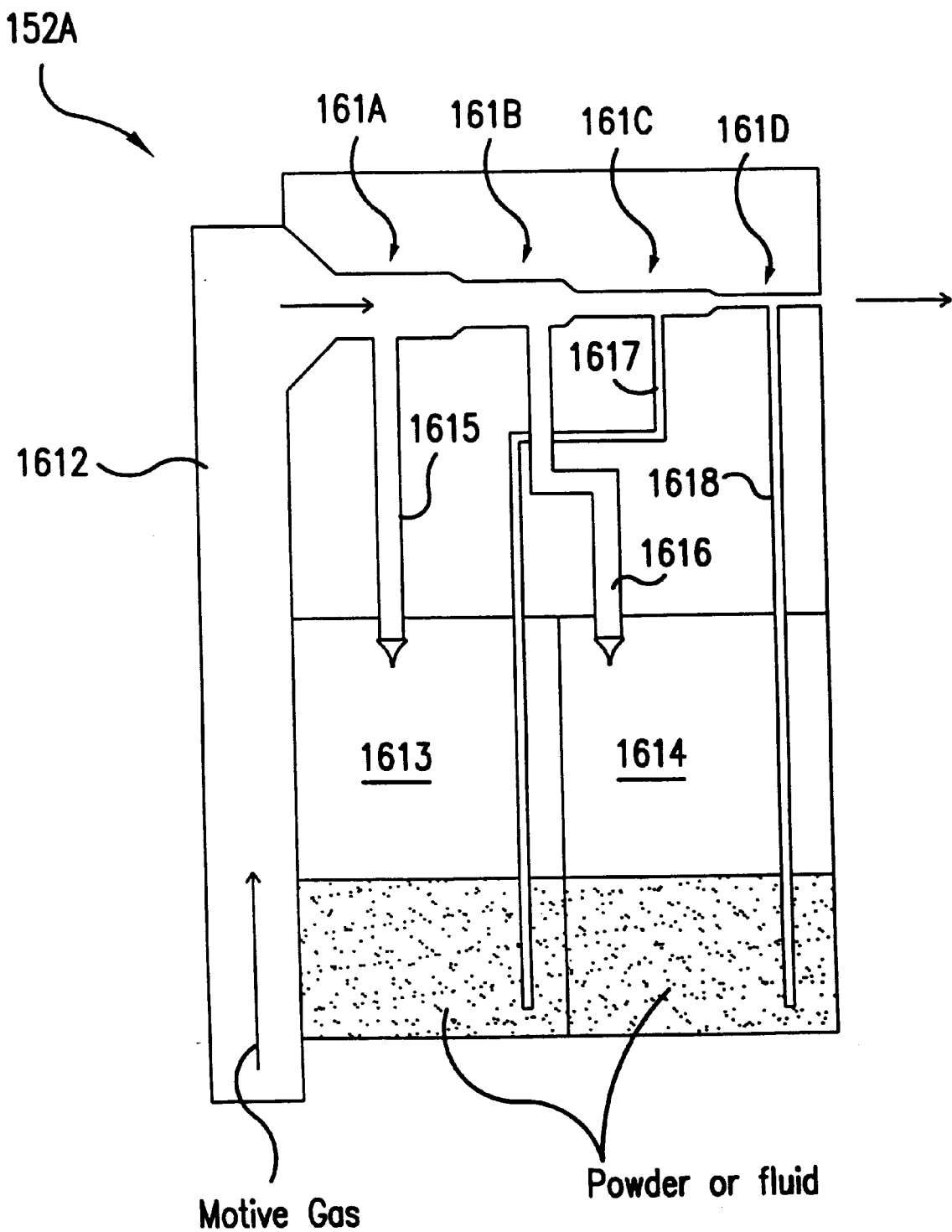
FIG. 28 Series Stream Tube with Dual Reservoirs
Figure 29:
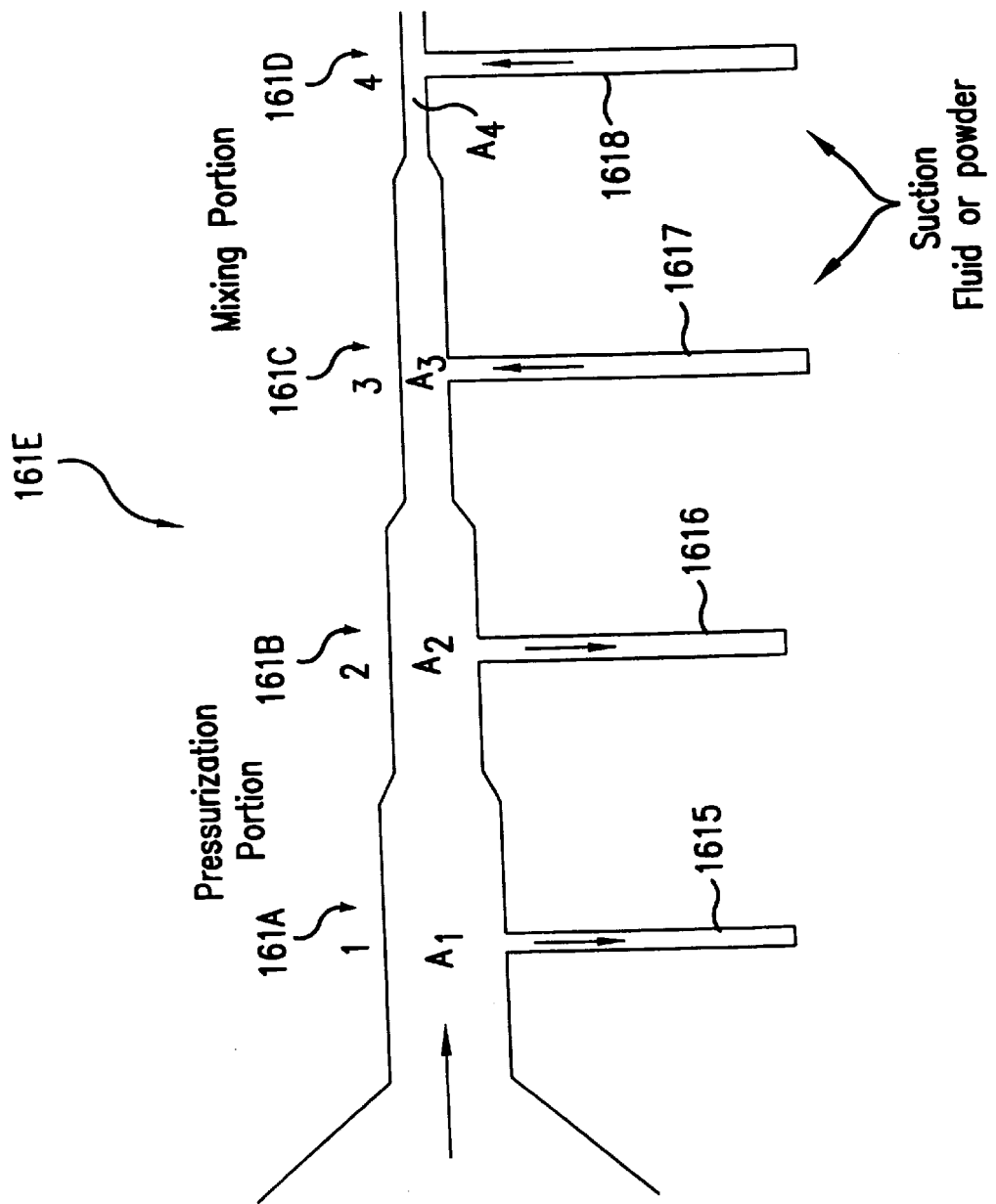
FIG. 29 Magnified View of Series Stream Tube

Reservoir wall 179 has Top 180 which contains Taper 181. This permits the outer diameter 182 of Bottom 183 of Ejector Head 152 to seal with Top 180 as shown in FIG. 27. FIG. 27 shows a cutway, front view of the Ejector Head 152 with the cutaway plane through the middle of Ejector Head 152.

Ejector Head 152 has reciprocal or matching ¼"-20 threads in Threaded Portion 180A that permit attachment of Ejector head 152 to Nipple 164A, which also connects Air Feed Conduit 175 to Conduit 176. Conduit 175 communicates through Air Feed Conduit 176 with Gas Reservoir 162. When Ejector Head 152 is tightly screwed onto the Threaded upper portion 172 of Nipple 164A, the result is a necessary air-tight seal.

A new portion of Teflon Tape 184 is wrapped around Bottom 183 of Ejector Head 152 to assist in making an air-tight seal against the Tapered Inner Wall 181 of Reservoir Wall 179.

10. EJECTOR HEAD

As shown in FIGS. 21, 23, and 27 Ejector Head 152 (¾" OD PVC) contains Confluence Orifice 190 (about ¼" in diameter) suitable for housing Stream Tube 161 (0.5" long), which Tube 161 (FIG. 23) serves the function of mixing and ejecting liquid from Liquid Reservoir 171 and air (gas) from Gas Reservoir 162. Stream Tube 161 has Axial Conduit 185 connecting each of its ends. First Chamber 186 (20 to 40 thousandths of an inch in diameter and Second Chamber 187 (10 to 15 thousandths of an inch in diameter) each are components of this Axial Conduit 185 with its connecting bottom pointing orifices, which are designated as First Tap 188 and Second Tap 189.

First Tap 188 is provided to pressure the Liquid Reservoir 171 (FIG. 21) in a preselected pressure mode. Such pressurization of the internal portion of Reservoir 171 (FIG. 21) aids the removal of liquid from Reservoir 171 by helping or assisting in the overcoming of the liquid-surface and liquid—liquid adhesion forces that tend to make most liquids have initial resistance to removal from their reservoirs or from tubes connecting to such reservoirs.

Second Tap 189 conveys a preselected amount of liquid from Reservoir 171 to be entrained within air passing within Chamber 187 and then ejected therefrom to a target. The degree of mixing within Chamber 187 is dependent on many factors, including the viscosity and density of the entrained liquid, the velocity of the air flow and the air pressure at the time of entrainment and the cross-sectional diameters of Chambers 187 and 186.

As has been described elsewhere herein, for the process aspects of this invention, it has been discovered that the relationship between the amount of a given unit of gas passing through Axial Conduit 185 and the liquid from Liquid Reservoir 171 to be entrained by such gas unit is referred to as the mixing ratio.

This connection between gas amounts and liquid amounts can be used to select the desired amount of liquid to be entrained and emitted from ID 150 through Exit Orifice 200 with the given quantity of gas selected. Whatever mixing ratio is desired within the operating limits of a given apparatus of this invention, it is controlled by a novel and unobvious combination of several interactive factors including the propulsive force provided by Spring 153 on Piston 154 generating a propulsion gas which in turn is regulated by the size as determined for the diameters of First Chamber 186 and Second Chamber 187.

The properties of the conveyed material, such as a fluid will also influence these interactive factors. Propulsive gas can also be supplied by exterior sources, such as pressurized gas canisters, a $CO_2$ cartridge being one example. Even the action of a simple hand-operated syringe was useful when pushed rapidly enough, as shown by the Examples of this Application.

Stream Tube 161 (FIGS. 13, 14, 21, 23, and 27) is a subcombination element, which can exist as a separate article on its own before incorporation into Ejector Head 152 or be directly drilled or molded into Ejector Head 152. A particular configuration for Stream Tube 161 is described immediately following. It is to be understood that various modifications of stream tubes can be effected, as taught herein, to obtain a range of selected quantities of emitted liquids of varying viscosities.

By the same token the amount of mixing in Second Chamber 187 can be controlled by a knowledge of these interdependent factors. Stream Tube 161 is approximately ½" in length.

In operation, it was installed into Confluence Orifice 190 drilled into Ejector Head 152. It was made from ¼" diameter transparent Acrylic round stock. Plastics capable of being injection molded such as various polyolefins would also be useable. Other drillable transparent plastics, such as polycarbonates or glass would be also be satisfactory.

Axial Conduit 185 is for conveying fluid and gas. It comprises First Chamber 186 (relatively large) and Second Chamber 187 (relatively small). It is drilled through the center axis of Stream Tube 161.

First Tap 188 was drilled perpendicular to First Chamber 186 and Second Tap 189 along the same line was drilled perpendicular to Chamber 187. First Tap 188 and Second Tap 189 have diameters of approximately 0.018" and provide connects from Chambers 186 and 187 respectively to Liquid Reservoir 171. First Chamber 186 has a diameter of about 0.03" and Second Chamber 187 has a diameter of about 0.014"

In the most preferable mode, the entry point of Second Chamber 187 is flared out about 2 times its diameter in a funnel-like cross sectional portion. The same flare configuration can be utilized for First Chamber 186 and it is flared about 4 times the diameter of the First Chamber 186.

First Tap 188 is connected to larger First Chamber 186, which in turn is connected to the air space above the liquid level in Liquid Reservoir 171. Tap 189 is connected to smaller Second Chamber 187 and its other end is ultimately connected to a conduit extending below the surface of the liquid level of Liquid Reservoir 171.

In the upper portion of Ejector Head 152, a conduit designated as Confluence Orifice 190 with Lower Portion 191 and somewhat smaller than ¼" in diameter is obtained after said upper portion is drilled through the entire ¾ diameter thereof. The Stream Tube 161 is either force-fitted into Confluence Orifice 190 or if more loosely fitted therein it can be glued to stabilize it. Stream Tube 161 occupies about ⅔ of the length of Confluence Orifice 190 at one end thereof At the other end of Confluence Orifice 190, away from Stream Tube 161's location therein, appropriate Sealing Means 192 (Ordinary glue) was used to seal all orifices obtained by drilling passageways through Ejector Head 152. However other sealants such as hot melts could be used. Sealants are provided so that Confluence Orifice 190 is no longer open at the end away from Stream Tube 161.

Three holes ¼" apart were drilled into the Bottom 191 of Confluence Orifice 190. These provide respectively: Orifice One 193 through which driving pressured air or gas is provided, Orifice Two 194 through which pressure for Liquid Reservoir 171 is provided (a preferred embodiment that can be accomplished in various ways, some of which are illustrated elsewhere in this Application) and Orifice Three 195 providing suction (through the difference between the reservoir pressure and the pressure in Chamber 187) the connecting means for removal of a preselected amount of liquid from Liquid Reservoir 171 for delivery to the target of ID 150 through Exit Orifice 200.

Orifices 194 and 195 are configured to join with and connect to Taps 188 and 189. It will be noted that Confluence Orifice 190 connects with various orifices and various taps and conduits between Steam Tube 161, Liquid Reservoir 171 and Gas Reservoir 162. Orifice One 193 provides access to provide for driving air or gas at the sealed end of Confluence Orifice 190. Orifice 193 is connected to an air pressure source, that is Gas Reservoir 162 (in this embodiment) by First L-Shaped Conduit 198, which in effect is an offset connection from the outer location of Confluence Orifice 190 to the center 176 of 4-way lug 164 where entry to Gas Reservoir 162 is located.

Conduit 198 is obtained by drilling two intersecting passageways through Ejector Head 152 and then gluing the entryways from the entering drill bit side with Sealing Means 192 to provide airtight seals with.

A similarly obtained, offset Second L-Shaped Conduit 199 (except that the short leg of the "L" is at the top of Ejector Head 152) configuration connects large First Chamber 186 to air space in Liquid Reservoir 171. The pressure supplied thereby within the Liquid Reservoir 171 permits displacement of the desired amount of liquid (by helping to overcome the previously described surface attractions for such liquid).

This displacement occurs from Liquid Reservoir 171 through Feeder Conduit 196, located below the liquid level of Reservoir 171, which Feeder Conduit 196 ultimately communicates with small Second Chamber 187.

11. IN OPERATION The particularly preferred embodiment of the invention described above was operated as follows: Two cubic centimeters (cc's) of Timolol XE™ a drug approved for ophthalmic use was inserted into Reservoir 171. The Spring was placed in the cocked position and released through Twist Ring 163. Air compressed by the Spring 153 driving Piston 154 was forced through the Conduit 176 in Lug 164 and Conduits 175 et al in Ejector Head 152. Fluid was thereby drawn out of Liquid Reservoir 171 in the quantity of about three microliters (3 ul) and delivered to a target about 2 inches away from Exit Orifice 200.

FIG. 24 shows a useful modification which could be incorporated into ID 150. FIGS. 24A and 24B show Pistons 204 and 205 with One-Way Valves 204A and 205A included in them. These one-way valves can serve at least two important functions. First, they allow air to flow in through the head of the piston into Gas Reservoir 162 or a similar gas reservoir when Pistons 204 or 205 are pulled downward to prepare for delivery of fluid or material. This prevents air from being pulled back through the mixing and pressurization conduits, such as Axial Conduit 185, and Chambers 186 and 187, and assures that the fluid or material in Feeder Conduit 196 or similar conduits is not displaced or moved as the piston is pulled downward to compress Spring 153, or any spring that might be used to drive the piston. One-Way Valve 204A is a flexible flap that will open and allow air to flow through the piston when the gas reservoir pressure is lower than the ambient pressure. During the upward stroke of Piston 204, the pressure closes valve 204A and prevents backwards air flow.

Figure 24A:
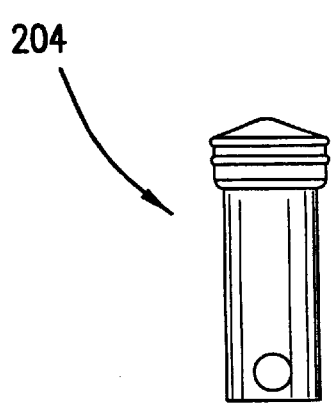
FIG. 24 Two Pistons with One Way Valves
Figure 24B:
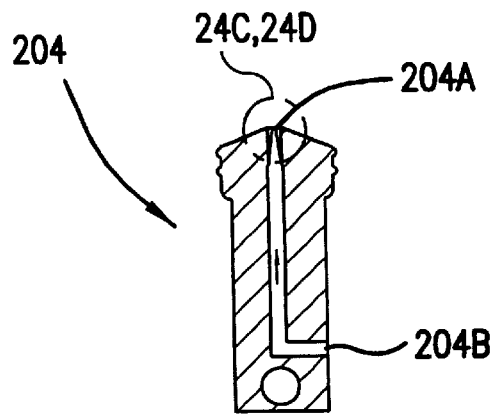
Figure 24C:
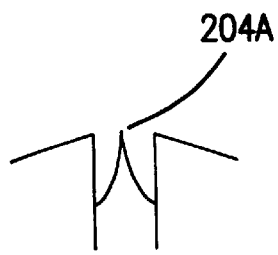
Figure 24D:
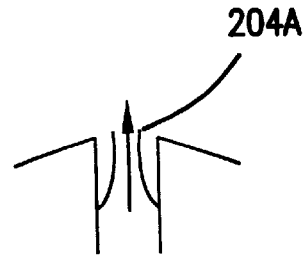
Figure 24E:
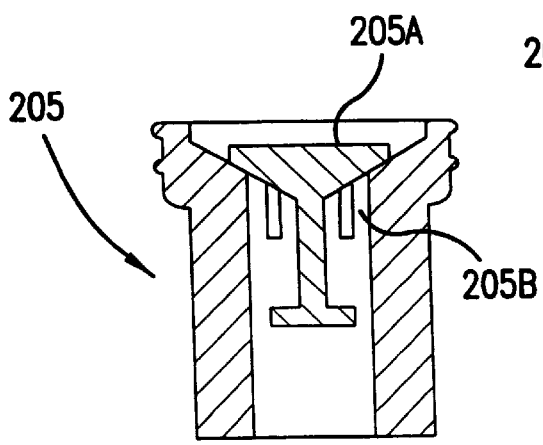
Figure 24F:
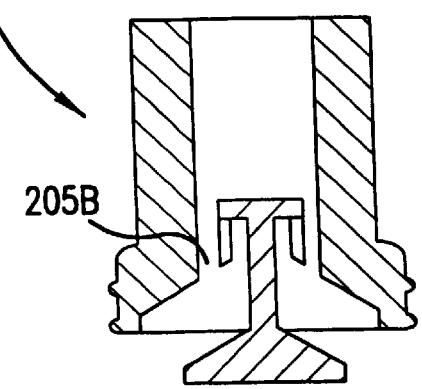
Figure 30A:
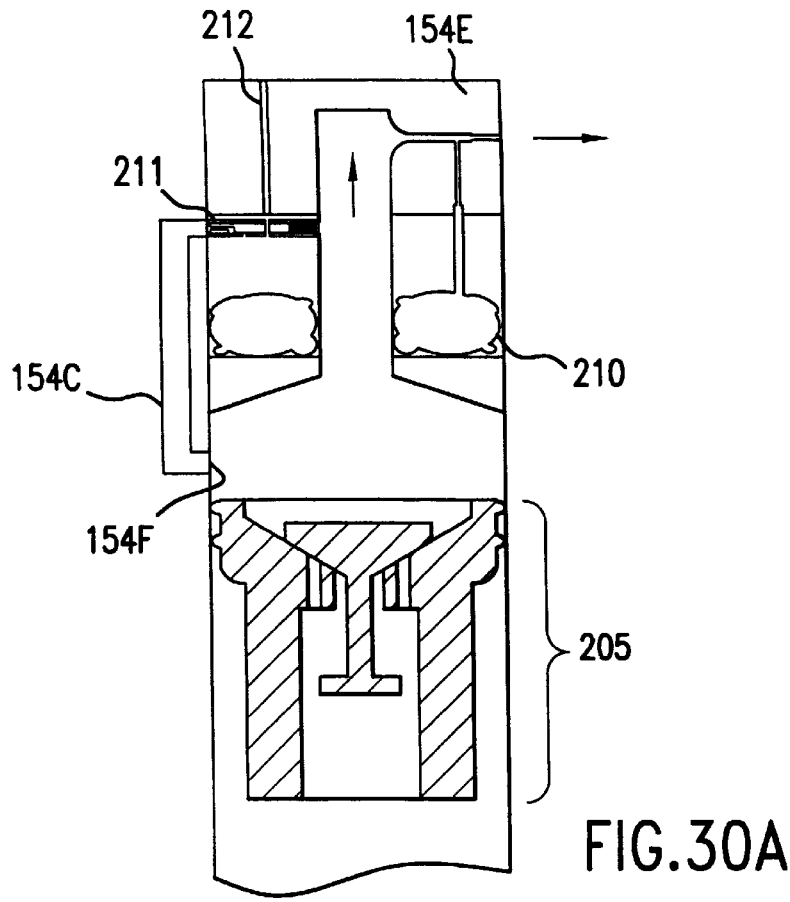
FIG. 30 Piston Cutoff With Two-Way Valve to Control Reservoir Pressure
Figure 30C:
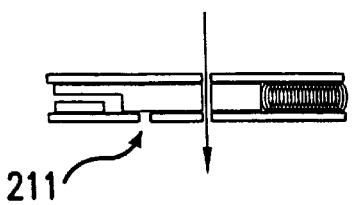
Figure 30D:
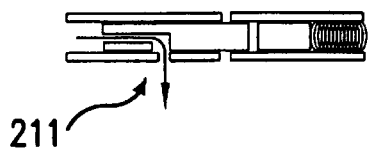
Figure 30B:
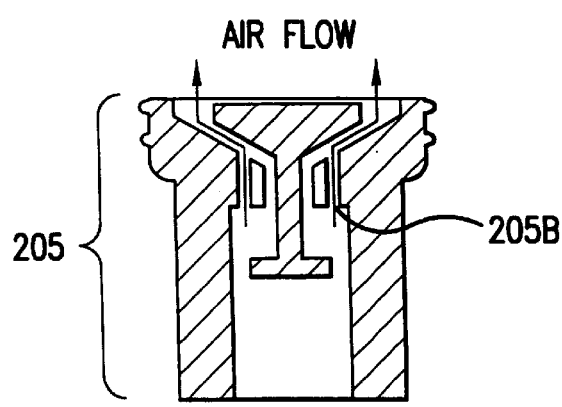
Figure 31A:
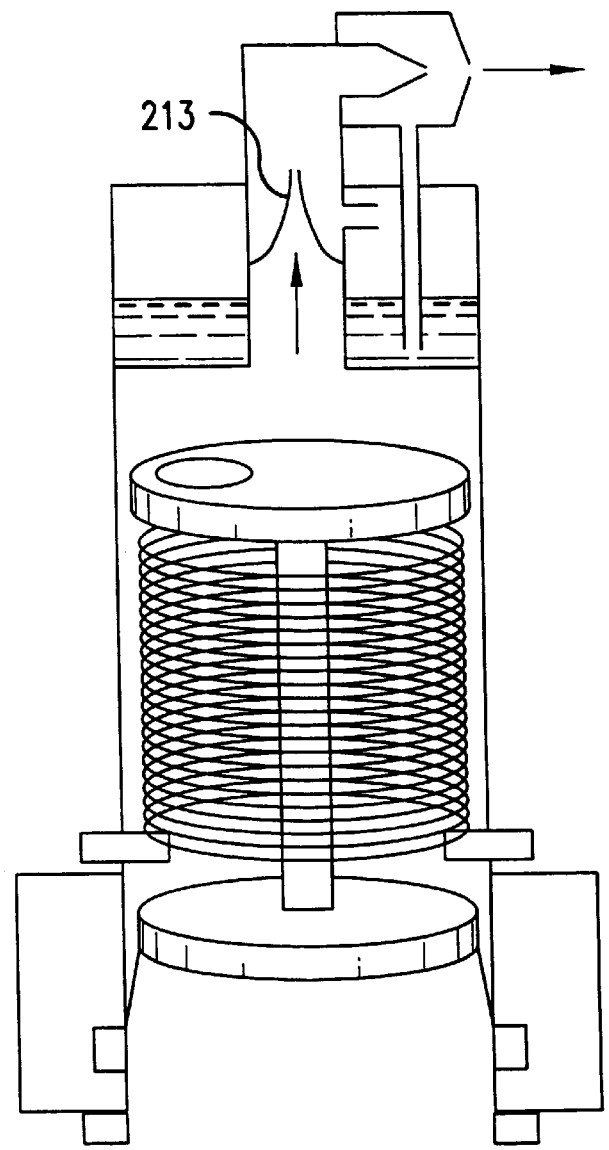
FIG. 31 Eductor Pump with Pressurized Reservior and a One-Way Valve
Figure 31B:
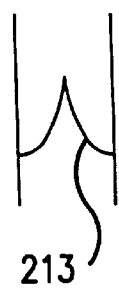
Figure 31C:
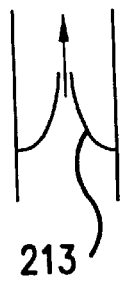
Figure 32:
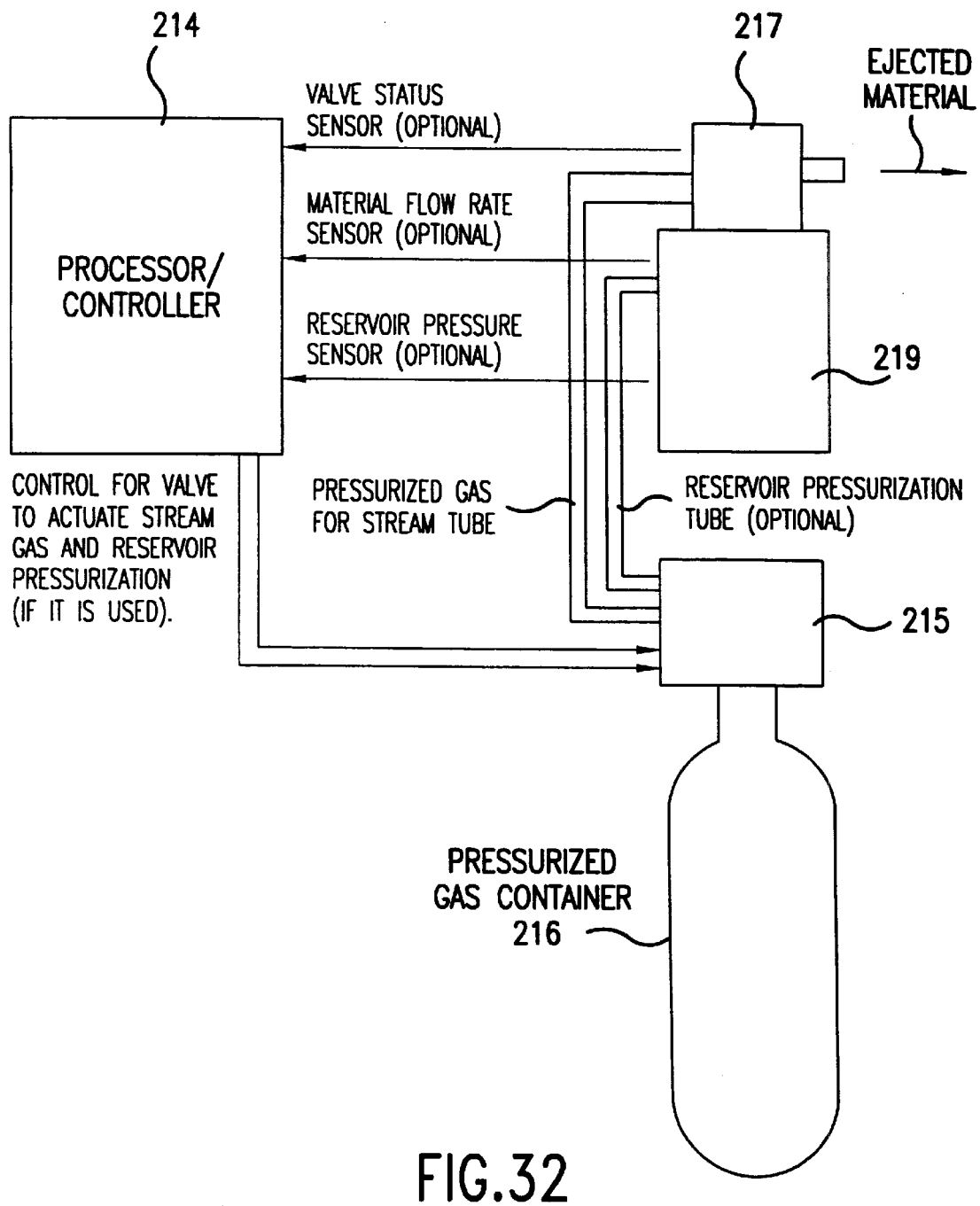
FIG. 32 Microprocessor Controlled Delivery System

One-Way Valve 205A shown in FIG. 24B in Piston 205 is a small plug which seals against Air Passage 205B during the upward stroke of Piston 205. When the Piston 205 is pulled downward to compress a spring such as Spring 153, One-Way Valve 205A unseats and allows air to flow through Passage 205B as shown in FIG. 30B. FIG. 24B further shows that One Way Valve 205A will unseat and allow the free flow of air through Passage 205B when it is inverted. In this configuration, it will allow air to flow freely through passage 205B whether piston Piston 205 is moving upward or downward. This will prevent the ejection of any material when the device is inverted, thus preventing possible excess material or fluid from being ejected. It will also prevent suction of material in an undesirable manner, or the accidental evacuation of Feeder Conduit 196 or similar conduits if the operation of the device is attempted when the device is inverted, thus enhancing safety and usefulness of the apparatus.

Button Release

A very useful modification of the Latching Means Assembly 155 is shown in FIG. 19 wherein the Release Ring 165 has been replaced by Button Ring Assembly 203. Button Ring Assembly 203 is composed of Ring 203A, which contains notch 203B that slides over Horizontal Lug 169. Button Ring 203A holds horizontal pivot 203D on which the Pivot Button 203C is mounted. Horizontal Pivot 203D and Pivot Button 203C are located in Holding Notch 203E. Pivot Button 203C can pivot on 203D inside Holding Notch 203E, and this allow the button to be pulled back so that Latching Pin 156A can be cammed downwardly by Twist Ring 163. Rotation Limiting Notch 203B in conjunction with Horizontal Lug 169 prevents the Button Ring Assembly 203 from rotating, and holds the Pivot Button 203C aligned with Slot 154A.

The operation of cocking and releasing Piston 154 is similar to the previously described process. Piston 154 is pulled downward by Twist Ring 163 as the Twist Ring Camming Surface 166B pushes Latching Pin 156A downward into Holding Notch 203E. When Spring 153 of ID 150 is cocked, Latching Pin 156A is held in Notch 166 of Twist Ring 163, and simultaneously in Holding Notch 203E. The inward displacement of Pivot Button 203C pushes Latching Pin 156A inward past the inner diameter of Notch 166 as previously described. The Piston 154 is released and spring 153 pushes Piston 154 upward as before.

The advantage of the Button Release 203 over the Release Ring 165 is that in some cases, it is easier to aim and deliver the material from the device with one hand that it is using Release Ring 165. The button can be depressed with a single finger while the other fingers of the same hand hold the device. Optionally, a small spring can be added to assist in pushing Pivot Button 203C outward after it is depressed.

Dual Reservoir/Separate Stream Tubes

Figure 26A:
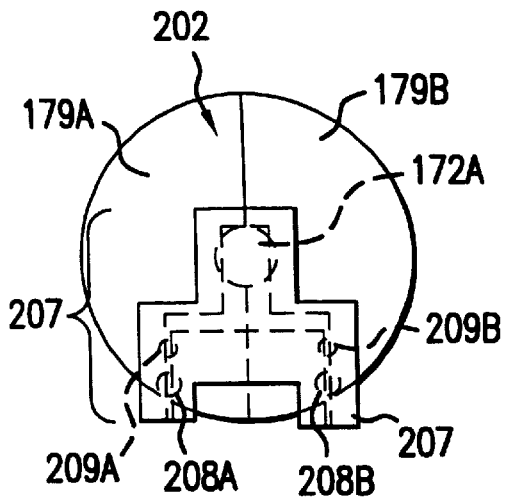
FIG. 26 Two Reservoirs Ejector Head with Reservoirs
Figure 26B:
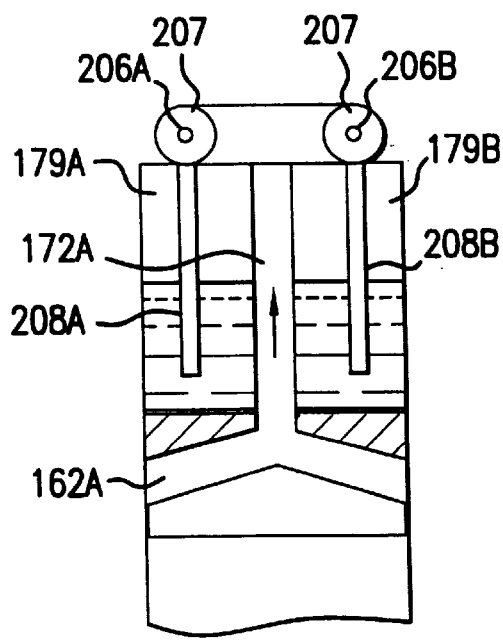
Figure 26C:
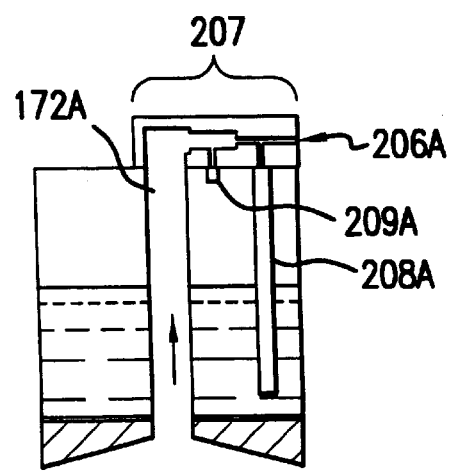

It is possible for the inventive device, ID 150, to be modified to carry more than one type of fluid in separate reservoirs to be delivered with two separate stream tubes. This has the advantage that compounds which are in compatible in storage, but synergistic in their combined effects, can be stored in separate reservoirs and delivered with one concerted action. FIG. 26 shows one such embodiment.

The two Reservoirs 179A and 179B can contain different fluids separated by Wall 202. The Ejector Head 207 has two Stream Tubes, 206A and 206B which are connected to the same Gas Reservoir 162A, by Conduit 172A. Conduit 172A splits into two separate conduits having each nominally half of the cross sectional area of Conduit 172A. The stream tubes may be similar to Stream Tube 161 previously described, or they may be of any of the types shown in FIG. 33 or otherwise designed according to the principles of this invention. Each of the stream tubes, 206A and 206B, connects with feeder tubes 208A and 208B respectively.

If the reservoir pressurization embodiment is employed, the reservoir pressure may optionally be supplied by Taps 209A and 209B connected with Stream Tubes 206A and 206B respectively. The latching and cocking mechanisms may be similar to those used in ID 150, and are not shown in FIG. 26.

The distance between Stream Tubes 206A and 206B may be adjusted to suit the requirements of the particular use contemplated. The centerline axes of the stream tubes can be nominally parallel as shown in FIG. 26, or they can be angled inwardly so that they deliver their respective materials to the same location at some distance from the Dual Ejector Head 207. Obviously, embodiments with three or more reservoirs and stream tubes can be employed from the principles of what is described here.

The Pressure Factor

The role of pressure head is very significant in the operation of the embodiments of the instant invention. The gas (air as described in the preferred embodiment of the invention) pressure provides the driving force (velocity) necessary to accomplish several simultaneous and sequential functions vital to achieve the several important objects of the invention. It provides the dynamic gaseous medium into which the microvolume or submicrovolume liquid portion or microgram or submicrogram powder portion from the liquid reservoir is entrained. It also provides the driving force to mix such liquid or powder (material) to a greater or lesser extent as it is entrained within such driving gas and passes through the conduit from which it is delived to an ultimate target of choice.

It also provides the force to propel such liquid in the form of microdrops or submicrodrops (totaling less than 10 ul, preferably less than 5 ul and as small as one nanoliter) to the target of choice, e.g. an eye to be treated with microvolumes of the liquid as a drug.

It also provides the force to activate the pumping configuration of the apparatus of the invention, whereby the liquid or powder to be propelled to a target is extracted in the correct amounts from the reservoir in which it is contained. That force provides not only a driving factor to propel such powder or microvolume or submicrovolume of liquid, but it is also the force necessary to overcome the natural adhesive attraction of the molecules of such liquid to each other or powder particle to each other in the reservoir and in the conduit as well as the additional attraction of such molecules to the inside surface of the conduit leading from the reservoir from which it is removed. But those forces are not to be overcome to the extent that the quantity of liquid or powder moved from the reservoir exceeds the microgram quantities or microvolumes expressly sought by the object of the invention.

It should be noted that these same adhesive forces exerted by and upon powder particles and liquid molecules in a conduit prevent micro quantities of liquid (less than 10ul) from being dispensed effectively by ordinary gravity driven droppers in the form of single controllable droplets. This is because at such small droplet sizes these natural adhesive or attractive forces are not exceeded by gravitational forces.

In one of the preferred alternative design embodiments of the invention, which utilizes a pressurizing means for the reservoir, the driving gas must also simultaneously provide that reservoir pressure without concomitant diminishment of force so that it cannot accomplish the objects described above. Even a remarkably small increase of reservoir pressure greatly facilitates partially or completely overcoming the adhesive and attractive forces described above. Flexible bag reservoirs within an enclosed rigid structure can also be the recipient of such additional reservoir pressure.

Figure 34:
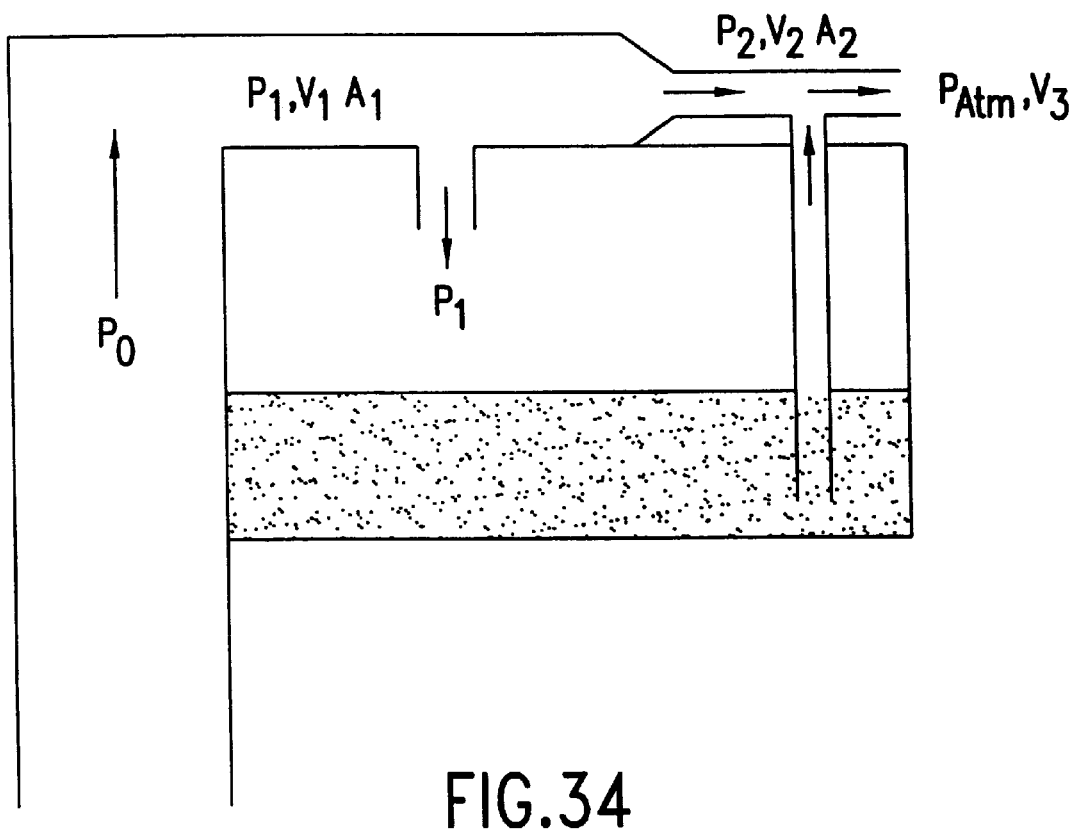
FIG. 34 Schematic View of Two-Tap Stream Tube with pressurized reservoir
Figure 35:
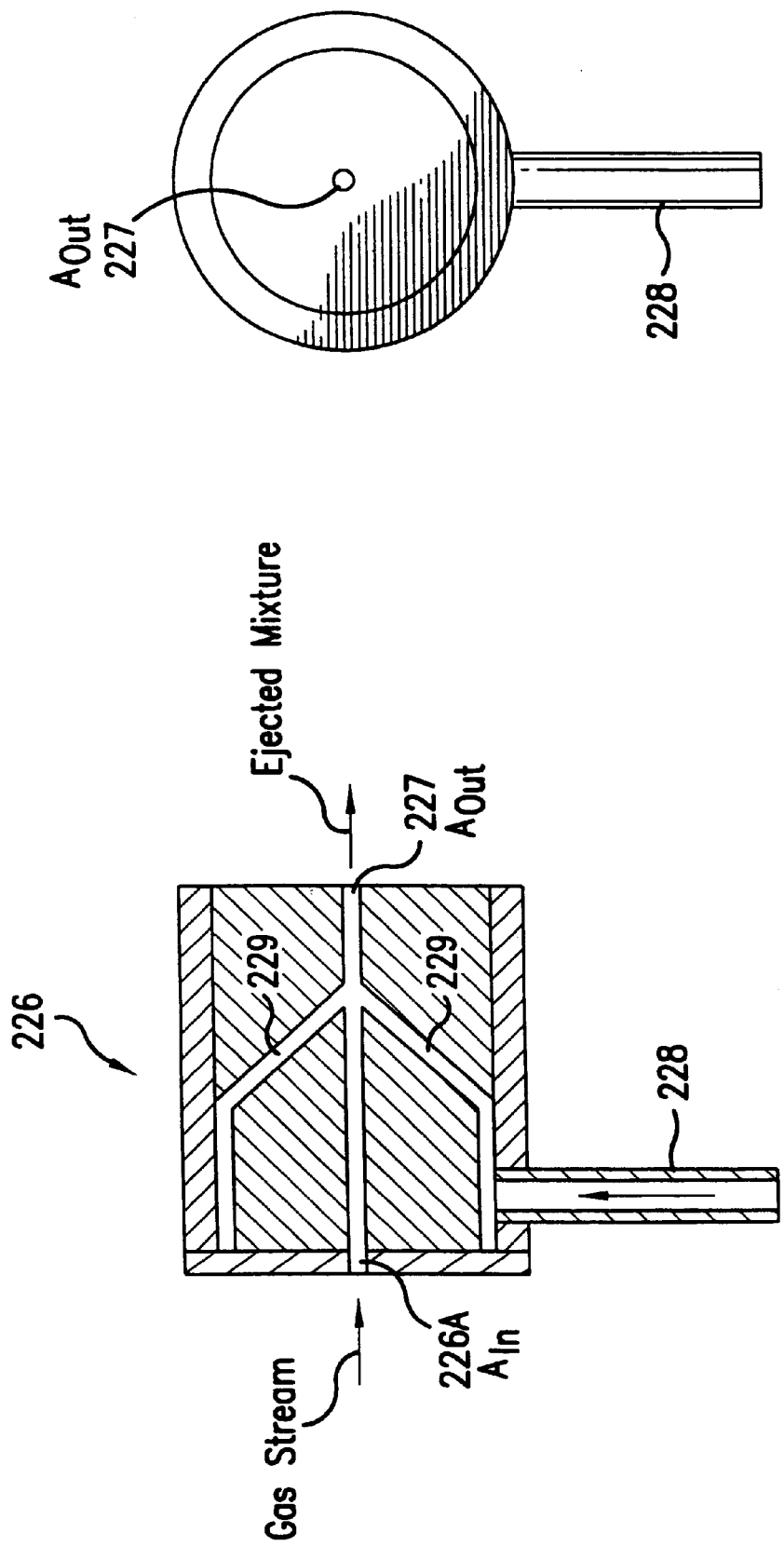
FIG. 35 Stream Tube with Concentric Feed of Suction Fluid or Powder

In those preferred embodiments utilizing reservoir pressure as illustrated schematically in FIG. 34, it is very significant that the reservoir pressure supplied is going to be higher than the static pressure in Second Chamber 187 of Stream Tube 161 where Second Tap 189 connects. Thus, the pressure difference between the pressure in Reservoir 171 and the static pressure in Second Chamber 187 is the amount that is essentially the pressure required to push the reservoir material through Feeder Conduit 196, through Second Tap 189 into Second Chamber 187 which is typically the suction pressure $P_s$. Thus, the difference between the reservoir pressure and the static portion of the pressure in the stream tube where the mixing occurs is essentially the suction pressure. However, it is to be noted that to be effective in this mode, there must always be at least some pressure provided to the reservoir even if just barely above zero.

The various embodiments of the invention using the non-educting and educting stream tubes can select the dynamics of this process so that a selected material from the reservoir is entrained notwithstanding a constant motive head (driving) pressure. It is important to note as a design factor that this pressure difference can be time varying, especially when inertial forces of the suction fluid or material are significant. This effect can be adjusted by varying the length and the cross-sectional areas of the feeder tube.

Reservoir Pressure

Thus, as noted above reservoir pressure (distinct and different from the head pressure) can be surprising low and still be effective. For example, a pressure as low as about zero, but slightly exceeding zero applied to the material reservoir is operable. Generally, a reservoir pressure of 0.1 to 20 pounds per square inch above atmospheric pressure is preferred, and just above zero to 1000 (one thousand), preferably just above zero to 30 pounds per square inch above atmospheric pressure is operable. In keeping with prior terminology, the term "reservoir pressure" or "reservoir pressurization" refer to pressure applied to the material reservoir, such as Reservoir 171 in the most preferred embodiment.

While the driving force behind the propulsion gas must accomplish the many objects described above, it must also not be so forceful that powder or microdroplets of liquid drug delivered to an eye have a objectionable impact against the eye. This is a very important objective which can be achieved by the preferred embodiments of this invention.

Accordingly, it has been discovered that the pressure head of gas in a preferred apparatus of the invention at the peak of the plunger's compression stroke is at least 7.5 pounds per square inch for the eductor facet of this invention with reservoir pressurization and as high as 1000 pounds per square inch, preferably 10 to 60 pounds per square inch and most preferably 0 to 30 pounds per square inch. These pressure numbers are all above atmospheric.

In operation, all of the preferred apparatuses of the invention were operated effectively at about 15 pounds per square inch of pressure atmospheric. For the modified venturi pump embodiment of this invention, the lower end of the useful pressure range is about one (1) pound per square inch above atmospheric pressure with reservoir pressurization. This embodiment requires reservoir pressurization to be operable with the stream tube embodiments shown in FIG. 33A and 33B. It might be noted that perfume atomizers with finger-squeezed compressible bulbs that utilize an eductor configuration (as opposed to the inventively operated eductors of the invention) utilize about 1 to 5 pounds per square inch of air to deliver much higher quantities of liquid (much more than the less than 10 ul preferred by the invention) and in a much wider pattern (and is unacceptable for ophthalmic uses) than that of liquid delivered by the preferred apparatus of the invention.

In some cases, it is desirable to feed two different substances which should remain separated in the storage reservoirs, but should be mixed before delivery. FIGS. 28 and 29 show Stream Tube 161E with 4 chambers of 4 different cross-sectional areas such that $A_1 \geqq A_2 \geqq A_3 \geqq A_4$. FIG. 28 shows the use of Stream Tube 161E dual reservoirs for processing different materials by the process and apparatus of the invention.

The First Chamber 161A and Second Chamber 161B provide pressurization for two different reservoirs. Chamber 161C and Chamber 161D extract fluid or powder from two separated reservoirs. The tube cross-sectional areas $A_1$ and $A_2$ for Chambers 161A and 161B respectively are chosen in relation to $A_3$ and $A_4$ for Chambers 161C and 161D respectively to provide the desired mixing ratios for the materials from the two reservoirs. More than two such reservoirs can be used.

FIG. 28 shows an ejector head and reservoir with Series Stream Tube 161E and dual reservoirs. The components identified in the diagram as follows:

152A is the ejector head body,

1612 is the conduit for introducing pressurized gas into the tube,

1613 is the first reservoir containing fluid or powder,

1614 is the second reservoir containing fluid or powder,

1615 is the pressurizing tap feeding into reservoir 1613 which may or may not have a one-way valve on the orifice entering into the reservoir,

1616 is the pressurizing tap feeding into reservoir 1614 which may or may not have a one-way valve on the orifice entering into the reservoir,

1617 is the feed tube from reservoir 1613,

1618 is the feed tube from reservoir 1614.

The mixing process occurs in the last two chambers (Chamber 161C and 161D) of Stream Tube 161E.

FIG. 25 shows a version of an apparatus with a pressurized reservoir and a non-educting stream-tube. In this embodiment the reservoir pressure is modulated in time and magnitude to provide a clean-out sequence in the induction of an ophthalmic fluid. In FIG. 25, Conduit 154C is used to pressurize the Reservoir 171A. It is connected to the piston by a Flush Opening 154B providing entry to Reservoir 171A through Conduit 154C in the side wall of the Housing 1151, that is a small distance, typically about ¼ of the total travel length of the piston below the top of the cylinder. The pressure is then conducted to the reservoir by Conduit 154C through Orifice 154F. This embodiment is also operated by Piston 1154 which may have dimensions similar to Piston 154 described above, but is a distinctly separate piston.

The method of operation is as follows: Piston 1154 is cocked by the twist ring as in previously described embodiments. When Piston 1154 is released and begins to be pushed upward by the spring, Reservoir 171A is pressurized as in the previously described modified venturi mode of operation, and the material such as fluid or powder in the reservoir is entrained into the gas stream and then ejected out of the Stream Tube 154E. When the piston has traveled about ¾ of its total distance, the orifice for pressurizing Reservoir 171A is now below the seal of the piston, and hence is no longer pressurized. This means that from then on, the reservoir pressure will rapidly decrease, and no further fluid or powder will be pulled up from the Liquid Reservoir 171A. Thus, the remaining fluid or powder in the Stream Tube 154E will be ejected, with no new fluid or powder being pulled into the stream tube from the Feed Tube 154D. In this manner the Stream Tube 154E is cleaned out so that after use no fluid or powder is left in Tube 154E to dry out and clog Stream Tube 154E.

It may be desirable to make the upward piston stroke, or travel distance slightly longer than in the most preferred embodiment, ID 150, if a similar amount of material delivered is desired. This is because the portion of the upward stroke of Piston 1154 where the piston is past Flush Opening 154B, does not result in suction and delivery of added material from Liquid Reservoir 171A.

It should be noted that for the purposes of this invention another source of pressurized gas can be used with a separate valving arrangement, as will be apparent to those skilled in the art. This is illustrated in FIG. 32.

Although the above discussion is with respect to liquids, it is to be understood that powder can be used in the apparatuses of the invention either by itself or in conjunction with a liquid delivery. Moreover, the quantities of materials delivered can be substantially lower than 1 micro liter in volume or one microgram in mass. Indeed quantities as low as one nanoliter in volume or one nanogram in mass can also be delivered with the apparatus of this invention.

In FIG. 33, three different examples of stream tubes useable in this invention are shown. The horizontal components of the stream tubes convey the motive gas and any gas-material mixture. The vertical tube intersecting the various stream tubes conveys a portion of material from the reservoir containing such material. The stream tube shown in FIG. 33A is fundamental and is analogous in function and placement to second chamber 187 and tap 189 in the embodiment described above in FIG. 23C and is shown here for completeness of this discussion. The entry and exit cross-sectional areas $A_{in}$ and $A_{out}$ are the same, and this type of stream tube requires reservoir pressure (source not shown) as provided in the most preferred embodiment described above.

Figures 25A, 25C:
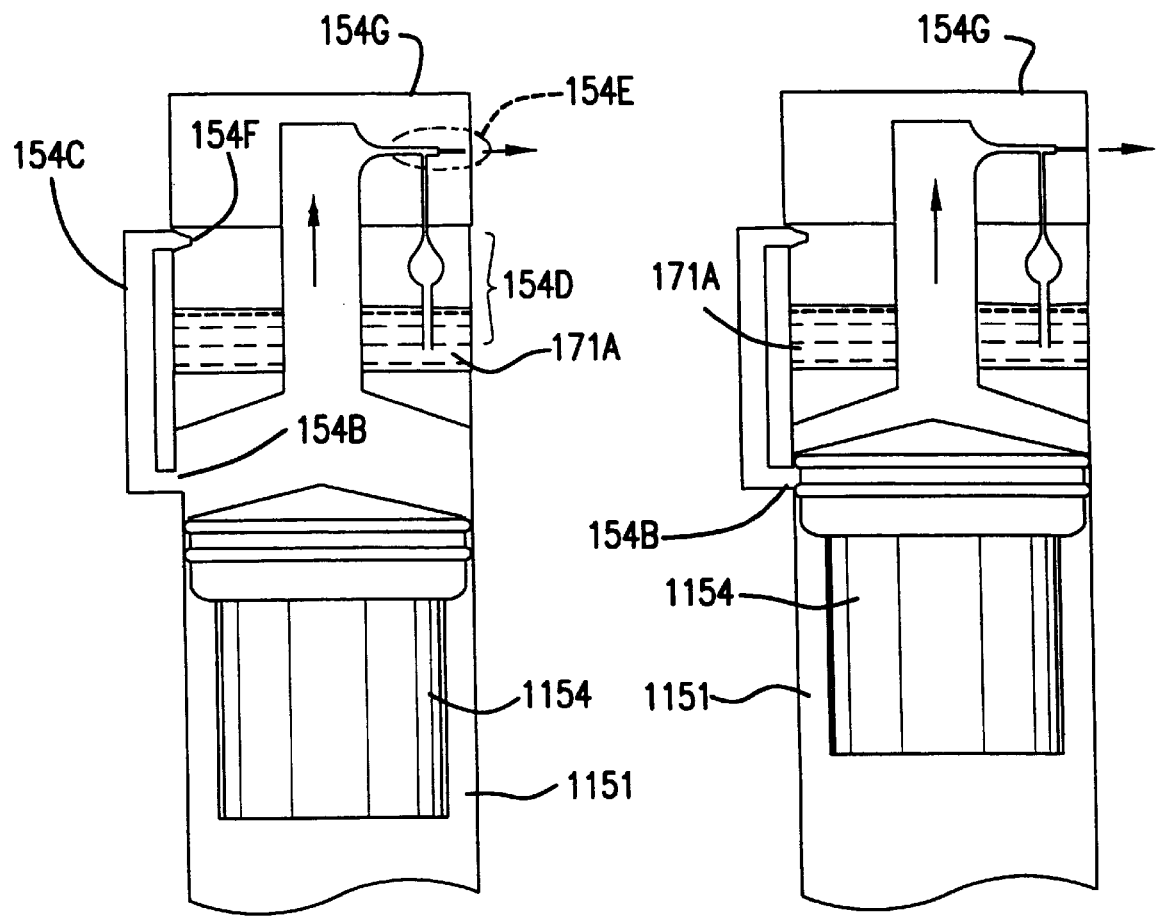
FIG. 25 Pressure Cutoff to Reservoir
Figure 25B:
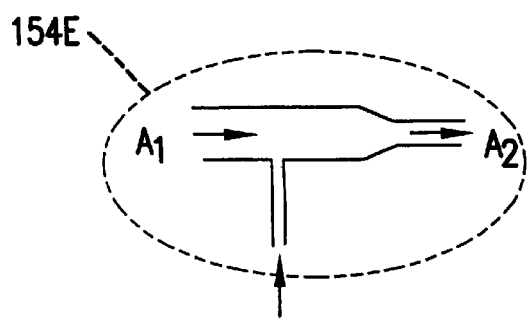

In the second stream tube shown in FIG. 33B, $A_{in}$ and $A_{out}$ differ in their respective diameter where $A_{in} > A_{out}$ and the mixing ratio for this is as described previously in equation 19. This type of stream tube allows the control of the mixing ratio as well as the provision of a back pressure when the reservoir pressure is removed as in the examples shown in FIGS. 25 and 30. This stream tube only requires one tap into the reservoir which is an improvement in simplicity over the two tap stream tube. Because of this, the mixing ratio can be controlled by the ratio of the two cross sectional areas and any reservoir pressure will be applied directly from the piston and controlled by the piston position. Thus techniques to remove remaining reservior material from the stream tube junction after delivery such as shown in FIGS. 25 and 30 can be applied with this type of stream tube. The embodiments shown in FIG. 25 and 30 could be used with the types of stream tubes shown in FIGS. 33A and 33C.

It is preferable to use the non-educting stream tube shown in FIG. 33B when it is desired to have a positive back pressure to remove material from the stream tube after delivery. The feeder tap that allows the reservoir material to enter the stream tube preferably connects to the stream tube with at least 2 times the characteristic cross section dimension (i.e. diameter for round tubes) case $A_{in}=A_{out}$ shown in FIG. 33A. For the case shown in FIG. 33B, where $A_{out}<A_{in}$ the feeder tube is preferably placed close to the neckdown of cross-sectional area from $A_{in}$ to $A_{out}$. The length of the section of cross sectional area $A_{out}$ should preferably be at least 2 times the characteristic length of the cross section dimension. For the case shown in FIG. 33C, the tap should preferably be placed at or as close as possible to the transition between $A_{in}$ and $A_{out}$. Thus, the teaching of the invention contemplates a variety of adjustments from selection of tube sizes and combinations thereof coupled with appropriate location of feeder taps.

FIG. 35 shows Stream Tube 226 with the suction material feed to the stream tube by an Annular Slot 229 around the perimeter of the Stream Tube 226. This provides the advantage of allowing better mixing between the motive gas and the suction fluid or powder. The motive gas is fed into Conduit, 226A, having an initial cross-sectional area $A_{in}$. The suction fluid is pulled up into an Annular Slot 229 by the pressure difference between the gas in Conduit 226A in Stream Tube 226 and the reservoir. The suction fluid or powder enters the stream tube where the annular slot connects to the stream tube and is finally ejected out of Mixing Section 227. The cross-sectional area of 227 is $A_{out}$, and may be smaller than or equal to $A_{in}$. Thus it is possible to make this operate in the same manner as the stream tube shown in FIG. 33. It is possible to make Mixing Section 227 after the annular slot shorter than would be for a simple tap into one side of the tube and still achieve the same degree of mixing.

FIG. 36 shows an embodiment similar to that used to create the test data shown in Tables 1 and 2. A 10 cc Syringe, 223, was used to provide measured motive air connected through Fitting Conduit 225 for Ejector Head 221, in which a number of pump and pressure configurations were tested. The Reservoir 222 contained the suction fluid, which was pulled up into Ejector Head 221 operating in an eductor configuration and ejected to a preselected target through Exit Orifice 224.

The mode of operation follows: The volume of air is selected by pulling the Syringe Piston 220 back a predetermined distance. The volume of air determines the volume of suction fluid delivered by the mixing ratio described above. The Exit Orifice 224 is held 1–3 inches from the area selected for delivery, and the Syringe 223 is quickly pushed with the thumb. The air is pushed through the Ejector Head 221 and the correct amount of fluid is delivered to the selected target area.

As previously stated, the embodiment in FIG. 36 can be used with any of the stream tubes that are described above herein. It was tested both with and without reservior pressurization. It was found that this embodiment was particularly useful when medicaments were administered in varying controlled quantities.

Metering Wheel Example

An embodiment of the invention which employs a metering wheel is shown in FIG. 9. The metering wheel 63 serves to separate and meter the flow of the liquid to be delivered into an air passage for induction ejection to the eye. This embodiment performs a method which is basically related to the methods of the previous embodiments. It is envisioned that this embodiment will be preferable for delivery of fluids with higher viscosities.

The metering wheel embodiment includes a housing 60, piston 62, reservoir 64, bellows 66, air passageway 68, nozzle 70, shaft 72, centralizer 74, spring 76, extension tube 78 and level controller 80 and piston 82. This embodiment also includes a cocking mechanism and release mechanism similar to that shown in FIG. 1. The cocking mechanism includes a twist sleeve or ring 84 and one or more catches spring loaded by spring struts 86. The sleeve 84 has an inclined groove or track in its interior surface for each catch and along with the catches moves when being cocked.

The release mechanism includes a manually operated sliding button or post 86 which releases the catches, thereby enabling the spring 76 to drive the piston 62 upward. The piston, in turn, displaces gas against the bellows 66 and flows through passageway 60 and nozzle 70. The bellows 66 acts against the piston 82 which cooperates with the level controller 80 to maintain a desired level of fluid in the reservoir. The fluid level is such as to immerse teeth or paddles 61 when at the bottom of the wheel 63.

Gas exiting the nozzle 70 turns the wheel 63 and induces a fluid material on the exterior surface of the wheel to mix with the gas stream. The mixture then ejects from the gas passageway to impinge on an eye or other desired body part.

The level controller 80 in FIG. 9 includes a floating ring 84, a bar ratchet 86, and a locking pawl or tooth 88. The lower end of the ratchet 86 contacts the piston 82 and is free to move within the ring 84 and the extension tube 78. The pawl or tooth 88 is pivotally mounted on the ring 86 and has a cam surface on one end and a tooth on the other. It is dimensioned such that when the cam surface contacts the top end of the reservoir 64, the tooth end engages and locks movement of the ratchet 86. The locking action is selected to occur in a preferred embodiment when the fluid level immerses the teeth 61 of the wheel 63. The locking action also fixes the position of the piston 82 until the level of fluid diminishes. It will be appreciated that the pawl 88 may alternately be pivotally attached to the top of the reservoir 64 and still be actuated by a float such as the ring 84 to lock the ratchet 86. As is apparent, the diameter of float 84 should be greater than the diameter of the extension tube 78.

Extension tube 78 allows the ratchet 86 to extend up past the top of the reservoir 64 to prevent spillage of the material.

The ratchet extends further up into the tube as the material is used. The inner diameter is large enough to allow the ratchet 86 to freely slide in and out without impediment.

The ratchet extension 86 effectively connects the sliding piston 82 with the float 84 and engages the locking tooth 88 to prevent the piston 82 from moving any further upward when the fluid in the reservoir reaches an intended or predetermined level. The ratchet extension is approximately ½" to ¾" long, and is cylindrical in shape with one side consisting of serrated teeth. This side is also flattened slightly to help prevent the float from rotating with respect to the extension.

The spring strut 86 is attached to the lower part of the piston 62—i.e., the disk 74—and also has a catch or engaging member for the twist ring 84. This catch is pressed backward when the release button 86 is pushed, and enables the air piston 62 to move upward.

Two Step Entrainment Process

Figure 10A:
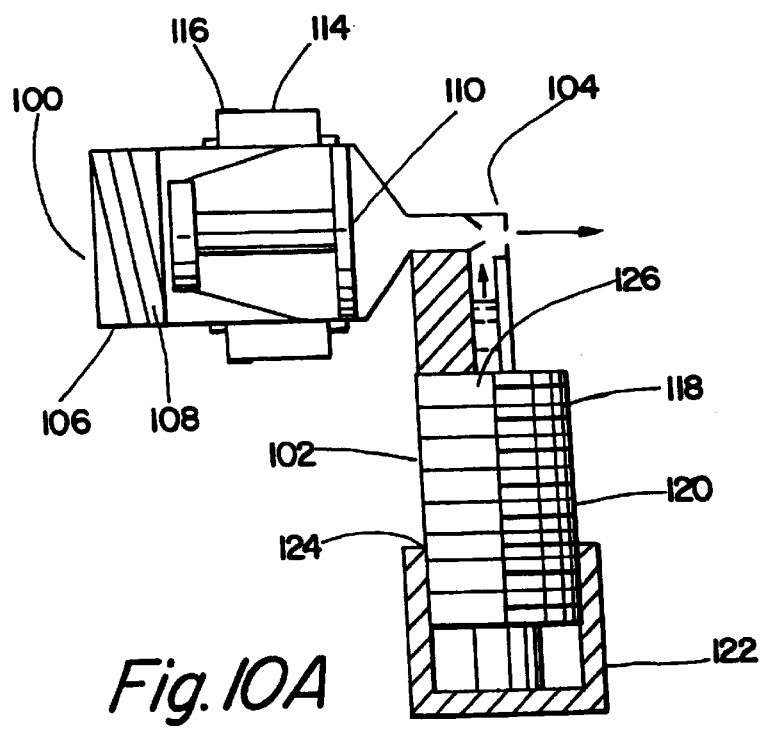
FIG. 10 is a schematic, cutaway front view of another embodiment of the invention employing an eductor pump mechanism for inducing and metering a liquid into an air stream.
Figure 10B:
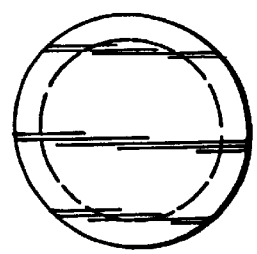
Figure 9A:
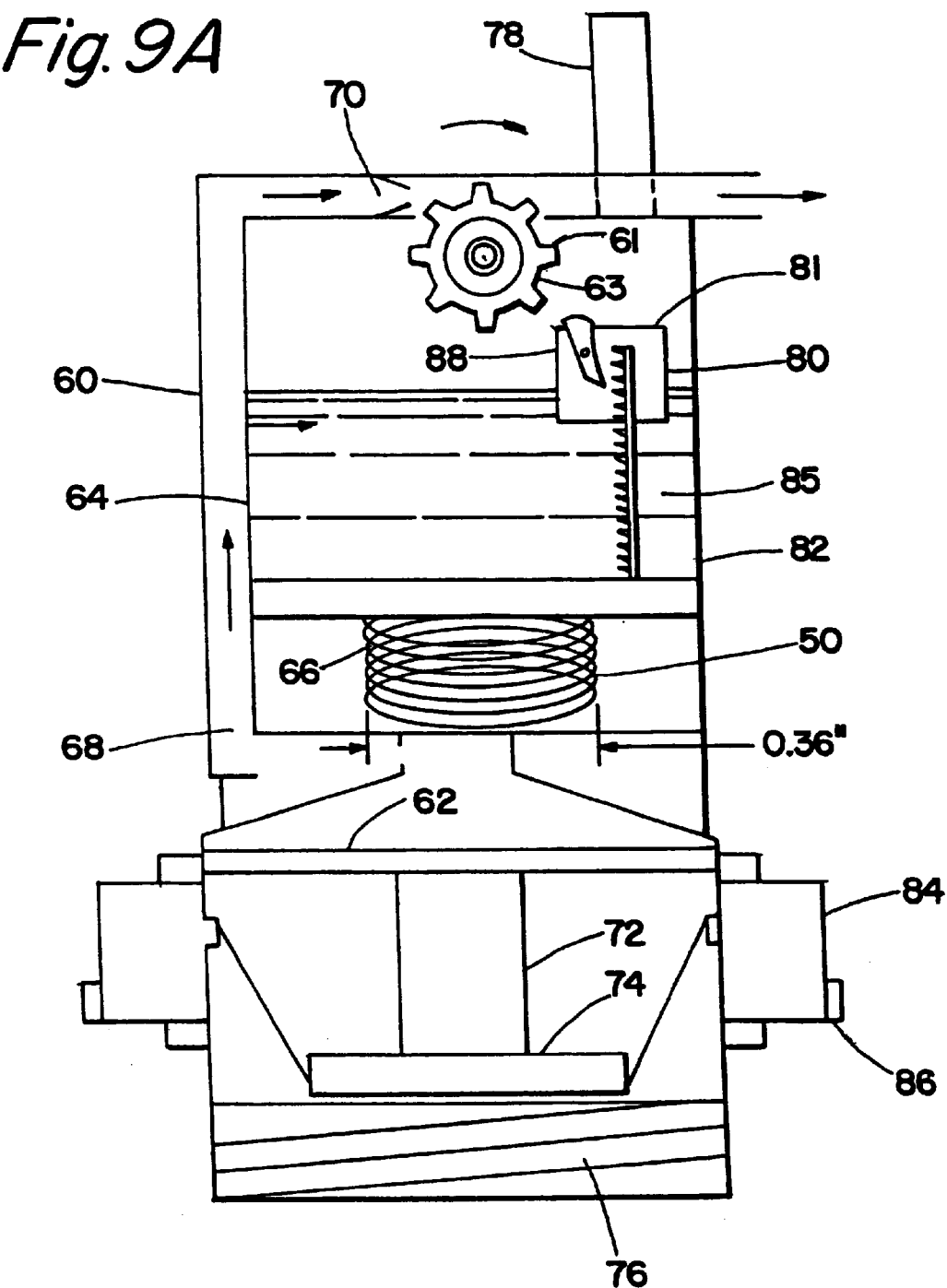
FIG. 9A is a schematic, cutaway, longitudinal view of an embodiment of the invention employing a metering wheel or paddle wheel to feed a liquid for induction (entrainment) into a gas stream.
Figure 9B:
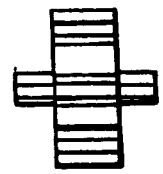
FIG. 9B is a front view of the metering wheel in FIG. 9A.
Figure 11A:
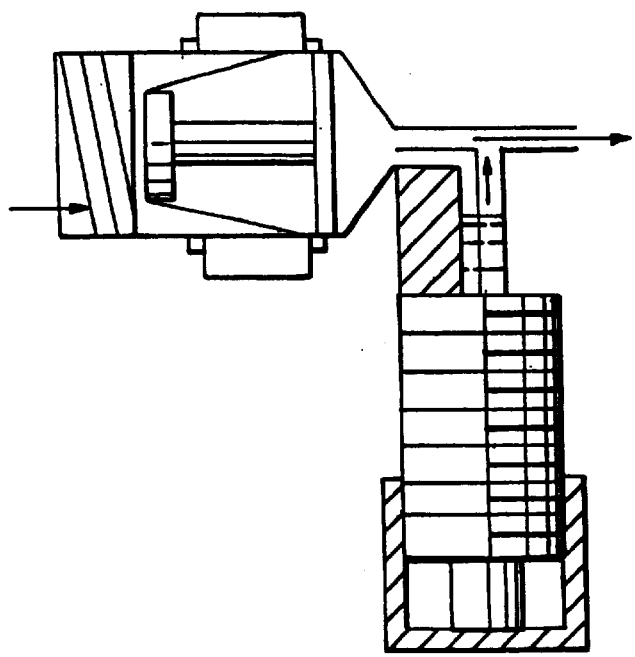
FIG. 11 is a schematic view of the device of FIG. 10 showing a venturi modified as a pump in place of the eductor (jet) pump of FIG. 10.
Figure 11B:
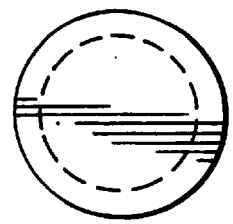
Figure 12A:
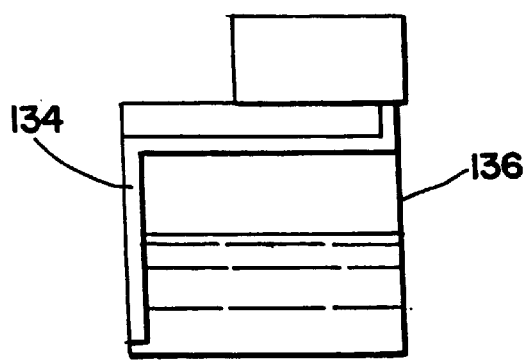
FIG. 12 is a schematic view of a pump, reservoir and feeding tube for use in embodiments of the invention enabling use of the device in a horizontal or vertical position.
Figure 12B:
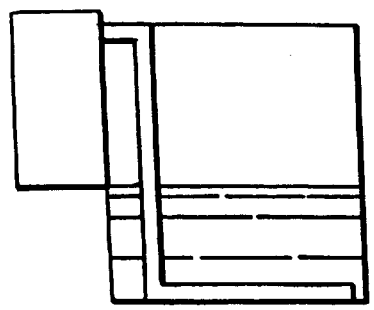

FIG. 10 is a schematic layout of an embodiment of the invention which involves a two-step gas entrainment procedure using a pump to eject fluid. The apparatus in this embodiment includes three principal components—a source of metered compressed gas or air 100, a source of a metered fluid material 102, and a pump 104, in this case, an eductor pump. The source of metered gas or air 100 is very similar in principle and components to the gas or air source of FIG. 9A, and its major components are only mentioned here. They include a housing 106, a spring 108, a piston 110, an gas or air passageway 112, a twist sleeve 114 and a cocking and releasing assembly 116.

The source of metered fluid 102 includes a fluid reservoir 118 with an external thread 120, an internally threaded cap 122 and piston 124 assembly, and a metering tube 126. Threading of the cap 122 onto the housing forces the piston 124 upward in the fluid material reservoir 118 and the tube 126. The tube 126 is preferably calibrated and clear so that a known amount of a fluid material is ready for ejection. Actuating the spring 108 forces a known or metered amount of air through the passage 112 and the eductor pump 104, thereby inducing a fixed quantity of the fluid material to be ejected.

The volume to be delivered is determined precisely by the dimensions of the chamber. In FIG. 10 this is accomplished by turning the thumbwheel 122 to force a predetermined amount of material into the clear chamber 126 of desired volume where it can be observed. When it is observed to be full, the piston 110 is cocked by the twist ring 114 similar to the previous embodiments. The device is pointed towards the eye, and it is activated when the spring 108 is released by the release assembly on the twist ring. The air from the piston 110 is predetermined to be sufficient to remove the fluid from the clear tube 126 and eject it to the eye. Because the metering is accomplished by precisely displacing the piston 124 in the material reservoir, very accurate determination of delivery of small volumes becomes possible.

The clear tube 126 dimensions are typically such that when the tube is full a selected volume (e.g. 10 ul of material will be delivered). When the chamber is half full, only 5 ul of material will be delivered. The user can see the material to be delivered in the tube and judge when it is full without having to possibly waste any material. The advantage of this method over the single step method is that the device is not required to be held in an upright position to operate. A further advantage of this method over the single step method is that the metering can be very precise with additional safety provided from accidental overdose.

EXAMPLE 3
Illustration of The Use of The Novel Delivery System Described in Example 1

An initial evaluation was undertaken using five normal volunteers with symmetrical intraocular pressures having no ocular or clinically significant systemic disease and taking no medications. On the study day each volunteer at Hour 0 (Hr0) had his/her intraocular pressure (IOP) measured by Goldman applanation tonometry. Blood pressure (BP) and pulse rate(P) were measured at the same time. Results obtained from this preliminary study on five human volunteers have overlapping times (see Table 3 below) since subjects did the study on different days. Enrolled subjects were required to have absolutely symmetrical IOPs at hour 0. After at least 30 min and no more than 1 h, each volunteer received 5 ul of 0.25% timolol hemihydrate (Betimol) to the right eye (OD) and no treatment to the left eye (OS). Timolol is a beta-blocker with ocular effects of decreasing the intraocular pressure and potential systemic side effects of bronchoconstriction, decreasing blood pressure and decreasing heart rate. The device of the invention used to deliver the dose was a prototype that was calibrated so that the volume of material given was known from the volume of air displaced. The device was a one-step gas induction delivery device that used an eductor pump to deliver the medicine. The person giving the dose was not involved in the evaluation of the volunteer. Two hours later intraocular pressure, blood pressure and pulse rate was again measured. The blood pressure included both systolic and diastolic readings.

TABLE 3

Effects of using 0.25% Betimol dosing OD Only in Normal Human Volunteers

| | Hour Zero Data | | | | Second Hour Data | | |
|---|---|---|---|---|---|---|---|
| Patient | Time | IOP | BP/P | Dose Time | Time | IOP | BP/P |
| CD | 9:35 AM | 12/12 | 112/84-74 | 10:32 AM | 12:25 PM | 9/11 | 112/78-86 |
| KN | 9:38 AM | 14/14 | 98/65-69 | 10:30 AM | 12:27 PM | 9/12 | 100/61-68 |
| CA | 9:45 AM | 16/16 | 95/75-66 | 10:32 AM | 12:29 PM | 16/16 | 108/72-88 |
| KZ | 9:47 AM | 18/18 | 116/72-66 | 10:31 AM | 12:31 PM | 13/16 | 117/70-72 |
| RR | 8:35 AM | 20/20 | 154/97-74 | 8:35 AM | 10:25 AM | 14/18 | 148/88-53 |

No volunteer offered any subjective complaints at the time of dose delivery to the right eye. No redness or other objective ocular signs were observed after dosing. No reflex tearing, blinking, or wiping was observed. Each subject except for one (CA) had a decrease in intraocular pressure in the right eye.

The percent reduction at Hour 2 using the left eye's intraocular pressure at Hour 2 as the control ranged from 13% to 25%. Two subjects had a decrease in pulse rate at Hour 2. One of these subjects had a pulse rate hange from 69 at baseline to 68 at Hour 2. The other three subjects demonstrated a substantial increased in pulse rate ranging from 6 to 22 beats per min.

Only one subject had a decrease in blood pressure. All other subjects had essentially no change in blood pressure. This preliminary study demonstrates the safety and feasibility in normal human volunteers of one step gas induction delivery. The nonselective Beta-antagonist Timolol was chosen as the agent of delivery because of its common use in clinical practice, its known potential systemic and local side effects, and its known ability to lower intraocular pressure in normal human subjects.

No elicited or volunteered subjective complaints accompanied the drug delivery to the right eye at Hour Two. No consistent effect was observed on pulse rate or systemic blood pressure. Only one subject did not respond with a reduction of intraocular pressure in the treated right eye. The reduction in intraocular pressure in these normal volunteers is consistent with that in the ophthalmic literature using standard bottle delivery (1).

The standard clinical delivery of Timolol is 30 ul of a 0.5% solution. This yields a dose of 150 ug to the eye. In this study a dose of only 12.5 ug was delivered to the eye. This is a twelve fold reduction in dose with no apparent loss of pressure lowering effect. Discussion for this apparatus has focused on the use of the delivery of small controlled volumes of ophthalmic liquids. Other uses for this invention include, but are not limited to, materials delivery involving the following body organs and fields of medicine: Ear (Otic), Nose (Nasal) and Throat Dental (Ora 1), Dermatologic, Wound Healing, Cardiovascular, Oncology, Chemotherapy, Endocrine, Central Nervous System, neurosurgical, neurologic, Urologic, Genital, Gynecologic, Obstetrical, Colorectal, General Surgical, Gastrointestinal, Pulmonary Orthopedic, Pediatric, Rheumatologic, and Pediatric.

Where dose reduction may be critical, such as for sublingual or nasal applications, all of the methods and apparatus disclosed and claimed herein may be made and executed without undue experimentation in light of the present disclosure.

Non-Exhaustive/Non-Exclusive List of Opthalmic Drugs/Preparations

The following list represents a variety of classes and compounds for which the instant invention is especially suited for in clinical applications:

I. Parasympathomimetic/cholinergic drugs
  1. Pilocarpine
  2. Acetylcholine
  3. Carbachol
II. Adrenergic Agonists
  1. Epinephrine
  2. Dipivefrin
  3. Clonidine
  4. Apraclonidine
  5. Brimonidine
III. Beta Adrenergic Antagonists/Blockers
  1. Timolol Maleate
  2. Timolol Hemihydrate
  3. Levobunolol
  4. Carteolol
  5. Metipranolol
  6. Betaxolol
IV. Topical Carbonic Anhydrase Inhibitors
  1. Dorzolamide
  2. Benzolamide
V. Prostaglandin Analogs and Related Derivatives
  1. Latanaprost
  2. Ocular hopotensive lipids
  3. Unoprostone
  4. Leukotrienes
  5. Antagonists of prostaglandins and leukotrienes
VI. Calcium Channel Blockers
  1. Verapamil
VII. Antiinflammatory Compounds
  1. Diclofenac
  2. Ketorolac
  3. Dexamethasone
  4. Fluoromethalone
  5. Prednisolone
  6. Loteprednol -continued VIII. Antimicrobials
  1. Ciprofloxacin
  2. Oxfloxacin
  3. Triflurthymidine
IX. Immunomodulators/Wound Healing Modulators
  1. Motomcin C
  2. 5-Flurouracil
  3. Cyclosporine
X. Growth Factors
  1. EGF
  2. BDNF
  3. VEGF
  4. FGF
XI. Hormones
  1. Growth hormone
  2. Glucagon
  3. Insulin
XII. Cytokines
  1. TNF
  2. Interleukins
XIII. Anestheics
  1. Proparacaine
  2. Tetracaine
XIV. Mydriatics/Cycloplegics
  1. Phenylephrine
  2. Tropicamide
  3. Atropine
  4. Cyclopentalate
XV. Diagnostic Agents
  1. Lissamine Agents
  2. Rose Bengal
  3. Flouroscein
XVI. Artificial Tears/Viscosifying Agents
  1. Carboxymethylcellulose
  2. Polyyinyl Alchohol
  3. Hydroxymethylcellulose
  4. Polycarbophil While the methods and apparatus of this invention have been described in terms of preferred embodiments, it will be apparent to those of skill in the art that variations may be applied to the methods and apparatus and in the steps or in the sequence of steps of the method described herein without departing from the concept, spirit and scope of the invention.

All similar substitutes and modifications apparent to those skilled in the art are deemed to be within the spirit, scope and concept of the invention as defined by the appended claims. The inventive liquid reservoir pressure techniques of the invention used for the purpose of micro- and submicro-quantity delivery, and embodiments of the invention can be applied with considerable usefulness to the conventional macro embodiments.

What is claimed is:

1. A process for consistently delivering units of essentially repeatably uniform and equal quantities of material in a preselected amount of from 1 nanogram to 1000 micrograms of powder or from 1 nanoliter to 100 microliters of liquid or a combination of both powder and liquid to a location of choice, which comprises in combination the steps of:

a) selecting the quantity of material to be delivered in units of essentially equal quantities of material in any preselected amount of from 1 nanogram to 1000 micrograms of powder or from 1 nanoliter to 100 microliters of liquid or a combination of both powder and liquid;
  b) providing a conduit having a back end, a middle portion and a front end;
  c) providing a reservoir for said material containing an amount of at least the said quantity of material selected and being operatively connected to said middle portion;

d) providing at said front end a source of a repeatable, measured amount of gas under from 1 to 1000 pounds per square inch pressure above atmospheric, wherein said gas being selected in a quantity having a relationship with said material quantity expressed as from about 0.003 to 300 parts of gas per every part of liquid by weight and 0.1 to 20,000 parts by weight for powder;

e) providing an exit orifice for said back end;

f) releasing said pressurized gas in a measured repeatable amount so as to be conveyed through said conduit and to exit through said orifice;

g) reducing the pressure of said gas as it passes through said middle portion sufficiently to cause said unit quantity of material to exit said reservoir and be entrained by and mix with said gas in both the middle portion and back end of said conduit;

h) expelling said entrained mixture of gas and material through said orifices; and i) conveying said entrained mixture to said location.

2. The process of claim 1, wherein said combination includes the step of pressurizing said liquid reservoir with the pressurized gas from said source prior to or instantaneous with removing liquid material from said reservoir and the pressure head in said source is from 1 to 1000 pounds per inch above atmospheric.

3. The process of claim 2, wherein said material reservoir is at a pressure of 0.1 to 20 pounds per square inch.

4. The process of claim 3, wherein said material reservoir is at a pressure of from just above zero to 500 pounds per square inch.

5. The process of claim 4, wherein said amount of gas is newly pressured before each of said releases.

6. The process of claim 1, wherein two or more reservoirs are employed.

7. The process of claim 1, wherein said gas is selected from the group consisting of air, carbon dioxide, helium, inert gases and inorganic gases.

8. The process of claim 1, wherein said liquid is drug.

9. The process of claim 1, wherein said powder is a drug.

10. The process of claim 8, wherein said drug is an ophthalmologic drug.

11. The process of claim 9, wherein said drug is an ophthalmologic drug.

12. The process of claim 1, wherein the pressure of said gas is from 7.5 to 1000 pounds per square inch above ambient.

13. A process for consistently delivering units of essentially repeatably uniform and equal quantities of material in a preselected submicro to micro amount of from 1 nanogram to 300 micrograms of powder or from 1 nanoliter to less than 30 microliters of liquid in droplet form or a combination of both powder and liquid to a location of choice, which comprises in combination the steps of:

a) selecting the quantity of material to be delivered in units of essentially equal quantities of material in any preselected amount of from 1 nanogram to 300 micrograms of powder or from 1 nanoliter to less than 30 microliters of liquid droplet form or a combination of both powder and liquid;

b) providing a conduit having a back end, a middle portion and a front end;

c) providing a reservoir for said material containing an amount of at least the said quantity of material selected and being operatively connected to said middle portion;

d) providing at said front end a source of a repeatable, measured amount of gas under from 1 to 1000 pounds per square inch pressure above atmospheric in a quantity having a relationship with said material quantity expressed as from about 0.01 to 100 parts by weight of gas per every part of liquid or 0.2 to 10,000 parts by weight for powder;

e) pressurized said reservoir with at least a pressure exceeding zero pounds per square inch above atmospheric and up to 500 pounds per square inch prior to or essentially simultaneously with removing material from said reservoir;

f) providing an exit orifice for said back end;

g) releasing said pressurized gas in a predetermined quantity so as to be conveyed through said conduit and to exit through said orifice;

h) reducing the pressure of said gas as it passes through said middle portion sufficiently to cause said unit quantity of material to exit said reservoir and be entrained by and mix with said gas in both the middle portion and back end of said conduit;

i) expelling said entrained mixture of gas and material through said orifices; and j) conveying said entrained mixture to said location.

14. The process of claim 13, wherein said liquid is an ophthalmologic drug.

15. The process of claim 13, wherein said powder is an ophthalmologic drug.

16. The process of claim 13, wherein the mixture exiting said orifice is at higher pressure than ambient.

17. An apparatus for delivering selected quantities of certain materials to a targeted location, which comprises in combination the elements of:

a) a container means having operatively associated therewith;
 i) rigid-walled, gas reservoir means;
 ii) gas conduit means within said container for repeatedly conveying approximately the same predetermined quantity of a chosen unit of said gas under a selected predetermined pressure;
 iii) means for introducing gas under pressure from said gas reservoir means to said gas conduit means within said container means; and
 iv) a liquid or powder reservoir means;

b) control means for maintaining aid gas pressure initially at between 1 to 1000 pounds per square inch above ambient;

c) means for removing,
 i) from one nanoliter to 100 microliters of liquid material from said reservoir means, or
 ii) from one nanogram to 1000 micrograms of powder material from said reservoir means;

d) means for providing from 0.01 to 100 parts of gas for every part of liquid material entrained by such gas such parts being by weight and 0.2 to 10,000 parts of gas for every part of powder such parts being by weight;

e) means for mixing said quantity of removed material with said predetermined quantity of gas to result in a mixture of said gas and said material;

g) means for forceably expelling said mixture from said container and means for propelling a major portion of said removed material at least one inch.

18. The apparatus according to claim 17, wherein said combination includes means for providing gas from said gas reservoir means to said liquid reservoir prior to or simultaneously with any said removal and a pressure ranging from above zero to 1000 pounds per square inch of pressure above ambient in said material reservoir means.

19. The apparatus according to claim 17, wherein said material reservoir is located inside said container.

20. The apparatus according to claim 17, wherein said gas reservoir is located inside said container.

21. The apparatus according of claim 17, wherein said material is a liquid or powder.

22. The apparatus according to claim 17, wherein said reservoir is initially operatively connected by means of pressure connecting means to the initial pressure head from said gas reservoir and conduit blocking means are provided to close said operative connection prior to the expelling of said mixture from said container.

23. The apparatus according to claim 22, wherein air within said air reservoir is compressed by a piston and said conduit blocking means is said piston.

24. The apparatus according to claim 17, wherein gas is contained in a flexible container within said reservoir.

25. The apparatus according to claim 17, wherein said liquid or powder reservoir means are accompanied with at least one other liquid or powder reservoir means.

26. The apparatus according to claim 17, wherein said means for removing liquid or powder material is a metering wheel.

27. The apparatus according to claim 17, wherein said gas reservoir is a syringe.

28. An apparatus for delivering selected quantities of liquid to a targeted location, which comprises in combination the elements of:
   a) a rigid essentially closed container containing;
      i) gas reservoir means for holding a predetermined quantity of gas under a predetermined pressure of from 1 to 1000 pounds per square inch above ambient located within said container;
      ii) pressure release means for releasing said gas pressure located within said container;
      iii) fluid reservoir means for holding a fluid to be delivered;
   b) first gas conduit means having a cross-sectional diameter of from 50 to 125 mils operatively connected conveying gas from said gas reservoir;
   c) second conduit means having a cross-sectional diameter of from 8 to 50 mils for connecting said liquid reservoir with said first gas conduit means;
   d) pump means for conveying liquid from said reservoir means to said first conduit means;
   e) mixing means for mixing 1 to 30 microliters of liquid form said reservoir with said gas in said first conduit means to form a mixture of said entrained liquid and said gas;
   f) exit conduit means having an orifice means for conveying said mixture at least one inch to said location, the diameter of said exit conduit is from 8 to 50 mils.

29. The apparatus according to claim 28, wherein said container is from 3 inch to 10 inch in height and from 1 inch to 4 inch in diameter.

* * * * *